US009233089B2

(12) United States Patent  
Nicolls et al.

(10) Patent No.: US 9,233,089 B2  
(45) Date of Patent: Jan. 12, 2016

(54) TREATMENT OF PULMONARY HYPERTENSION WITH LEUKOTRIENE INHIBITORS

(71) Applicant: The Board of Trustees of the Leland Stanford Junior University, Palo Alto, CA (US)

(72) Inventors: Mark R. Nicolls, Palo Alto, CA (US); Wen Tian, Mountain View, CA (US); Jayakumar Rajadas, Cupertino, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 13/839,321

(22) Filed: Mar. 15, 2013

(65) Prior Publication Data

US 2013/0251787 A1    Sep. 26, 2013

Related U.S. Application Data

(60) Provisional application No. 61/615,159, filed on Mar. 23, 2012, provisional application No. 61/642,818, filed on May 4, 2012, provisional application No. 61/729,091, filed on Nov. 21, 2012.

(51) Int. Cl.
| | |
|---|---|
| *A61K 31/198* | (2006.01) |
| *A61K 31/222* | (2006.01) |
| *A61K 31/197* | (2006.01) |
| *A61K 31/40* | (2006.01) |
| *A61K 31/216* | (2006.01) |
| *A61K 31/428* | (2006.01) |
| *A61K 45/06* | (2006.01) |

(52) U.S. Cl.
CPC ............ *A61K 31/198* (2013.01); *A61K 31/197* (2013.01); *A61K 31/216* (2013.01); *A61K 31/222* (2013.01); *A61K 31/40* (2013.01); *A61K 31/428* (2013.01); *A61K 45/06* (2013.01)

(58) Field of Classification Search  
None  
See application file for complete search history.

(56) References Cited

U.S. PATENT DOCUMENTS 4,963,588 A * 10/1990 Uzuka et al. .................. 514/563  
2013/0196973 A1* 8/2013 Abeywardane et al. . 514/210.21

FOREIGN PATENT DOCUMENTS

WO   2010027762   3/2010  
WO   2013012844   1/2013

OTHER PUBLICATIONS

Muskardin et al., "Modulation of Pulmonary Leukotriene Formation and Perfusion Pressure by Bestatin, an Inhibitor of Leukotriene A4 Hydrolase", Biochem. Pharm., 48(1), pp. 131-137 (1994).*

(Continued)

*Primary Examiner* — Bethany Barham  
*Assistant Examiner* — Barbara Frazier  
(74) *Attorney, Agent, or Firm* — Bozicevic, Field & Francis LLP; Pamela Sherwood

(57) ABSTRACT

Pulmonary arterial hypertension (PAH) can be prevented in persons susceptible to the diseases and PAH patients can be treated by administering an effective dose of a leukotriene inhibitor. Suitable inhibitors include leukotriene $A_4$ hydrolase ($LTA_4H$) inhibitors, leukotriene $B_4$ receptor (BLT1/BLT2) antagonists, 5-lipoxygenase (5-LO) inhibitors, and 5-lipoxygenase activating protein (FLAP) inhibitors.

18 Claims, 8 Drawing Sheets

(56) References Cited

OTHER PUBLICATIONS

Fink M P et al: A Novel Leukotriene B4-Receptor Antagonist in Endotoxin Shock: A Prospective, Controlled Trial in a Porcine Model, Cancer Investigation, Informa Healthcare, vol . 21, No. 12, Jan. 1, 1993, pp. 1825-1837.

Jones John E et al: Effect of 5-lipoxygenase on the development of pulmonary hypertension in rats., American Journal of Physiology. Heart and Circulatory Physiology, vol. 286, No. 5, May 2004, pp. H1775-H1784.

* cited by examiner

I  PAECs treated with LTB$_4$
(W/O MØ)

J  PAECs treated with LTB$_4$ + U75302
(W/O MØ)

A

B

C

D

E

Serum LTB$_4$ levels from controls versus treatment naiive patients with pulmonary arterial hypertension (PAH) demonstrate substantially higher levels in patients with connective tissue disease associated PAH (CTD-APAH). P value reflects non-parametric one-way analysis of variance using the Kruskal-Wallis test.

TREATMENT OF PULMONARY HYPERTENSION WITH LEUKOTRIENE INHIBITORS

RELATED APPLICATIONS

This application claims priority to, and the benefit of, U.S. Ser. No. 61/615,159, filed Mar. 23, 2012, 61/642,818, filed May 4, 2012, and 61/729,091, filed Nov. 21, 2012, the contents of each are herein incorporated by reference in their entireties.

GOVERNMENT SUPPORT

This invention was made with U.S. Government support under National Institutes of Health grant HL082662 and HL095686. The Government has certain rights in the invention.

BACKGROUND

Pulmonary arterial hypertension (PAH) is a disorder characterized by high blood pressure in the arteries of the lungs. PAH is one of the five classes of pulmonary hypertension (PH). The other four types of PH are venous, hypoxic, thromboembolic and miscellaneous PH.

PAH is a condition in which the progressive obliteration of the pulmonary vasculature leads to increased resistance to blood flow through the lungs. In turn, this obstruction leads to right heart failure and, ultimately, death. PAH mainly affects young and middle-aged women.

Current methods of treating PAH focus on prolonging patient lifespan and enhancing patient quality of life. Such methods include administration of: vasodilators such as prostacyclin, epoprostenol, and sildenafil; endothelin receptor antagonists such as bosentan; calcium channel blockers such as amlodipine, diltiazem, and nifedipine; anticoagulants such as warfarin; supplemental oxygen therapy and diuretics. When medical treatment fails, the final therapeutic option is lung and/or heart-lung transplantation. Each of these methods, however, suffers from one or multiple drawbacks such as lack of effectiveness, serious side effects, low patient compliance, and high cost.

Accordingly, new compounds, compositions of those compounds in the form of pharmaceutical formulations, medicaments containing those formulations and unit dose forms of them, and methods for treating PAH are needed. The present invention addresses these needs.

SUMMARY OF THE INVENTION

In a first aspect, the present invention provides a method of preventing and treating pulmonary arterial hypertension (PAH) by administering a therapeutically effective dose of a leukotriene inhibitor. In various embodiments, the PAH is immune-dysregulated PAH. In various embodiments, the PAH is associated with high levels of $LTB_4$.

In one embodiment, the leukotriene inhibitor is an inhibitor (e.g., a selective or competitive inhibitor) of $LTA_4H$. The leukotriene inhibitor can also be a pharmaceutically acceptable salt thereof a $LTA_4H$ inhibitor. In various embodiments, the $LTA_4H$ inhibitor is selected from the group consisting of ubenimex, CTX4430, JNJ26993135, JNJ40929837, DG051, and analogs of any of the foregoing with $LTA_4H$ inhibitory activity.

In another embodiment, the leukotriene inhibitor is a BLT1/BLT2 antagonist. In various embodiments, the BLT1/BLT2 antagonist is selected from the group consisting of LY293111, ONO4057, CP195543, CGS25019C, Biomed 101, BIIL284BS, DW1350, LY255283, and analogs of any of the foregoing with BLT1/BLT2 antagonist activity.

In another embodiment, the leukotriene inhibitor is a 5-LO/FLAP inhibitor. In various embodiments, the 5-LO/FLAP inhibitor is a 5-LO inhibitor. In various embodiments, the 5-LO inhibitor is selected from the group consisting of zileuton, MK0633, ZD2138, and VIA2291591, and analogs of any of the foregoing with 5-LO inhibitory activity. In various embodiments, the 5-LO/FLAP inhibitor is a FLAP inhibitor. In various embodiments, the FLAP inhibitor is selected from the group consisting of DG031, MK886, GSK MK591, and analogs of any of the foregoing with FLAP inhibitory activity.

In various of these embodiments, the $LTA_4H$ inhibitor, or pharmaceutically acceptable salt thereof, is administered orally or via inhalation. The therapeutically effective dose of a $LTA_4H$ inhibitor, or an analog or pharmaceutically acceptable salt thereof, is administered orally, although other means of administration, including administration by inhalation, are provided by the invention. In various of these embodiments, the therapeutically effective dose is administered once daily. In various of these embodiments, the therapeutically effective dose is administered on consecutive days for at least a week, at least a month, at least a year, or on as needed basis for the rest of the patient's life. The therapeutically effective dose of a $LTA_4H$ inhibitor (e.g., ubenimex or analog of ubenimex) or pharmaceutically acceptable salt thereof, can be about 10-500 mg/day, about 50-400 mg/day, about 100-200 mg/day, or about 120-180 mg/day. A $LTA_4H$ inhibitor (e.g., ubenimex or analog or ubenimex) or pharmaceutically acceptable salt thereof, can be administered to a subject at about 20-80 mg twice a day or about 20-80 mg three times a day. For example, a $LTA_4H$ inhibitor (e.g., ubenimex or an analog or ubenimex) or pharmaceutically acceptable salt thereof, is administered at about 60 mg twice a day or about 60 mg three times a day.

The invention also provides a $LTA_4H$ inhibitor (e.g., ubenimex or an analog of ubenimex) or pharmaceutically acceptable salt thereof, in a pharmaceutical formulation including at least one pharmaceutically acceptable carrier. The invention also provides a pharmaceutical composition containing 0.5%-50% of ubenimex and a pharmaceutically acceptable carrier. The invention further provides a pharmaceutical composition including ubenimex and a plurality of particles, where the plurality of particles is a plurality of liposomes comprising 1,2-distearoyl-sn-glycero-3-phosphoethanolamine-N-[amino(polyethylene glycol)] or a plurality of microparticles comprising a hydrophilic polymer.

The method of the invention include administration of a therapeutically effective amount of at least one additional active agent other than a $LTA_4H$ inhibitor. For example, the at least one additional active agent can include a vasodilator, such as a Type V phosphodiesterase inhibitor (e.g., sildenafil, tadalafil, vardenafil). Also, the invention provides a pharmaceutical formulation containing ubenimex and an additional active agent, such as a vasodilator.

The invention includes a method of treating PAH, or a disorder disclosed herein, where the method includes a combination therapy in which a patient in need of treatment is administered a leukotriene inhibitor (e.g., a $LTA_4H$ inhibitor, such as ubenimex) in combination with one or more drugs approved for the treatment of PAH, for the treatment of a PAH associated condition, or for the treatment of a disorder disclosed herein, or a combination thereof. For example, an additional active agent can include but is not limited to a prostaglandin (e.g., epoprostenol, treprostinil, iloprost, selexipag), an endothelin receptor antagonist (e.g., bosentan, ambrisentan, macitentan), or a guanylate cyclase inhibitor (e.g., riociguat).

In various of these embodiments, the leukotriene inhibitor is administered in combination with one or more other drugs useful in preventing or treating PAH. In some of these embodiments, two or more leukotriene inhibitors are administered in accordance with the invention. For example, leukotriene inhibitors from the $LTA_4H$ inhibitor and BLT1/BLT2 antagonist classes can be administered in combination in accordance with the invention. In some of these embodiments, the patient has PAH associated with a second condition, and the combination therapy comprises administering a drug useful in treating the second condition as well as one or more leukotriene inhibitors administered in accordance with the present invention.

In a second aspect, the compounds provided by the invention are used in the manufacture of a medicament for the treatment or prevention of PAH, wherein said medicament is a leukotriene inhibitor (e.g., a $LTA_4H$ inhibitor, or pharmaceutically acceptable salt thereof). In various embodiments, the medicament is formulated for oral administration, including both immediate release and sustained release pharmaceutical formulations. In other embodiments, the medicament is formulated for administration by inhalation. In all of these embodiments, the invention provides unit dose forms of the medicament.

In a third aspect, the present invention provides leukotriene inhibitors, methods for their synthesis, pharmaceutical formulations and unit dose forms of those pharmaceutical formulations, and methods for manufacturing a medicament comprising those pharmaceutical formulations and consisting of those unit dose forms.

In a fourth aspect, the present invention provides methods for treating diseases or disorders other than PAH and uses of the compounds of the invention for manufacturing medicaments to treat these diseases. Such other diseases are selected from the group consisting of coronary artery disease (CAD), non-CAD atherosclerotic conditions, including peripheral vascular disease (PVD), aortic atherosclerosis, and cerebral arteriosclerosis, diabetic retinopathy, ischemia-reperfusion injury, emphysema, radiation-induced organ and tissue injury, corpus luteum regression, scleroderma, systemic sclerosis, and diseases of immune dysregulation. A method of the invention can be used for treatment or prevention of PAH in a subject with PAH and at least one additional disorder or disease.

In a fifth aspect, the present invention provides methods for selecting patients likely to benefit from the therapies of the invention, as well as methods for determining whether a patient is responding to such therapy. In these methods, a biological sample, which may be, for example and without limitation, a breath, sputum, tissue, plasma or serum sample, urine, and the level of $LTB_4$ in the sample is determined and compared to a control value. Depending on the application of the method, the control value may be determined from one or more normal individuals not suffering from PAH or other disease amenable to treatment with the methods of the invention or not in need of a therapy of the invention. The control value can also be determined from a sample previously obtained from the patient. Generally, higher (or elevated) levels of $LTB_4$ relative to a control value determined from a normal, non-diseased individual or population indicate that a subject will benefit from a preventive or therapeutic treatment method of the invention. Lower levels generally indicate that a patient is responding to therapy or, for a subject not on such therapy, that the therapeutic methods of the invention may not be as beneficial for that subject. In one embodiment, the methods of the invention include a step of obtaining a biological sample from a subject and determining the amount of LTB4 in the sample prior to administering an effective dose of a leukotriene inhibitor.

For example, a higher or elevated level of LTB4 of at least 2-fold higher, at least 3-fold higher, at least 4-fold higher, or at least 5-fold higher than the control value indicates that the patient is in need of treatment using a therapy of the invention or that the patient is likely to respond to a therapy of the invention. For example, the control LTB4 level is 600 pg/mL or less, 500 pg/mL or less, 400 pg/mL or less, 300 pg/mL or less, 200 pg/mL, or 100 pg/mL or less. The control LTB4 level can also be 30 pg/mg or less, 20 pg/mg or less, 10 pg/mg or less, 7.5 pg/mg or less, or 5 pg/mg of tissue or less. For example, the elevated level of LTB4 is 100 pg/mL or higher, 200 pg/mL or higher, 300 pg/mL or higher, 400 pg/mL or higher, 500 pg/mL or higher, 600 pg/mL or higher, or 1000 pg/mL or higher. The elevated level of LTB4 can also be 40 pg/mg of tissue or higher, 30 pg/mg of tissue or higher, 20 pg/mg of tissue of higher, 10 pg/mg of tissue or higher, 7.5 pg/mg of tissue or higher, or 5 pg/mg of tissue or higher.

Standard methods for assessing $LTB_4$ levels are utilized. Additionally, new methods for assessing $LTB_4$ are provided, wherein leukotriene levels are assessed in PAH patients to provide a rapid non-invasive evaluation of pulmonary inflammation.

The method further comprises administering an effective amount of a $LTA_4H$ inhibitor of the invention to a patient determined to be likely to benefit from, in need of, or likely to respond to, a therapy of the invention, thereby treating or preventing PAH, or a disorder disclosed in the invention, in the patient.

Current pathogenetic concepts about the development of PAH focus on aberrant bone morphogenetic protein receptor-2 (BMPR2) and metabolic signaling, growth factors, elastases, proteases and cytokines; these factors increase vasoconstrictive tone and lead to obliterative proliferation in the small pulmonary arterioles. See, e.g., Schermuly et al., *Nat Rev Cardiol* 8:443-455 (2011). PAH is either idiopathic or associated with a variety of disorders, such as congenital heart disease, connective tissue disorders (e.g., scleroderma, systemic lupus erythematosus, systemic sclerosis, Hashimoto's thyroiditis, Sjögren's Syndrome, and the antiphospholipid antibody syndrome), portal hypertension, and HIV infection. Increased pulmonary artery endothelial cell death and enhanced pulmonary artery smooth muscle cell proliferation, hypertrophy, and survival are considered important features of disease pathogenesis.

The present invention also provides methods of determining efficacy of a PAH treatment in a subject in need thereof by (a) measuring an endpoint level of a parameter in a subject in need thereof, where the endpoint level is measured after treatment has started, (b) comparing the endpoint level of the parameter to a baseline level of the parameter, where the baseline level is measured in the same subject before treatment is begun, and (c) determining the efficacy of the PAH treatment based on the comparison step.

Furthermore, the present invention provides methods of determining efficacy of a PAH treatment in a subject in need thereof by (a) measuring the endpoint level of a parameter in a subject in need thereof after treatment has begun, (b) comparing the endpoint level of the parameter to a reference value of the parameter, where the reference value is an average value of the parameter determined from a population of patients suffering from PAH, and (c) determining the efficacy of the PAH treatment based on the comparison step.

An exemplary parameter used in these methods is LTB4 level. A level of LTB4 is determined in the biological sample of a subject. A baseline or reference value of LTB4 can be 100 pg/mL or greater, 200 pg/mL or greater, 300 pg/mL or greater, 400 pg/mL or greater, 500 pg/mL or greater, 600 pg/mL or greater, or 100 pg/mL or greater. The treatment provided in the invention is efficacious if, after treatment has started, the endpoint LTB4 level of the subject decreases from the baseline or reference LTB4 level. For example, the endpoint LTB4 level of the subject decreases to 600 pg/mL or less, 500 pg/mL or less, 400 pg/mL or less, 300 pg/mL or less, 200 pg/mL or less, or 100 pg/mL or less. Also, the treatment provided in the invention is efficacious if, after treatment has started, the endpoint LTB4 level is 30 pg/mg of tissue or lower, 20 pg/mg of tissue of lower, 10 pg/mg of tissue or lower, 7.5 pg/mg of tissue or lower, or 5 pg/mg of tissue or lower. In other embodiments, the treatment provided in the invention is efficacious if, after treatment has started, the endpoint LTB4 level is lower than the baseline LTB4 level by 2-fold or more, 3-fold or more, 4-fold or more, or 5-fold or more.

An exemplary parameter used in the methods is pulmonary vascular resistance (PVR). The baseline or reference PVR level can be 200 dyn·sec/cm$^5$ or greater, 240 dyn·sec/cm$^5$ or greater, 300 dyn·sec/cm$^5$ or greater, 400 dyn·sec/cm$^5$ or greater, 500 dyn·sec/cm$^5$ or greater, 600 dyn·sec/cm$^5$ or greater, 700 dyn·sec/cm$^5$ or greater, or 800 dyn·sec/cm$^5$ or greater. The treatment provided in the invention is efficacious if after treatment has started, the endpoint PVR level of the subject decreases from the baseline or reference PVR level by 70 dyn·sec/cm$^5$ or more, 100 dyn·sec/cm$^5$ or more, 130 dyn·sec/cm$^5$ or more, or 160 dyn·sec/cm$^5$ or more.

Another exemplary parameter used in the methods is pulmonary arterial pressure (PAP). The baseline or reference PAP level can be 20 mmHg or greater, 25 mmHg or greater, 30 mmHg or greater, 35 mmHg or greater, 40 mmHg or greater, 45 mmHg or greater, 50 mmHg or greater, 60 mmHg or greater, or 70 mmHg or greater. The treatment provided in the invention is efficacious if, after treatment has started, the endpoint PAP level of the subject decreases from the baseline or reference PAP level by 0.5 mmHg or more, 1 mmHg or more, 1.5 mmHg or more, 5 mmHg or more, 10 mmHg or more, 20 mmHg or more, 30 mmHg or more, 40 mmHg or more, or 50 mmHg.

An exemplary parameter used in the methods can also be cardiac index (CI). A baseline or reference CI level can be 5 L/min/m$^2$ or lower, 2.5 L/min/m$^2$ or lower, 2 L/min/m$^2$ or lower, 1.5 L/min/m$^2$ or lower, or 1 L/min/m$^2$ or lower. A treatment provided in the invention is efficacious if, after treatment has started, the endpoint CI level increases from the baseline or reference CI level by 0.1 or more, 0.2 or more, 0.3 or more, 0.4 or more, 0.5 or more, 1 or more, or 2 or more.

An exemplary parameter used in the methods can be pulmonary capillary wedge pressure (PCWP). A baseline or reference PCWP level can be 36 mmHg or less, 24 mmHg or less, 18 mmHg or less, 10 mmHg, or 5 mmHg or less. A treatment provided in the invention is efficacious if, after treatment has started, the endpoint PCWP level increases from the baseline or reference PCWP level by 0.2 mmHg or more, 0.3 mmHg or more, 0.4 mmHg or more, 0.5 mmHg or more, 0.6 mmHg or more, 1 mmHg or more, or 5 mmHg or more.

Another exemplary parameter used in the methods can be right atrial pressure (RAP). A baseline or reference RAP level can be 4 mmHg or more, 6 mmHg or more, 8 mmHg or more, 10 mmHg or more, 12 mmHg or more, 16 mmHg or more, 20 mmHg or more, or 25 mmHg or more. A treatment provided in the invention is efficacious if after treatment has started, the endpoint RAP level of the subject decreases from the baseline or reference RAP level by 5 mmHg or more, 2.5 mmHg or more, 1 mmHg or more, 0.5 mmHg or more, or 0.2 mmHg or more.

An exemplary parameter used in the methods can be six-minute walk distance (6 MWD). A baseline or reference 6 MWD can be 50 m or less, 100 m or less, 200 m or less, 300 m or less, 400 m or less, or 500 m or less. A treatment provided in the invention is efficacious if, after treatment has started, the endpoint 6 MWD of the subject increases from the baseline or reference 6 MWD by 10 m or more, 15 m or more, 20 m or more, 25 m or more, 30 m or more, or 50 m or more. Alternatively or in addition, treatment provided in the invention is efficacious if, after treatment has started, the endpoint 6 MWD of the subject increases by 3% or more, 4% or more, 5% or more, 10% or more, or 20% or more of the baseline level.

Another parameter used in the methods can be brain natriuretic peptide (BNP) level. A baseline or reference BNP level can be 60 pg/mL or higher, 80 pg/mL or higher, 100 pg/mL or higher, 120 pg/mL or higher, 140 pg/mL or higher, 200 pg/mL or higher, 500 pg/mL or higher, or 1000 pg/mL or higher. A treatment provided in the invention is efficacious if, after treatment has started, the endpoint BNP level of the subject decreases from the baseline or reference BNP level. For example, the endpoint BNP level of the subject can decrease by 1 pg/mL or more, 2 pg/mL or more, 5 pg/mL or more, 10 pg/mL or more, 20 pg/mL or more, 100 pg/mL or more, 500 pg/mL or more, or 1000 pg/mL or more.

Diffusion of lung capacity (DLCO), or diffusion capacity of CO, can also be used in the methods as a parameter to determine efficacy. A baseline or reference DLCO can be 90% or less, 80% or less, 70% or less, 50% or less, 45% or less, or 40% or less. A treatment provided in the invention is efficacious if, after treatment has started, the endpoint DLCO is increased from the baseline level. For example, the endpoint DLCO can be increased from the baseline or reference DLCO by 1% or more, 5% or more, 10% or more, 15% or more, 20% or more, or 50% or more.

In addition, average survival rate can be used in the methods as a parameter to determine efficacy in a population of one or more subjects. A reference average survival rate is 95% or lower, 93% or lower, 90% or lower, 86% or lower, 82% or lower, or 78% or lower. The average survival rate can be an average 1-year survival rate. A treatment provided in the invention is efficacious in a population of one or more subjects if, after treatment has started, the average survival rate increases. For example, the average survival rate can increase from the reference average survival rate by 1% or more, 2% or more, 5% or more, 10% or more, or 20% or more.

Another exemplary parameter for use in the methods to determine efficacy of treatment in a subject is time to death after diagnosis with PAH. A reference time to death can be 1 year or less, 2 years or less, 5 years or less, or 7 years or less. A treatment provided in the invention is efficacious if, after treatment has started, the time to death of the subject is higher than the reference time to death. For example, the time to death of the subject can increase from the reference time to death by 0.5 years or more, 1 year or more, 2 years or more, 3 years or more, 4 years or more, 5 years or more, or 6 years or more.

The methods can further comprise continuing the therapy if the therapy is determined to be efficacious. The methods can comprise maintaining, tapering, reducing, or stopping the administered amount of a compound or compounds in the therapy if the therapy is determined to be efficacious. The methods can comprise increasing the administered amount of a compound or compounds in the therapy if it is determined not to be efficacious. Alternatively, the methods can comprise stopping therapy if it is determined not to be efficacious.

In another aspect, the present invention provides in silico methods to identify compounds with high binding affinity to $LTA_4H$. The in silico methods include the following steps: (1) providing compounds known to bind to $LTA_4H$, (2) identifying a candidate compound based on structure or shape similarity to known $LTA_4H$ binding compounds, (3) modeling the candidate compound into a docked position onto the $LTA_4H$ 3D structure, (4) calculating the predicted binding affinity of the candidate compound for $LTA_4H$, and (5) repeating steps 2-4 for different compounds. Optionally, the method further includes scoring or ranking the candidate compounds based on their predicted affinities for $LTA_4H$. In one embodiment, the predicted binding affinity of a compound selected to have high binding affinity to $LTA_4H$ is −7 kcal/mol, −8 kcal/mol, −9 kcal/mol, −10 kcal/mol, −15 kcal/mol, or higher affinity. The in silico methods are used to identify compounds selective for $LTA_4H$, i.e., the compounds have a higher binding affinity for $LTA_4H$ than for another target, such as 5-LO, FLAP, or another macromolecule. The in silico methods further include identifying a compound that inhibits or decreases $LTA_4H$ enzymatic activity. $LTA_4H$ enzymatic activity can be determined using methods known in the art. In one embodiment, a compound identified by the in silico methods are used to treat or prevent PAH, or another disorder disclosed herein.

Other features and advantages of the invention will be apparent from the following brief description of the drawings, detailed description, and claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the disclosure encompassed by the appended claims.

DETAILED DESCRIPTION OF THE INVENTION

The present invention generally relates to compounds, methods, pharmaceutical formulations, and medicaments for the treatment of PAH and other diseases. As demonstrated herein, inhibition of $LTB_4$ synthesis by blocking the activity of $LTA_4H$ or inhibition of $LTB_4$ binding to the BLT1/BLT2 is highly effective in preventing and treating PAH, and the invention provides a variety of compounds that act by a variety of mechanisms to inhibit that interaction. The compounds are referred to generically herein as "leukotriene inhibitors".

Pulmonary hypertension (PH), like systemic hypertension, is not a single disease but a group of diseases, which share the defining element of a mean pulmonary arterial pressure ≥25 mm Hg. PH has been classified and divided into 5 groups (Galie et al. *ERJ* (2009) December; 34(6):1219-63). This invention generally relates to preventing and treating the World Health Organization (WHO) group 1, or pulmonary arterial hypertension (PAH) group of, diseases characterized by elevated pulmonary arterial pressure and elevated blood flow resistance due to a precapillary pulmonary microangiopathy.

Another characteristic of the majority of WHO Group I patients is evidence of systemic inflammation. Inflammation can arise through multiple events induced by LTB4. Inflammation in PAH can occur through pulmonary arterial endothelial cell (PAEC) apoptosis, induced by LTB4, leading to occlusion of the pulmonary artery lumen and restriction of blood flow. Inflammation in PAH can promote pulmonary arterial smooth muscle cell (PASMC) proliferation and hypertrophy, induced by LTB4, leading to thickening of the pulmonary artery wall and restriction of blood flow. Thus, by inducing PAEC apoptosis while simultaneously promoting PASMC proliferation and hypertrophy, LTB4 causes two pathological processes highly implicated in PAH pathogenesis.

Figure 1:
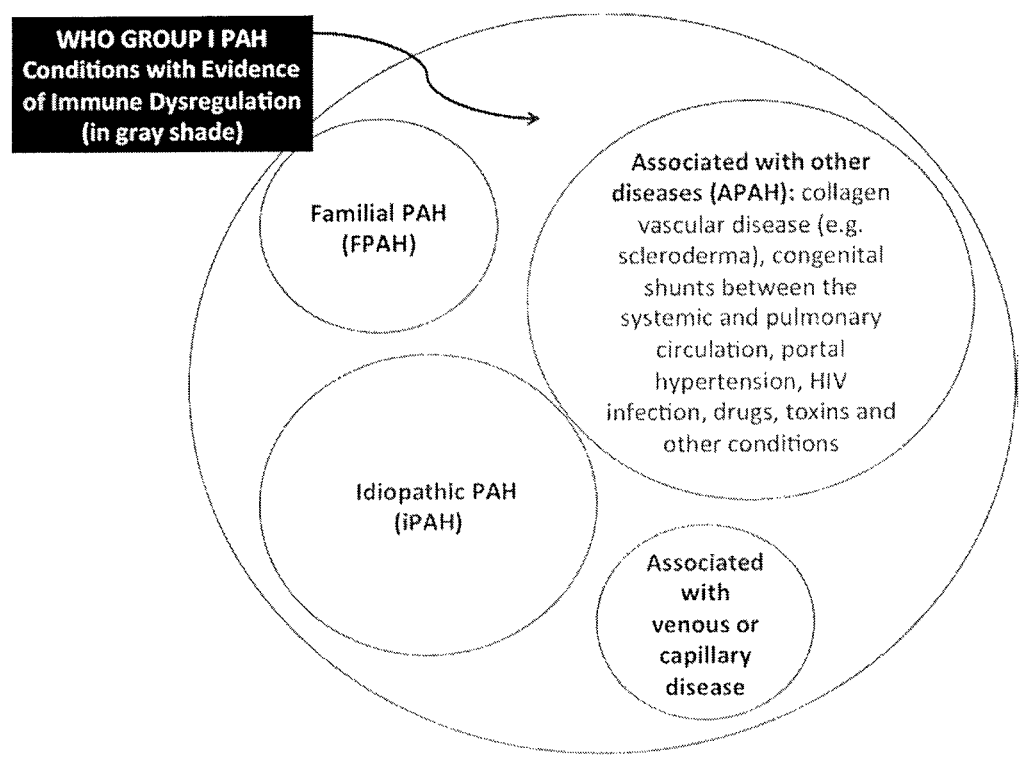
FIG. 1 is a Venn diagram showing WHO Group I PAH conditions with evidence of immune dysregulation.

Inflammation is a characteristic feature of the plexiform vascular lesions that characterize PAH lung disease. Although not part of the formal scheme of classifying PAH conditions, patients exhibiting evidence of pulmonary and systemic inflammation can be described as having 'dysregulated immunity', and these patients are referred to herein as having 'immune-dysregulation PAH'. This classification system is illustrated by the Venn diagram of FIG. 1. In one important embodiment, the present invention relates to the prevention of immune-dysregulation PAH in patients susceptible to the disease and the treatment of patients with the disease.

The Venn diagram (FIG. 1) shows that, for some PAH conditions, such as PAH associated with other diseases (APAH), the majority of associated diseases exhibit evidence of immune dysregulation, whereas for other conditions, such as familial PAH (FPAH), immune dysregulation may be occurring, but there is no evidence of it (or the evidence has not been observed or reported). Immune regulation is the normal response utilized by organisms to self-limit inflammation. In the absence of immune regulation, autoimmune injury can ensue; to reiterate, this absence of normal control is termed "immune dysregulation". 'Immune-dysregulated' is used herein instead of "autoimmune," because a rigorous series of proofs is required to call a condition an autoimmune disease, whereas the term 'immune-dysregulated' is used herein to refer to conditions characterized simply by exuberant inflammation in the absence of appropriate immune regulation. This invention provides methods and compositions relating to the treatment of PAH conditions associated with immune dysregulation; these diseases are collectively referred to herein as immune-dysregulated PAH and immune dysregulation-associated PAH.

A predisposition to inflammation can be identified by the detection of reduced regulatory T cell (Treg) populations and/or aberrant Treg function. In various important embodiments, a subject treated in accordance with the invention will have been subjected to a test that has identified that subject as having a predisposition to inflammation. In accordance with this aspect of the invention, to identify Group I PAH patients (including patients not otherwise manifesting symptoms of the disease and so amenable to treatment with the preventive methods of the invention) with evidence of immune dysregulation, one or more of the following laboratory assessments can be made: elevated serum cytokine measurements, such as for interleukin 1 (IL-1) and interleukin 6 (IL-6) as well as multiplex assays capable of detecting multiple cytokines and chemokines simultaneously, serum autoantibodies, and breath, sputum, tissue, plasma and serum leukotriene measurements.

The most relevant biochemical consequence of dysregulated immunity in PAH pathogenesis is elevated $LTB_4$. In one important embodiment, the invention further stratifies this PAH group into patients with high $LTB_4$ levels and those with lower levels. The methods of the invention are especially beneficial to PAH patients with high $LTB_4$ levels. Patients with other PH conditions express high levels of the cysteinyl leukotrienes $LTC_4$ and $LTD_4$, and patients with these conditions, especially those with normal $LTB_4$ levels, may be expected to respond less favorably to the therapies provided by this invention.

For a better appreciation of the benefits of the invention, the following review of the mechanism by which dysregulated immunity can arise in Group I PAH patients through aberrant Treg activity is provided. Normal immune regulation is accomplished by controlling inflammation through the action of Tregs, which are usually $CD4^+$ $CD25^{hi}$ cells. In animals with no Tregs, widespread autoimmune inflammation and disease is observed. In the athymic rat PH model, there are no T cells, so this inflammation-control mechanism is absent. When Tregs are injected into the animal before SU5416 (an agent that normally induces experimental PH through vascular injury), animals don't develop significant PH (Tamosiuniene et al, Circ Res (2011) 109: 867-79). The athymic rat effectively models Group I PAH, but by convention, in animal models, this disease is still referred to generically as 'PH'. To reiterate, this invention targets Group I PAH patients; especially those individuals expressing high $LTB_4$ levels in their lungs (as detected in breath or sputum) and/or their blood or tissues.

Like athymic rats, patients with immune-dysregulated PAH conditions are characterized by having low numbers of Tregs or abnormally-functioning Tregs that put them at risk for developing PAH (Nicolls et al., ERJ (2005) 26: 1110-8) as well as other, associated conditions. These associated conditions include a number Group I PAH conditions, including, for example in the APAH conditions: collagen vascular diseases (scleroderma, systemic sclerosis, lupus, Sjogren's), viral infections (Hepatitis B, C, HIV), and the antiphospholipid antibody syndrome. (For a detailed list of conditions associated with immune dysregulation PAH, please refer to (Nicolls et al., ERJ (2005) 26: 1110-8). Thus, a patient having one or more of these conditions as well as PAH is referred to herein as a "patient having PAH and an associated condition." Another Group I condition, iPAH, is also strongly associated with immune dysregulation in association with low numbers of pulmonary Tregs.

Tregs control both the adaptive (e.g., T and B cells) and innate (e.g., NK cells and macrophages) immune responses in inflammation. The present invention arises in part from the discovery of how an important consequence of inadequate control by Tregs is the activation of macrophages secreting $LTB_4$ and how that activation, in turn, leads to the death of pulmonary artery endothelial cells and proliferation of pulmonary arterial smooth muscle cells. In PAH patients amenable to treatment with the methods and compositions of the invention, unregulated macrophages are inappropriately activated and secrete $LTB_4$, which kills pulmonary artery endothelial cells, causes proliferation of pulmonary arterial smooth muscle cells, and causes PAH.

The present invention provides methods, compounds, and compositions for preventing the injurious inflammation that result from pulmonary vascular injury that occurs in the absence of normal immune regulation and in the presence of elevated LTB4 levels. For this group of PAH conditions (WHO Class I PAH), $LTB_4$ is a newly-appreciated mediator of vascular toxicity which, in accordance with the invention, can be effectively targeted to limit and reverse disease progression.

A brief description of the leukotriene pathway is provided. Arachidonic acid (AA) is liberated from the cellular membranes by phospholipase $A_2$ ($PLA_2$). Free AA can be metabolized to leukotrienes through the 5-LO pathway. In this pathway, AA is first converted to an intermediary $LTA_4$. $LTA_4$ is subsequently converted to $LTB_4$ through the action of $LTA_4H$, or to $LTC_4$ via $LTC_4S$. The biosynthesis of $LTB_4$ versus $LTC_4$ is controlled by the compartmentalization of all the synthetic enzymes and the nucleoplasmic/cytosolic localization of the phosphorylated and unphosphorylated 5-LO. Targeting 5-LO to the outer nuclear membrane promotes the formation of $LTC_4$, whereas targeting p5-LO to the inner nuclear membrane results in the production of $LTB_4$.

While not bound by any specific theory, $LTB_4$, rather than $LTC_4$, is the more highly-expressed leukotriene in PAH development in an animal model of dysregulated immunity. More specifically, in this rodent model of severe PAH, macrophages strongly express a serine 271 phosphorylated form of 5-lipoxygenase (p5-LO) resulting from p38 mitogen-activated protein kinase (MAPK) activation. Increased p5-LO led to the secretion of leukotriene $B_4$ ($LTB_4$) via increased $LTA_4$ hydrolase ($LTA_4H$) activity. In this model, the macrophage-derived $LTB_4$ was shown to induce 1) PAEC apoptosis; a process shown to be mediated by inhibition of the endothelial sphingosine kinase 1 (Sphk1)-endothelial nitric oxide synthase (eNOS) pathway; 2) PASMC proliferation and hypertrophy. As demonstrated in the examples below, inhibiting $LTA_4H$ reverses PAH in this animal model, decreases in vivo $LTB_4$ levels. Accordingly, the present invention provides, in part, a method for treating PAH by administering to a subject in need thereof a therapeutically effective amount of a compound or molecule that can inhibit or decrease $LTA_4H$ activity or decrease $LTA_4H$ levels, either of which results in decreased $LTB_4$ levels and/or activity, which in turn results in decreased $LTB_4$ signaling through the BLT1/BLT2. Alternatively, one can, in accordance with the invention, block binding of $LTB_4$ to the BLT1/BLT2 to treat PAH. An advantage of a selective $LTA_4H$ inhibitor is fewer adverse side effects than a less selective inhibitor of the LTB4 pathway.

The terminology used herein is for the purpose of describing particular embodiments only and is not intended to be limiting. In this specification and in the claims that follow, reference will be made to a number of terms, which shall be defined to have the definitions set forth below. Unless otherwise defined, all technical and scientific terms used herein have the same meaning as commonly understood by one of ordinary skill in the art to which this invention belongs. The singular forms also include the plural unless the context clearly dictates otherwise. Thus, the singular forms "a," "an" and "the" include plural referents unless the context clearly dictates otherwise.

Acronyms. The following acronyms are used throughout the specification and defined as follows: 5-LO: 5-lipoxygenase; FLAP: 5-lipoxygenase activating protein; AA: arachidonic acid; BMPR2: bone morphogenetic protein receptor 2; BALF: bronchoalveolar lavage fluid; $BLT_1$: leukotriene $B_4$ receptor 1; $BLT_2$: leukotriene $B_4$ receptor 2; COX: cyclooxygenase; DAF-2DA: diaminofluorescein-2 diacetate; DMSO: dimethyl-sulfoxide; eNOS: endothelial nitric oxide synthase; iPAH: idiopathic pulmonary arterial hypertension; LC-MS/MS: liquid chromatographic tandem mass spectrometric; $LTA_4$: leukotriene $A_4$, $LTA_4H$: leukotriene $A_4$ hydrolase; $LTB_4$: leukotriene $B_4$; $LTC_4$: leukotriene $C_4$; $LTC_4S$: leukotriene $C_4$ synthase; $LTD_4$: leukotriene $D_4$; $LTE_4$: leukotriene $E_4$; LV: left ventricle; MAPK: mitogen-activated protein kinase; NO: nitric oxide; NOS: nitric oxide synthase; p5-LO: pSer271 5-LO; PAH: pulmonary arterial hypertension; PAAT: pulmonary artery acceleration time; $PLA_2$: phospholipase $A_2$; $PGI_2$: prostaglandin $I_2$ (prostacyclin); PH: pulmonary hypertension; RV: right ventricle; RVSP: right ventricular systolic pressure; S: septum; SIP: sphingosine-1-phosphate; Sphk1: sphingosine kinase 1; SU: SU5416; Treg: regulatory T cell; VEGFR2: vascular endothelial growth factor receptor 2; WT: wild-type; PVR: pulmonary vascular resistance; PAP: mean pulmonary arterial pressure; CI: cardiac index; PCWP: pulmonary capillary wedge pressure; RAP: right atrial pressure; 6 MWD: six-minute walk distance; BNP: brain natriuretic peptide; and DLCO: diffusion of lung capacity.

"Active agent" and "therapeutic agent" means a compound, also referred to as a drug that exerts a preventive or therapeutic effect on a disease or disease condition. Active agent can refers not only to a single active agent but also to a combination of two or more different active agents.

"Alleviate" and "ameliorate" means a process by which the severity of a sign or symptom of a disorder is decreased. Importantly, a sign or symptom can be alleviated without being eliminated. Therapeutically effective dosages are expected to decrease the severity of, and so alleviate and ameliorate, a sign or symptom of disease.

"Aromatic heterocycle" or "heteroaryl" means a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic heterocyclic aromatic rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and $S(O)_p$, wherein p=1 or 2). In certain compounds, the total number of S and O atoms in the aromatic heterocycle is not more than 1.

"As-needed," in "as-needed administration," means that a formulation is administered to a patient when symptoms are observed, or when symptoms are expected to appear, or at any time that the patient and/or treating physician deems it appropriate to treat (therapeutically or prophylactically) undesirable symptoms (e.g., symptoms arising from a disease).

"Carbocycle" or "carbocyclic ring" means any stable 3, 4, 5, 6, 7, 8, 9, 10, 11, or 12-membered monocyclic, bicyclic or tricyclic ring, any of which can be saturated, unsaturated (including partially and fully unsaturated), or aromatic. Examples of such carbocycles include, but are not limited to, cyclopropyl, cyclobutyl, cyclobutenyl, cyclopentyl, cyclopentenyl, cyclohexyl, cyclohexenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring can also be present on the bridge. Fused (e.g., naphthyl and tetrahydronaphthyl) and spiro rings are also included.

"Combination therapy" and "co-therapy" means the administration of a first active agent and at least a second, different active agent as part of a specific treatment regimen intended to provide the beneficial effect from the co-action of the at least two active agents. The beneficial effect of the combination may include, but is not limited to, pharmacokinetic or pharmacodynamic co-action resulting from the combination of therapeutic agents. Administration of therapeutic agents in combination typically is carried out over a defined time period (usually minutes, hours, days or weeks depending upon the combination selected). Combination therapy is not intended to encompass the administration of two or more different therapeutic agents as part of separate monotherapy regimens that incidentally and arbitrarily results in a combination therapy of the invention. Combination therapy includes administration of at least two different therapeutic agents in a sequential manner, wherein each therapeutic agent is administered at a different time, as well as administration of at least two different therapeutic agents in a substantially simultaneous manner. Substantially simultaneous administration can be accomplished, for example, by administering to the subject a single capsule having a fixed ratio of each therapeutic agent or in separate capsules for each of the therapeutic agents. Sequential or substantially simultaneous administration of each therapeutic agent can be effected by any appropriate route, including, but not limited to, oral routes, intravenous routes, intramuscular routes, and direct absorption through mucous membrane tissues. The two different therapeutic agents can be administered by the same route or by different routes. For example, a first therapeutic agent of the combination selected may be administered by intravenous injection while the second therapeutic agent of the combination may be administered orally. Alternatively, for example, all therapeutic agents may be administered orally or all therapeutic agents may be administered by intravenous injection. The sequence in which the therapeutic agents are administered is not critical, unless otherwise stated. Combination therapy also includes the administration of the different therapeutic agents as described above in further combination with other biologically active ingredients and non-drug therapies (e.g., surgery or physical therapy). Where a combination therapy comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

"Compound" means a molecule and encompasses not only the specified molecular entity but, if the compound is an active agent or drug, also its pharmaceutically acceptable, pharmacologically active analogs, including, but not limited to, active metabolites, amides, conjugates, esters, hydrates, polymorphs, prodrugs, salts, solvates, and other such derivatives, analogs, including deuterated analogs and analogs containing radioactive atoms or other labeling moieties, and related compounds.

"Controlled release" refers to a drug-containing formulation or unit dose form thereof from which release of the drug is not immediate, i.e., with a controlled release formulation, administration does not result in immediate release of all of the drug administered into an absorption pool. The term is used interchangeably with "nonimmediate release" as defined in *Remington: The Science and Practice of Pharmacy, Nineteenth Ed.* (Easton, Pa.: Mack Publishing Company, 1995). In general, controlled release formulations include sustained release and delayed release formulations.

"Sustained release" and "extended release" means a drug formulation that provides for gradual release of a drug over an extended period of time, and typically, although not necessarily, results in substantially constant blood levels of a drug over an extended time period.

"Delayed release" refers to a drug formulation that, following administration to a patient, provides a measurable time delay before drug is released from the formulation into the patient's body.

"Dosage form" means any form of a pharmaceutical composition for administration to a subject (typically a human or animal of veterinary interest suffering from a disease or condition to be treated). "Dose" refers to an amount of active agent. "Unit dosage form" refers to a dosage form that contains a fixed amount of active agent. A single tablet or capsule is a unit dosage form. Multiple unit dosage forms can be administered to provide a therapeutically effective dose. A dosage form can include a combination of dosage forms.

"Effective amount" and "therapeutically effective amount" refers to a nontoxic but sufficient amount of an active agent to achieve a desired therapeutic effect.

"Heterocycle" means a stable 3, 4, 5, 6, 7, 8, 9, 10, 11, or 12-membered monocyclic, bicyclic or tricyclic ring which is saturated, unsaturated (including partially and fully unsaturated), or aromatic, and consists of carbon atoms and one or more ring heteroatoms, e.g., 1 or 1-2 or 1-3 or 1-4 or 1-5 or 1-6 heteroatoms, independently selected from nitrogen, oxygen, and sulfur, and including any bicyclic or tricyclic group in which any of the above-defined heterocyclic rings is fused or attached to a second ring (e.g., a benzene ring). The nitrogen and sulfur heteroatoms can optionally be oxidized (i.e., N→O and $S(O)_p$, wherein p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom can be substituted or unsubstituted (i.e., N or NR wherein R is H or another substituent, as defined). The heterocyclic ring can be attached to its pendant group at any heteroatom or carbon atom that results in a stable structure. The heterocyclic rings described herein can be substituted on carbon or on a nitrogen atom if the resulting compound is stable. A nitrogen in the heterocycle can optionally be quaternized. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. When a ring is bridged, the substituents recited for the ring can also be present on the bridge. Spiro and fused rings are also included.

"Immune dysregulation" is defined by the absence of normal immune regulation. Immune regulation is the normal response utilized by organisms to self-limit inflammation. With immune dysregulation, autoimmune injury can ensue. A critical means of controlling inflammation is through the action of regulatory T cells (Tregs), which are usually $CD4^+$ $CD25^{hi}$ cells. In animals with no Tregs, widespread autoimmune inflammation and disease is observed. Patients with immune-dysregulated PAH conditions, are characterized by having low numbers of Tregs or abnormally-functioning Tregs that may put them at risk for developing PAH. Tregs control both the adaptive (e.g., T and B cells) and innate (e.g., NK cells and macrophages) immune responses in inflammation. When unregulated macrophages are inappropriately activated, they secrete $LTB_4$, which kills pulmonary artery endothelial cells and causes PH.

Percentages and ratios used herein, unless otherwise indicated, are by weight.

"Pharmaceutically acceptable" means not biologically undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug Administration.

"Pharmaceutically acceptable salts" mean derivatives of an active agent produced by making acid or base salts thereof. Examples of pharmaceutically acceptable salts include, but are not limited to, mineral or organic acid salts of basic residues such as amines, alkali or organic salts of acidic residues such as carboxylic acids, and the like. Pharmaceutically acceptable salts include the conventional non-toxic salts or the quaternary ammonium salts of the parent compound formed, for example, from non-toxic inorganic or organic acids. Pharmaceutically acceptable salts include those formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. Pharmaceutically acceptable salts include solvent addition forms (solvates) or crystal forms (polymorphs) as defined herein, of the same salt.

"Pharmacologically active" (or "active") as in a "pharmacologically active" derivative or analog, refers to a derivative or analog having the same type of pharmacological activity as the parent compound of approximately equivalent in degree.

"Preventing" and "prevent" means avoiding the onset of a clinically evident disease progression altogether or slowing the onset of a pre-clinically evident stage of a disease in individuals at risk. Prevention includes prophylactic treatment of those at risk of developing a disease.

"Sign" means an indication of disease and includes conditions that can be observed by a doctor, nurse, or other health care professional.

"Small molecule" as used herein refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". The small molecule can have a MW less than or equal to about 5 kDa. In other embodiments, the drug molecule has a MW less than or equal to about 1.5 kDa.

"Subject in need thereof" refers to a human or other mammal suitable for treatment with an active agent. A subject in need thereof may have a disease or be at an increased risk, relative to the general population, of developing a disease.

"Symptom" means a sign or other indication of disease, illness, or injury. Symptoms may be felt or noticed by the individual experiencing them or by others, including by non-health-care professionals.

"Treating" and "treat" describes the management and care of a patient for the purpose of combating a disease, condition, or disorder and includes the administration of an active agent to alleviate the symptoms or complications of a disease, condition or disorder, or to eliminate the disease, condition or disorder.

Pulmonary hypertension (PH), like systemic hypertension, is not a single disease but a group of diseases, which share the defining element of a mean pulmonary arterial pressure $\geq 25$ mm Hg. PH has been classified and divided into 5 groups. The present invention provides compounds, compositions that are pharmaceutical formulations of those compounds, and medicaments, including unit dose forms of those pharmaceutical compositions for treating diseases characterized by the World Health Organization (WHO) as Group 1 pulmonary arterial hypertension (Group 1 PAH), diseases characterized by elevated pulmonary arterial pressure and vascular remodeling.

The compounds of the invention have been proven effective in an athymic rat model of PAH. The athymic rat effectively models Group I PAH, but by convention, in animal models, this disease is still referred to generically as "PH". This invention generally relates to treating Group I PAH patients or preventing Group 1 PAH in a subject likely to contract the disease (i.e., in those Group 1 PAH patients with immune-dysregulation, e.g., patients with a connective tissue disorder such as systemic sclerosis); especially those individuals expressing high $LTB_4$ levels in their lungs and/or blood. Other PH conditions express high levels of the cysteinyl leukotrienes $LTC_4$ and $LTD_4$, and patients with these conditions may be expected to respond differently, typically less favorably, to the therapies embodied by this invention.

High $LTB_4$ levels directly cause the endothelial cell death and smooth muscle cell growth and survival that results in PAH. The present invention provides a method for treating PAH by preventing, or blocking the harmful effects of, high $LTB_4$ levels and downstream signaling. This therapeutically beneficial result can be obtained by a variety of means in accordance with the invention. In one embodiment, prevention or treatment of PAH in a subject is accomplished in accordance with the invention by administering a therapeutically effective amount of a leukotriene inhibitor compound that can inhibit $LTA_4H$, which results in decreased $LTB_4$ levels, which in turn results in decreased $LTB_4$ bio-synthesis. Also, one can, in accordance with the invention, block binding of $LTB_4$ to BLT1/BLT2, which in turn results in decreased $LTB_4$ signaling, to treat PAH. Alternatively, one can, in accordance with the invention, block the activity of either or both 5LO and/or FLAP, which in turn shuts down the conversion of AA to $LTA_4$, to treat PAH.

Each of these various methods and compounds for practicing those methods is described in this section. In part A, methods utilizing $LTA_4H$ competitive inhibitors are described. In part B, methods utilizing BLT1/BLT2 antagonists are described. In part C, methods utilizing 5-LO or FLAP inhibitors are described. In part E, combination therapies employing one or more of the leukotriene inhibitors and one or more drugs for treating a PAH associated disease are described.

An $LTA_4H$ inhibitor as referred to herein is a compound that inhibits the enzymatic function of $LTA_4H$, which enzymatic function includes both the aminopeptidase activity and the epoxide hydrolase activity. Preferably, the compound is a small molecule compound.

An $LTA_4H$ inhibitor provided by the present invention to treat PAH, or other disorders disclosed herein, is ubenimex, (2S)-2-[[(2S,3R)-3-amino-2-hydroxy-4-phenylbutanoyl]amino]-4-methylpentanoic acid, the structure of which is shown below, or analogs thereof.

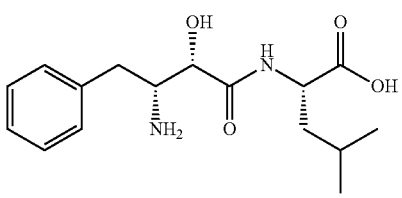

Prior to applicants' discovery described herein, ubenimex (brand name Bestatin) had been described to be ineffective for treating pulmonary injury and inflammation. (see, e.g., Ono et al., J Appl Physiol, 74:(4) 1534-1542, 1993). Patel et al. implies that Bestatin, as an aminopeptidase inhibitor which blocks the ANG IV related vasorelaxation, might have adverse effects to pulmonary hypertension. (see, e.g., Patel et al., Am J Physiol Lung Cell Mol Physiol 275:L1061-L1068, 1998). Accordingly, it is surprisingly unexpected that the compounds of the present invention can prevent pulmonary endothelial cell apoptosis via, e.g., inhibiting biosynthesis of $LTB_4$, a leukotriene that induces endothelial cell apoptosis by inhibition of activated Sphk1 and/or eNOS. Moreover, it is surprisingly unexpected that the compounds of the present invention are highly effective in treating PAH.

Specifically, $LTA_4H$ inhibitors, such as ubenimex, demonstrated potent in vivo efficacy in an athymic rat model of PAH. In the model, PH was first initiated by a single injection of a VEGFR2 inhibitor, SU5416, and monitored by weekly echocardiography. Survival of the animals was recorded on daily basis. A formulation of ubenimex was prepared by mixing PEG-400 with ubenimex and HPCD, and was given orally once a day at 4 different doses: 0.25 mg/kg, 0.5 mg/kg, 0.75 mg/kg, 1 mg/kg, beginning 3 weeks (21 days) after SU5416 administration (when advanced PH was confirmed by ECHO) for a total of 2 weeks (14 days). After 5 weeks (day 35), animals were sacrificed after right heart catheterization. A dose dependent improvement in right ventricular systolic pressure (RVSP), right ventricular hypertrophy (RVH) and survival was achieved in all four doses of ubenimex administered. Oral availability of ubenimex was determined by pharmacokinetic analysis. Ubenimex was absorbed rapidly within 2 hrs and was eliminated from the body with a $T_{1/2}$ of 12 hrs (different formulations provide varying half life times).

In various embodiments of the invention, ubenimex, including but not limited to ubenimex in the Bestatin 10 mg or 30 mg unit dosage forms commercially available, is administered to a patient with PAH or other vascular disease. In some embodiments, the patient is selected from the group of patients consisting of patients not known to have cancer, patients not concurrently being treated with any anti-cancer therapy, and patients not suffering from ANLL. In some embodiments, the patient has idiopathic PAH. In other embodiments, the patient has PAH associated with a connective tissue disorder (CTD). Exemplary CTDs are systemic sclerosis, systemic lupus erythematosus, and mixed CTD.

Oral doses of ubenimex generally in the range of 10 mg to 180 mg per day are administered to a subject in need thereof in accordance with one embodiment of the invention to improve functioning and outcome in the prevention and treatment of PAH. In one embodiment, the daily dose is 10 mg. In another embodiment, the daily dose is 60 mg. In another embodiment, the daily dose is 90 mg. In another embodiment, the daily dose is 120 mg. In another embodiment, the daily dose is 180 mg. Thus, depending on the patient, the daily dose can be, for example and without limitation, 10 mg, 30 mg, 40 mg, 50 mg, 60 mg, 80 mg, 90 mg, 100 mg, 120 mg, 130 mg, 150 mg, and 180 mg. Unit dose forms with each of these amounts of ubenimex are provided by the invention; alternatively, a Bestatin unit dose form can also be used. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject in need thereof is a human.

While a daily dose in the range provided above can be conveniently administered QD (daily), the present invention provides methods and unit dose forms suitable for other dosing schedules. For example and without limitation, BID (twice a day) and TID (three times a day) administration can also be used to achieve a beneficial therapeutic effect. In some embodiments, the ubenimex dose administered is 60 mg BID (120 mg per day) or 60 mg TID (180 mg/day).

Ubenimex analogs useful in the methods and pharmaceutical compositions of the invention include $LTA_4H$ inhibitor compounds described in U.S. Pat. Nos. 4,185,156; 4,189,604; 4,370,318; and 4,474,764, each of which is incorporated herein by reference.

An $LTA_4H$ inhibitor provided by the present invention to treat PAH, or other disorders disclosed herein, is JNJ26993135, 1-[4-(benzothiazol-2-yloxy)-benzyl]-piperidine-4-carboxylic acid, the structure of which is shown below.

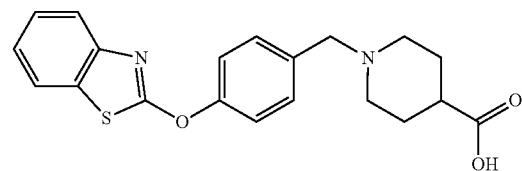 [SMILES: O=C(O)C1CCN(Cc2ccc(Oc3nc4ccccc4s3)cc2)CC1]

Oral doses of JNJ26993135 generally in the range of 50 mg to 500 mg per day are administered to a subject in need thereof in accordance with one embodiment of the invention to improve functioning and outcome in the treatment of PAH. In one embodiment, the daily dose is 50 mg. In another embodiment, the daily dose is 150 mg. In another embodiment, the daily dose is 300 mg. In another embodiment, the daily dose is 500 mg. Thus, depending on the patient, the daily dose can be, for example and without limitation, 50 mg, 60 mg, 100 mg, 120 mg, 150 mg, 240 mg, 300 mg, 400 mg, and 500 mg. Unit dose forms with each of these amounts of JNJ26993135 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject in need thereof is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

JNJ26993135 analogs useful in the methods and pharmaceutical compositions of the invention include the $LTA_4H$ inhibitor compounds described in US Patent Application Publication Nos. 20080194630A1; 20050043379A1 and 20050043378A1, each of which is incorporated herein by reference.

An LTA$_4$H inhibitor provided by the present invention to treat PAH, or other disorders disclosed herein, is JNJ40929837. Oral doses of JNJ40929837 generally in the range of 10 mg to 500 mg per day are administered to a subject in need thereof in accordance with one embodiment of the invention to improve functioning and outcome in the treatment of PAH. In one embodiment, the daily dose is 50 mg. In another embodiment, the daily dose is 100 mg. Thus, depending on the patient, the daily dose can be, for example and without limitation, 10 mg, 20 mg, 30 mg, 40 mg, 50 mg, 60 mg, 70 mg, 80 mg, 100 mg, 150 mg, 200 mg, or 500 mg. Unit dose forms with each of these amounts of JNJ40929837 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject in need thereof is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

JNJ40929837 analogs useful in the methods and pharmaceutical compositions of the invention include the LTA$_4$H inhibitor compounds described in Barchuk. "A Phase 2a, Randomized, Controlled Study of JNJ-40929837, an LTAH Inhibitor, in Patients with Asthma." *2$^{nd}$ Allergy & Respiratory Drug Discovery Conference*, Jan. 31-Feb. 1, 2013, San Diego, Calif., which is incorporated herein by reference.

An LTA$_4$H inhibitor provided by the present invention to treat PAH, or other disorders disclosed herein, is DG051, N,N-diethyl-2-[4-methoxy-3-(2-phenylethoxy)phenyl]ethanamine, the structure of one salt of which is shown below.

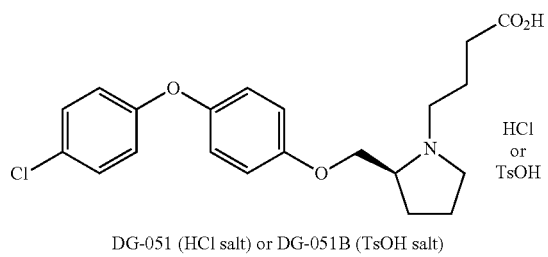 [SMILES: O=C(O)CCCN1CCC[C@H]1COc1ccc(Oc2ccc(Cl)cc2)cc1]

DG-051 (HCl salt) or DG-051B (TsOH salt)

Oral doses of DG051 generally in the range of 50 mg to 300 mg per day are administered to a subject in need thereof in accordance with one embodiment of the invention to improve functioning and outcome in the treatment of PAH. In one embodiment, the daily dose is 50 mg. In another embodiment, the daily dose is 150 mg. In another embodiment, the daily dose is 300 mg. Thus, depending on the patient, DG051 can be administrated, for example and without limitation, 50 mg, 100 mg, 150 mg, 200 mg, 250 mg and 300 mg per day. Unit dose forms with each of these amounts of DG051 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject in need thereof is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

DG051 analogs useful in the methods and pharmaceutical compositions of the invention include the LTA$_4$H inhibitor compounds described in U.S. Pat. No. 7,402,684; J Med. Chem. 2010 Jan. 28; 53(2):573-85; Bio-org Med Chem. Lett. 2009 Nov. 15; 19(22):6275-9, each of which is incorporated herein by reference.

An LTA$_4$H inhibitor provided by the present invention to treat PAH, or other disorders disclosed herein, is CTX-4430, also named EP-501, or an analog or pharmaceutically acceptable salt thereof (see Khim et al., 2008, Bioorg. & Med. Chem. Ltrs. 18:3895-3898, the contents of which are incorporated herein by reference).

The drug is a highly potent, orally bioavailable LTA$_4$H Inhibitor with the human dose projected to be less than 100 mg once daily. Oral doses of CTX-4430 generally in the range of 10 mg to 100 mg per day are administered to the subject in need thereof in accordance with one embodiment of the invention to improve functioning and outcome in the treatment of PAH. In one embodiment, the daily dose is 10 mg. In another embodiment, the daily dose is 50 mg. In another embodiment, the daily dose is 100 mg. Thus, depending on the patient, the daily dose can be, for example and without limitation, 10 mg, 20 mg, 30 mg, 40 mg, 50 mg, 60 mg, 70 mg, 80 mg, 90 mg and 100 mg. Unit dose forms with each of these amounts of CTX-4430 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

The present invention also provides leukotriene inhibitor compounds of the LTA$_4$H inhibitor class useful in the methods and pharmaceutical formulations of the invention of the formula:

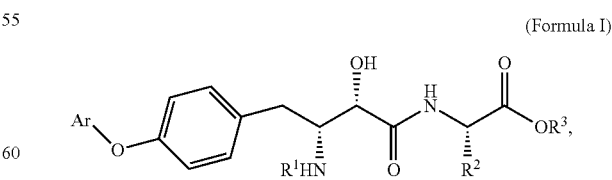

(Formula I)

or a pharmaceutically acceptable salt, ester, hydrate, solvate, prodrug, metabolite, or analog thereof, where Ar may be a (a) 3-14 membered saturated, unsaturated, or aromatic carbocycle, or (b) 3-14 membered saturated, unsaturated, or aromatic heterocycle containing one or more heteroatoms selected from the group consisting of N, O, and S; where (a)-(b) is optionally substituted with one or more groups selected from halogen, $C_1$-$C_6$ alkyl, O—($C_1$-$C_6$ alkyl), $NH_2$, $NH(C_1$-$C_6$ alkyl), $N(C_1$-$C_6$ alkyl)$_2$, $CF_3$, $CF_2H$, and $CFH_2$; $R^1$ may be hydrogen or $C(O)OR^a$; $R^a$ may be $C_1$-$C_6$ alkyl; $R^2$ may be $C_1$-$C_6$ alkyl; and $R^3$ may be hydrogen or $C_1$-$C_6$ alkyl.

In one embodiment, the compound is of the formula:

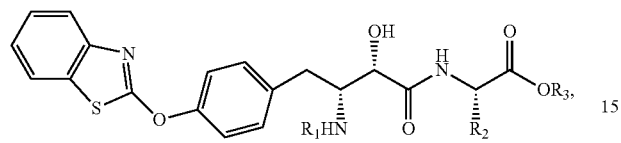

(Formula II)

or a pharmaceutically acceptable salt, ester, hydrate, solvate, prodrug, metabolite, or analog thereof, where $R^1$ may be hydrogen or $C(O)OR^a$; $R^a$ may be $C_1$-$C_6$ alkyl; $R^2$ may be $C_1$-$C_6$ alkyl; and $R^3$ may be hydrogen or $C_1$-$C_6$ alkyl.

In one embodiment, the compound is of the formula:

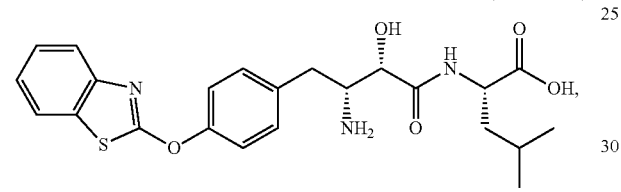

(Formula III)

or a pharmaceutically acceptable salt, ester, hydrate, solvate, prodrug, metabolite, or analog thereof.

The present invention also provides leukotriene inhibitor compounds of the LTA$_4$H inhibitor class useful in the methods and pharmaceutical formulations of the invention of the formula:

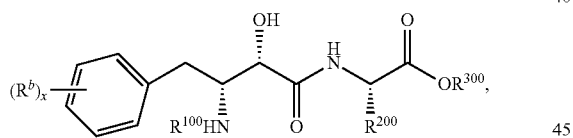

(Formula IV)

or a pharmaceutically acceptable salt, ester, hydrate, solvate, prodrug, metabolite, or analog thereof, where $R^b$ may be groups selected from halogen, $C_1$-$C_6$ alkyl, O—($C_1$-$C_6$ alkyl), $NH_2$, $NH(C_1$-$C_6$ alkyl), $N(C_1$-$C_6$ alkyl)$_2$, $CF_3$, $CF_2H$, and $CFH_2$; $R^{100}$ may be hydrogen or $C(O)OR^c$; $R^c$ may be $C_1$-$C_6$ alkyl; $R^{200}$ may be $C_1$-$C_6$ alkyl; $R^{300}$ may be hydrogen or $C_1$-$C_6$ alkyl; and X may be 0, 1, 2, 3, 4, or 5. A compound of Formula IV is a leukotriene inhibitor.

In one embodiment, the LTA$_4$H inhibitor compound is selected from the group consisting of:

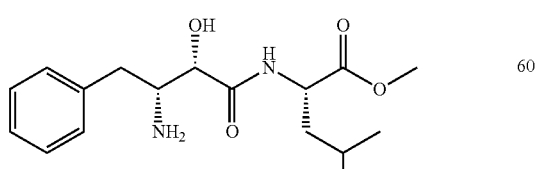

ubenimex methyl ester

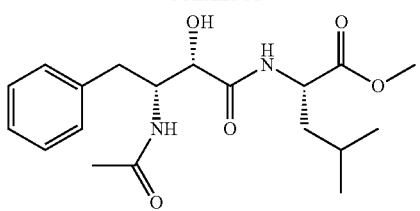

mono-acyl ubenimex

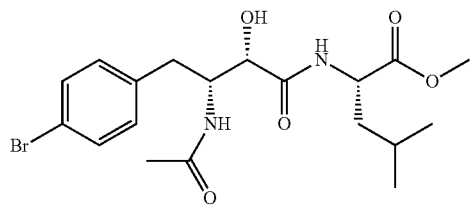

mono-acyl ubenimex bromide

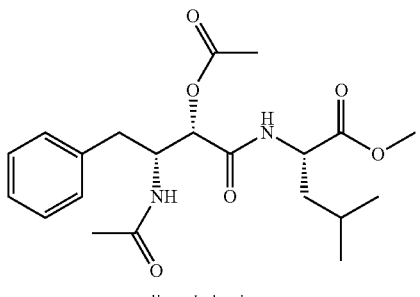

di-acyl ubenimex

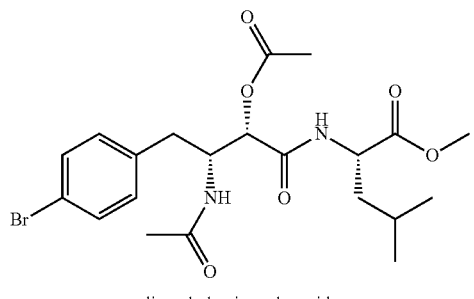

di-acyl ubenimex bromide

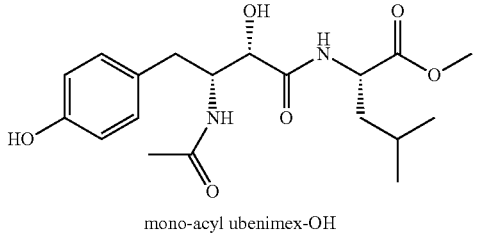

mono-acyl ubenimex-OH

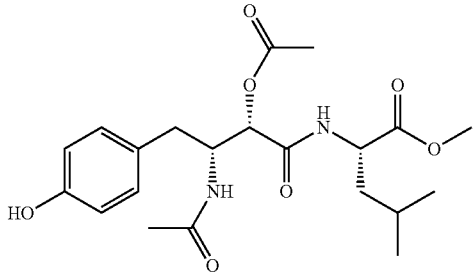

di-acyl ubenimex-OH

The present invention also provides leukotriene inhibitor compounds of the LTA₄H inhibitor class useful in the methods and pharmaceutical formulations of the invention of the formula:

(Formula V)

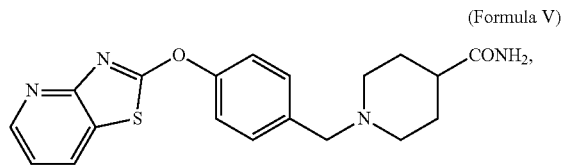 [SMILES: NC(=O)C1CCN(Cc2ccc(Oc3nc4ncccc4s3)cc2)CC1]

having the chemical name, 1-(4-(thiazolo[4,5-b]pyridin-2-yloxy)benzyl)piperidine-4-carboxamide, or a pharmaceutically acceptable salt, ester, hydrate, solvate, prodrug, metabolite, or analog thereof.

The present invention also provides leukotriene inhibitor compounds of the LTA₄H inhibitor class useful in the methods and pharmaceutical formulations of the invention of the formula:

(Formula VI)

having the chemical name, 1-(1-(4-(thiazolo[4,5-b]pyridin-2-yloxy)benzyl)piperidin-4-yl)pyrrolidin-2-one, or a pharmaceutically acceptable salt, ester, hydrate, solvate, prodrug, metabolite, or analog thereof.

The present invention also provides leukotriene inhibitor compounds of the LTA₄H inhibitor class useful in the methods and pharmaceutical formulations of the invention of the formula:

(Formula VII)

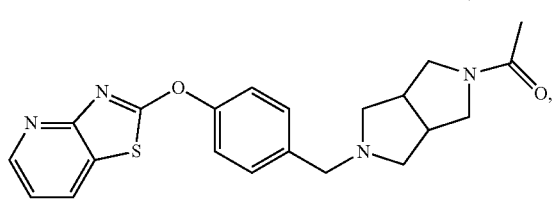

having the chemical name, 1-(5-(4-(thiazolo[4,5-b]pyridin-2-yloxy)benzyl)hexahydropyrrolo[3,4-c]pyrrol-2(1H)-yl)ethanone, or a pharmaceutically acceptable salt, ester, hydrate, solvate, prodrug, metabolite, or analog thereof.

The present invention also provides leukotriene inhibitor compounds of the LTA₄H inhibitor class useful in the methods and pharmaceutical formulations of the invention of the formula:

(Formula VIII)

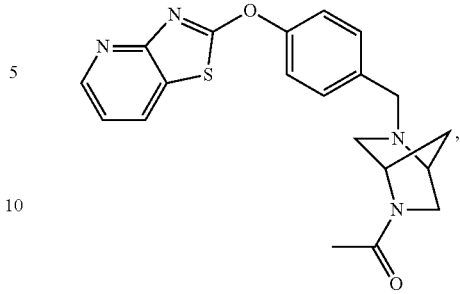

having the chemical name, 1-((1S,4S)-5-(4-(thiazolo[4,5-b]pyridin-2-yloxy)benzyl)-2,5-diazabicyclo[2.2.1]heptan-2-yl)ethanone, or a pharmaceutically acceptable salt, ester, hydrate, solvate, prodrug, metabolite, or analog thereof.

The present invention also provides leukotriene inhibitor compounds of the LTA₄H inhibitor class useful in the methods and pharmaceutical formulations of the invention of the formula:

(Formula IX)

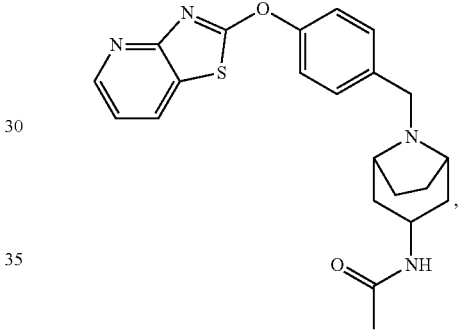

having the chemical name, N-((1R,5S)-8-(4-(thiazolo[4,5-b]pyridin-2-yloxy)benzyl)-8-azabicyclo[3.2.1]octan-3-yl)acetamide, or a pharmaceutically acceptable salt, ester, hydrate, solvate, prodrug, metabolite, or analog thereof.

Compounds of the formulae V-IX and analogs thereof useful in the methods and pharmaceutical compositions of the invention include the LTA₄H inhibitors described in Tanis, V. M. et al. Bioorganic & Medicinal Chemistry Letters, 22 (2012) 7504-7511, the contents of which are incorporated herein by reference.

The present invention also provides methods for treating or preventing PAH by administering to a subject, in need thereof, a therapeutically effective amount of a compound of any of the foregoing formulae. The present invention further provides methods for treating or preventing, and/or for manufacturing a medicament for treating or preventing PAH with a compound of any of the foregoing formulae.

Certain compounds of the invention were identified using in silico methods of the invention to identify compounds with high binding affinity to LTA₄H. In the ligand-based virtual screening, compounds are selected on the basis of known bioactive molecules, and then different 2D/3D methods are performed to identify structure/shape similarity to search for novel compounds. This step can be followed by a pharmacophore matching. The structure-based virtual screening method of the invention can involve a compound selection step in which the compound's predicted affinity with regard to the 3D structure of the target protein is determined, which may be followed by modeling of the ligand position into the binding docket of the target protein, and then scoring or ranking the ligand pose by evaluating the ranks of the ligands regarding their predicted affinities for the target.

In one embodiment, the structure-based design screening method of the invention is used to find and specifically complement the 3D structure (binding and/or active site) of a target protein, for e.g., LTA₄H. In some embodiments subsets of compounds with desired features to complement 3-dimensional shape of the site of the protein, for e.g., LTA₄H, may be selected. From the geometry and functional features of the binding site, complementary structures of a compound (ligand) may be so designed as to have high binding affinity with the target molecule. In one embodiment of the current invention, the screening method involves the AutoDock Vina method.

In one embodiment that includes use of AutoDock Vina, the exhaustivity parameter is set at 20 (more than twice the default value of 8) to cover the possible space as exhaustively as possible.

In silico binding affinity values (for LTA₄H) predicted using this method for certain compounds useful in the invention are as follows ubenimex: −8.6 kcal/mol; compound of Formula III: −11.8 kcal/mol; ubenimex methy ester: −9.2 kcal/mol; mono-acryl ubenimex: −9.4 kcal/mol; mono-acyl ubenimex bromide: −8.7 kcal/mol; di-acyl ubenimex: −9.4 kcal/mol; di-acyl ubenimex bromide: −9.0 kcal/mol; mono-acyl ubenimex-OH: −9.7 kcal/mol; di-acyl ubenimex-OH: −9.9 kcal/mol Table 1 shows these values for other compounds of the invention.

TABLE I

| In silico binding affinities | |
|---|---|
| Compound | Binding Affinity (kcal/mol) |
| 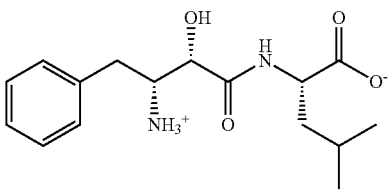 | −9.3 |
| 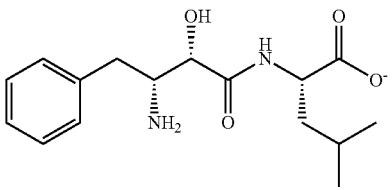 [SMILES: CC(C)C[C@H](NC(=O)[C@@H](O)[C@H]([NH3+])Cc1ccccc1)C(=O)[O-]] | −7.8 |
| 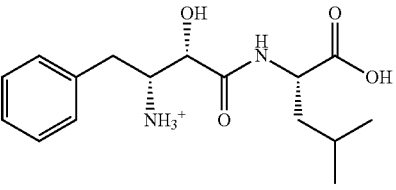 [SMILES: CC(C)C[C@H](NC(=O)[C@@H](O)[C@H]([NH3+])Cc1ccccc1)C(=O)O] | −7.4 |
| 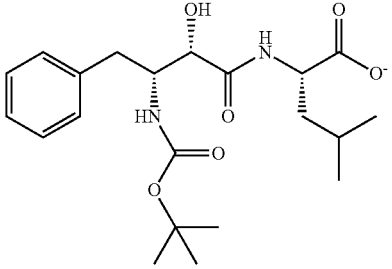 [SMILES: CC(C)C[C@H](NC(=O)[C@@H](O)[C@@H](Cc1ccccc1)NC(=O)OC(C)(C)C)C(=O)[O-]] | −8.1 |
| 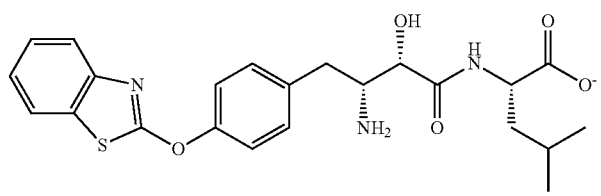 [SMILES: CC(C)C[C@H](NC(=O)[C@@H](O)[C@H](N)Cc1ccc(Oc2nc3ccccc3s2)cc1)C(=O)[O-]] | −11.8 |

TABLE I-continued

In silico binding affinities

| Compound | Binding Affinity (kcal/mol) |
|---|---|
| (structure) | −11.1 |
| (structure) | −8.9 |

The $LTA_4H$ inhibitory activity of certain compounds in this invention was measured using an in vitro epoxide hydrolase activity assay. In this assay, an $LTA_4$ substrate was first prepared from the methyl ester of $LTA_4$ (Cayman Chemical), which was treated under nitrogen with 67 M equivalents of NaOH, at room temperature, for 40 min. The $LTA_4$ substrate in its free acid form was kept frozen at −80° C. until use. Recombinant human $LTA_4H$ (36 ng) was incubated with various concentrations of test compounds for 10 min. at room temperature in assay buffer (0.1 M potassium phosphate, pH 7.4, 5 mg/ml fatty acid-free bovine serum albumin) in a volume of 200 µl. Then, the mixture was incubated with 25 µl of $LTA_4$ substrate (final concentration, 40 ng/ml, 0.13 µM; final volume, 225 µl) for 30 min. at room temperature. The assay was terminated by diluting 20-fold with assay buffer. $LTB_4$ production from each reaction was then assayed using the $LTB_4$ EIA kit (catalog no. 520111, Cayman Chemical). The concentration of compound required for half-maximal inhibition of recombinant enzyme activity ($IC_{50}$) was calculated by nonlinear regression using GraphPad Prism 4.0 (GraphPad Software Inc), one-site binding competition.

$IC_{50}$ values measured from the in vitro epoxide hydrolase activity assay for certain compounds useful in the invention are as follows ubenimex: 101±25 nM; Formula III: 10±5 nM; ubenimex methy ester: 54±13 nM; mono-acryl ubenimex: 94±21 nM; mono-acyl ubenimex bromide: 93±16 nM; di-acyl ubenimex: 25±18 nM; di-acyl ubenimex bromide: 40±22 nM; mono-acyl ubenimex-OH: 13±4 nM; di-acyl ubenimex-OH: 43±11 nM. Certain of these compounds were also used to demonstrate leukotriene inhibitory activity in a rat model of PAH.

The present invention provides in silico methods to identify compounds with high binding affinity to $LTA_4H$ that are useful for treating or preventing PAH. The in silico methods include the following steps: (1) providing compounds known to bind to $LTA_4H$, (2) identifying a candidate compound based on structure or shape similarity to known $LTA_4H$ binding compounds, (3) modeling the candidate compound into a docked position onto the $LTA_4H$ 3D structure, (4) calculating the predicted binding affinity of the candidate compound for $LTA_4H$, and (5) repeating steps 2-4 for different compounds. Optionally, the method further comprises scoring or ranking the candidate compounds based on their predicted affinities for $LTA_4H$. In one embodiment, the predicted binding affinity of a compound selected to have high predicted binding affinity to $LTA_4H$ is −7 kcal/mol or a higher affinity. The in silico methods are used to identify compounds selective for $LTA_4H$, i.e., the compounds have a higher predicted binding affinity for $LTA_4H$ than for another target, such as 5-LO, FLAP, or another protein. The in silico methods further include identifying a compound that inhibits or decreases $LTA_4H$ enzymatic activity. $LTA_4H$ enzymatic activity can be determined, for example, by using an in vitro epoxide hydrolase activity assay. Other assays known in the art can also be used to determine $LTA_4H$ enzymatic activity. $LTA_4H$ enzymatic activity can be measured in terms of IC50 values. A candidate compound for use in the methods of the invention can have an IC50 value of 1000 nM or lower, 500 nM or lower, 200 nM or lower, 100 nM or lower, 75 nM or lower, 50 nM or lower, 25 nM or lower, 10 nM or lower, 5 nM or lower, or 1 nM or lower. In one embodiment, the compounds identified by the in silico methods are used to treat or prevent PAH, or a disorder disclosed herein.

As used herein, a BLT1/BLT2 antagonist is any member of the class of small molecules that inhibits the binding of $LTB_4$ to either or both of its receptors BLT1 and BLT2. While inhibition of the BLT2 may occur with some of these antagonists, in the athymic rat model of PH, blocking BLT1 is the key interaction for efficacy in reversing disease. Thus, in various embodiments, a BLT1/BLT2 antagonist suitable for use in accordance with the invention may only have (or be known only to have) BLT1 antagonist activity.

A BLT1/BLT2 antagonist provided by the instant invention to treat PAH, or other disorders disclosed herein, is LY293111, 2-[2-propyl-3-[3-[2-ethyl-4-(4-fluorophenyl)-5-hydroxyphenoxy]-propoxy]phenoxyl]benzoic acid. LY293111 is a competitive BLT1 antagonist resulting in selective inhibition of the $LTB_4$ pathway, also known as etalocib and VML-295, the structure of which is shown below.

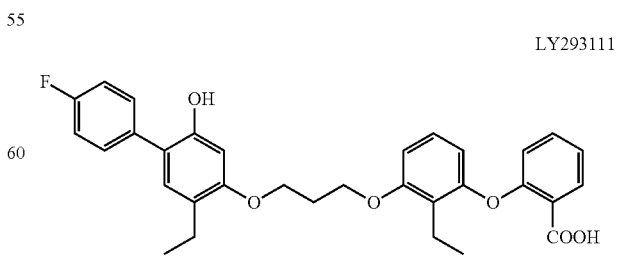

LY293111

LY293111 is an oral agent and is well tolerated. Oral doses of LY293111 generally in the range of 50 mg to 2000 mg per day are administered to a subject in need thereof in accordance with one embodiment of the invention to improve functioning and outcome in the treatment of PAH. In one embodiment, the daily dose is 50 mg. In another embodiment, the daily dose is 500 mg. In another embodiment, the daily dose is 1000 mg. In another embodiment, the daily dose is 1500 mg. In another embodiment, the daily dose is 2000 mg. Thus, depending on the patient, the daily dose can be, for example and without limitation, 50 mg, 100 mg, 200 mg, 300 mg, 400 mg, 500 mg, 600 mg, 700 mg, 800 mg, 900 mg, 1000 mg, 1200 mg, 1500 mg, 1600 mg, 1700 mg, 1800 mg and 2000 mg. Unit dose forms with each of these amounts of LY293111 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

LY293111 analogs useful in the methods and pharmaceutical compositions of the invention include the BLT1/BLT2 antagonist compounds described in Proceedings of the American Society for Clinical Oncology (2002) 21; 1 (ABs 343) (LY293111 for Cancer); SCRIP World Pharmaceutical News 1997, 2272 (13), U.S. Pat. No. 6,235,785, and US Patent Application Publication Nos. 20020013370 and 20020010213, each of which is incorporated herein by reference.

A BLT1/BLT2 antagonist provided by the present invention to treat PAH, or other disorders disclosed herein, is ONO4057, 5-[2-(2-carboxyethyl)-3-[6-(4-methoxyphenyl)-5E-hexenyl]oxyphenoxy]valeric acid, the structure of which is shown below.

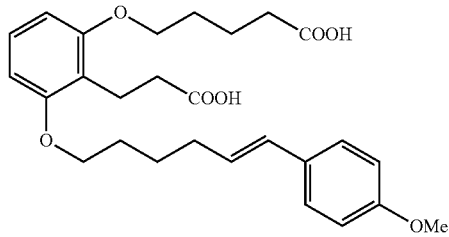 [SMILES: COc1ccc(/C=C/CCCCOc2cccc(OCCCCC(=O)O)c2CCC(=O)O)cc1]

ONO4057 is an orally active competitive BLT1/BLT2 antagonist. Oral doses of ONO4057 generally in the range of 50 mg to 600 mg per day are administered to a subject in need thereof in accordance with one embodiment of the invention to improve functioning and outcome in the treatment of PAH. In one embodiment, the daily dose is 50 mg. In another embodiment, the daily dose is 100 mg. In another embodiment, the daily dose is 300 mg. In another embodiment, the daily dose is 600 mg. Thus, depending on the patient, the daily dose can be, for example and without limitation, 50 mg, 60 mg, 70 mg, 80 mg, 90 mg, 100 mg, 150 mg, 200 mg, 250 mg, 300 mg, 400 mg, 500 mg, and 600 mg. Unit dose forms with each of these amounts of ONO4057 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

ONO4057 analogs useful in the methods and pharmaceutical compositions of the invention include the BLT1/BLT2 antagonist compounds described in European Patent Application Publication No. 405116A and U.S. Pat. No. 5,155,104, incorporated herein by reference.

A BLT1/BLT2 antagonist provided by the present invention to treat PAH, or other disorders disclosed herein, is CP195543, (+)-2-(3-benzyl-4-hydroxy-chroman-7-yl)-4-trifluoromethyl-benzoic acid, the structure of which is shown below.

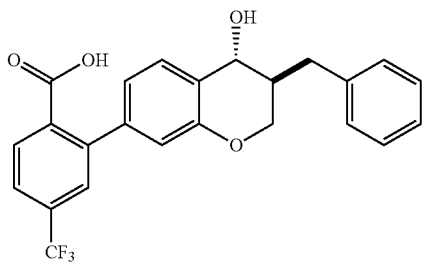

CP-195543

CP195543 is a non-competitive BLT1 antagonist and a competitive antagonist of BLT2. Oral doses of CP195543 generally in the range of 20 mg to 200 mg per day are administered to a subject in need thereof in accordance with one embodiment of the invention to improve functioning and outcome in the treatment of PAH. In one embodiment, CP195543 is administrated in doses of 5 mg four times per day. In another embodiment, CP195543 is administrated 25 mg four times per day. In another embodiment, CP195543 is administrated 50 mg four times per day. Thus, depending on the patient, CP195543 can be administrated, for example and without limitation, 5 mg, 10 mg, 15 mg, 20 mg, 25 mg, 30 mg, 35 mg, 40 mg, 45 mg, and 50 mg four times per day. Unit dose forms with each of these amounts of CP195543 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered four times per day, the present invention provides methods and unit dose forms suitable for other dosing schedules. For example and without limitation, QD, BID, and TID administration can also be used to achieve a beneficial therapeutic effect.

CP195543 analogs useful in the methods and pharmaceutical compositions of the invention include the BLT1/BLT2 antagonist compounds described in U.S. Pat. No. 6,096,906, Journal of Pharmacology and Experimental Therapy, 1998, 285: 945-54, and Goodnow, R. A. et al. J. Med. Chem. 2010, 53, 3502-3516, each of which is incorporated herein by reference.

A BLT1/BLT2 antagonist provided by the present invention to treat PAH, or a disorder disclosed herein, is CGS25019C, 4-(5-(4-(aminoiminomethyl)phenoxy)pentoxy)-3-methoxy-N,N-bis(1-methylethyl) 2-butanedioate, the structure of which is shown below.

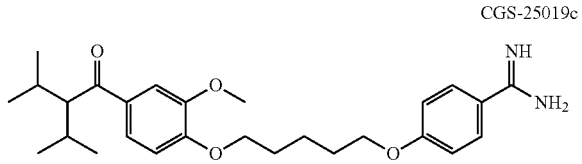 [SMILES: COc1cc(C(=O)C(C(C)C)C(C)C)ccc1OCCCCCOc1ccc(C(=N)N)cc1]

CGS-25019c

CGS25019C, also named LTB019, is a strong BLT1/BLT2 antagonist. Oral doses of CGS25019C generally in the range of 60 mg to 600 mg per day are administered to a subject in need thereof in accordance with one embodiment of the invention to improve functioning and outcome in the treatment of PAH. In one embodiment, the daily dose is 60 mg. In another embodiment, the daily dose is 300 mg. In another embodiment, the daily dose is 600 mg. Thus, depending on the patient, CGS25019C can be administered, for example and without limitation, 60 mg, 120 mg, 180 mg, 240 mg, 300 mg, 360 mg, 420 mg, 480 mg, 540 mg and 600 mg per day. Unit dose forms with each of these amounts of CGS25019C are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

CGS25019C analogs useful in the methods and pharmaceutical compositions of the invention include the BLT1/BLT2 antagonist compounds described in ACS Meeting 1994, 207th; San Diego (MEDI003); International Congress of the Inflammation Research Association 1994; White Haven (Abs W23), each of which is incorporated herein by reference.

A BLT1/BLT2 antagonist provided by the present invention to treat PAH, or a disorder disclosed herein, is Biomed 101, 7-[3-(4-acetyl-3-methoxy-2-propylphenoxy)propoxy]-3,4-dihydro-8-propyl-2H-1-benzopyran-2-carboxylic acid, the structure of which is shown below.

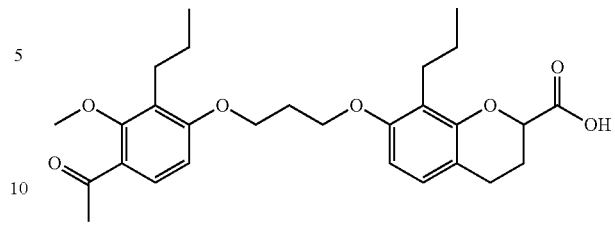

Biomed-101 (SC-41930)

Biomed 101 (also referred to in the scientific literature as SC41930) is a BLT1, BLT2 antagonist. Oral doses of Biomed 101 generally in the range of 25 mg to 300 mg three times per day (TID) are administered to a subject in need thereof in accordance with one embodiment of the invention to improve functioning and outcome in the treatment of PAH. In one embodiment, the daily dose is 25 mg three times per day. In another embodiment, the daily dose is 150 mg three times per day. In another embodiment, the daily dose is 300 mg three times per day. Thus, depending on the patient, Biomed 101 can be administrated, for example and without limitation, 25 mg, 50 mg, 75 mg, 100 mg, 125 mg, 150 mg, 175 mg, 200 mg, 225 mg, 250 mg and 300 mg three times per day. Unit dose forms with each of these amounts of Biomed 101 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered TID, the present invention provides methods and unit dose forms suitable for other dosing schedules. For example and without limitation, QD and BID administration can also be used to achieve a beneficial therapeutic effect.

Biomed 101 analogs useful in the methods and pharmaceutical compositions of the invention include the BLT1/BLT2 antagonist compounds described in U.S. Pat. Nos. 5,532,383; 5,516,917; 5,439,937; 5,310,951; 5,124,350, PCT Patent Application Publication No. WO1995006702 and European Patent Application Publication No. 0593478, U.S. Pat. No. 5,310,951, and Goodnow, R. A. et al. J. Med. Chem. 2010, 53, 3502-3516, each of which is incorporated herein by reference.

A BLT1/BLT2 antagonist provided by the instant invention to treat PAH, or a disorder disclosed herein, is BIIL284BS, ethane; ethyl(NE)-N-[[4-[[3-[[4-[2-(4-hydroxyphenyl)propan-2-yl]phenoxy]methyl]phenyl]methoxy]anilino]methylidene]carbamate, the structure of which is shown below.

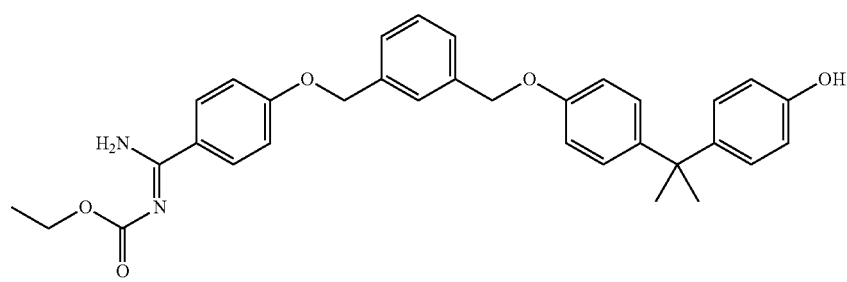

BIIL-284

BIIL284BS (also called Amelubent) is a noncompetitive BLT1/BLT2 antagonist. Oral doses of BIIL284BS generally in the range of 5 mg to 75 mg per day are administered to a subject in need thereof in accordance with one embodiment of the invention to improve functioning and outcome in the treatment of PAH. In one embodiment, the daily dose is 5 mg. In another embodiment, the daily dose is 25 mg per day. In another embodiment, the daily dose is 75 mg per day. Thus, depending on the patient, BIIL284BS can be administered, for example and without limitation, 5 mg, 10 mg, 15 mg, 20 mg, 25 mg, 30 mg, 35 mg, 40 mg, 50 mg, 60 mg, 70 mg and 75 mg per day. Unit dose forms with each of these amounts of BIIL284BS are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

BIIL284BS analogs useful in the methods and pharmaceutical compositions of the invention include the compounds with BLT1/BLT2 antagonist activity described in U.S. Pat. No. 6,576,669, and Goodnow, R. A. et al. J. Med. Chem. 2010, 53, 3502-3516, incorporated herein by reference.

A BLT1/BLT2 antagonist provided by the instant invention to treat PAH, or a disorder disclosed herein, is DW1350, [(E)-N'-hydroxy-4-((5-(4-(5-isopropyl-2-methylthiazol-4-yl)phenoxy)pentyl)oxy)benzimidamide], the structure of which is shown below.

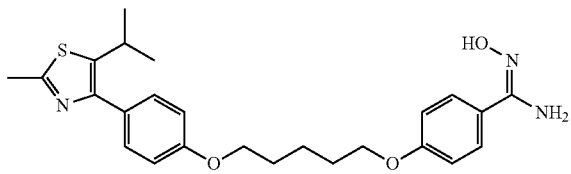 [SMILES: Cc1nc(-c2ccc(OCCCCCOc3ccc(/C(N)=N\O)cc3)cc2)c(C(C)C)s1]

Doses (e.g., oral doses) of DW1350 generally in the range of 5 mg to 2000 mg per day are administered to a subject in need thereof in accordance with one embodiment of the invention to improve functioning and outcome in the treatment of PAH. In one embodiment, the daily dose is 25 mg. In another embodiment, the daily dose is 100 mg per day. In another embodiment, the daily dose is 500 mg per day. Thus, depending on the patient, DW1350 can be administered, for example and without limitation, 5 mg, 10 mg, 20 mg, 25 mg, 30 mg, 35 mg, 40 mg, 50 mg, 75 mg, 100 mg, 200 mg, 300 mg, 400 mg, 500 mg, 600 mg, 700 mg, 800 mg, 900 mg, 1000 mg, 1500 mg, or 2000 mg per day. Unit dose forms with each of these amounts of DW1350 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

DW1350 analogs useful in the methods and pharmaceutical compositions of the invention include the compounds with BLT1/BLT2 antagonist activity described in US 2010/0160394 A1 and Goodnow, R. A. et al. J. Med. Chem. 2010, 53, 3502-3516, the contents of which are incorporated herein by reference.

A BLT1/BLT2 antagonist provided by the instant invention to treat PAH, or a disorder disclosed herein, is LY255283, the structure of which is shown below.

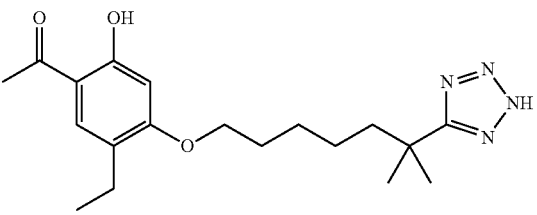

1-(5-ethyl-2-hydroxy-4-((6-methyl-6-(2H-tetrazol-5-yl)heptyl)oxy)phenyl)ethanone Doses (e.g., oral doses) of LY255283 generally in the range of 5 mg to 5000 mg per day are administered to a subject in need thereof in accordance with one embodiment of the invention to improve functioning and outcome in the treatment of PAH. In one embodiment, the daily dose is 50 mg. In another embodiment, the daily dose is 250 mg per day. In another embodiment, the daily dose is 1000 mg per day. In another embodiment, the daily dose is 5000 mg per day. Thus, depending on the patient, LY255283 can be administered, for example and without limitation, 5 mg, 10 mg, 20 mg, 25 mg, 30 mg, 35 mg, 40 mg, 50 mg, 75 mg, 100 mg, 200 mg, 300 mg, 400 mg, 500 mg, 600 mg, 700 mg, 800 mg, 900 mg, 1000 mg, 1500 mg, 2000 mg, 2500 mg, 3000 mg, 4000 mg, or 5000 mg per day. Unit dose forms with each of these amounts of LY255283 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

LY255283 analogs useful in the methods and pharmaceutical compositions of the invention include the compounds with BLT1/BLT2 antagonist activity described in Goodnow, R. A. et al. J. Med. Chem. 2010, 53, 3502-3516, the contents of which are incorporated herein by reference.

The present invention also provides leukotriene inhibitor compounds of the BLT1/BLT2 antagonist class useful in the methods and pharmaceutical formulations of the invention of the formula:

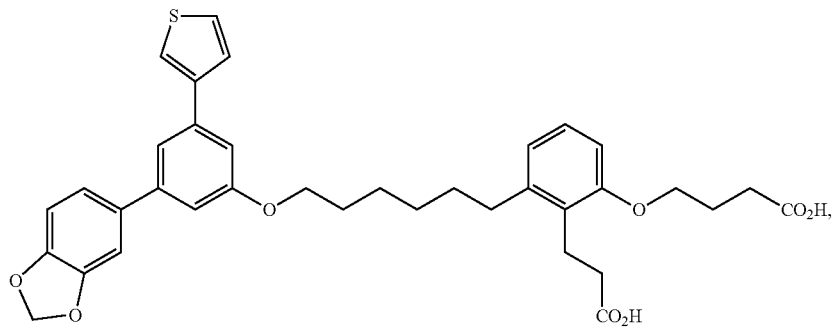

(Formula X)

having the chemical name, 4-(3-(6-(3-(benzo[d][1,3]dioxol-5-yl)-5-(thiophen-3-yl)phenoxy)hexyl)-2-(2-carboxyethyl)phenoxy)butanoic acid, or a pharmaceutically acceptable salt, ester, hydrate, solvate, prodrug, metabolite, or analog thereof.

The present invention also provides leukotriene inhibitor compounds of the BLT1/BLT2 antagonist class useful in the methods and pharmaceutical formulations of the invention of the formula:

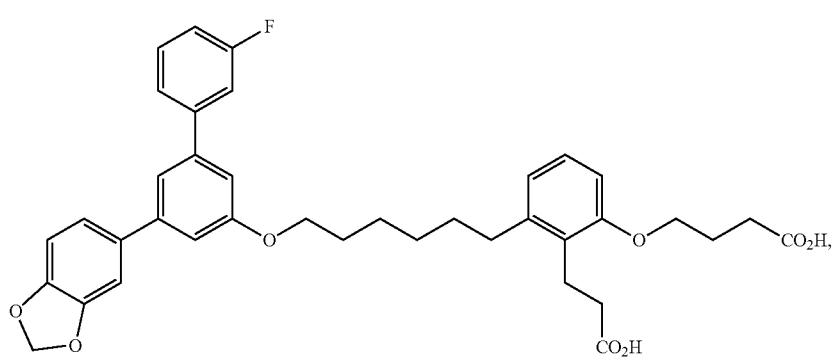

(Formula XI)

having the chemical name, 4-(3-(6-((5-(benzo[d][1,3]dioxol-5-yl)-3'-fluoro-[1,1'-biphenyl]-3-yl)oxy)hexyl)-2-(2-carboxyethyl)phenoxy)butanoic acid, or a pharmaceutically acceptable salt, ester, hydrate, solvate, prodrug, metabolite, or analog thereof.

The present invention also provides methods for treating or preventing PAH, or a disorder disclosed in the present invention, by administering to a subject, in need thereof; a therapeutically effective amount of a compound of any of the foregoing formulae. The present invention further provides methods for treating or preventing, and/or for manufacturing a medicament for treating or preventing PAH with a compound of any of the foregoing formulae.

Compounds of Formulae X-XI and analogs thereof useful in the methods and pharmaceutical compositions of the invention include the compounds with BLT1/BLT2 antagonist activity described in Goodnow, R. A. et al. J. Med. Chem. 2010, 53, 3502-3516, the contents of which are incorporated herein by reference.

Doses (e.g., oral doses) of a BLT1/BLT2 antagonistic compound of any of the foregoing formulae generally in the range of 5 mg to 5000 mg per day are administered to a subject in need thereof in accordance with one embodiment of the invention to improve functioning and outcome in the treatment of PAH, or a disorder disclosed herein. In one embodiment, the daily dose is 50 mg. In another embodiment, the daily dose is 250 mg per day. In another embodiment, the daily dose is 1000 mg per day. In another embodiment, the daily dose is 5000 mg per day. Thus, depending on the patient, a BLT1/BLT2 antagonistic compound of the present invention (e.g., any of the foregoing formulae) can be administrated, for example and without limitation, 5 mg, 10 mg, 20 mg, 25 mg, 30 mg, 35 mg, 40 mg, 50 mg, 75 mg, 100 mg, 200 mg, 300 mg, 400 mg, 500 mg, 600 mg, 700 mg, 800 mg, 900 mg, 1000 mg, 1500 mg, 2000 mg, 2500 mg, 3000 mg, 4000 mg, or 5000 mg per day. Unit dose forms with each of these amounts of a BLT1/BLT2 antagonistic compound of the present invention are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

A 5-LO inhibitor refers to any member of the class of small molecules that block the dioxygenation function of 5-lipoxygenase.

A 5-LO inhibitor provided by the instant invention to treat PAH, or a disorder disclosed herein, is zileuton, 1-[1-(1-benzothiophen-2-yl)ethyl]-1-hydroxyurea, the structure of which is shown below.

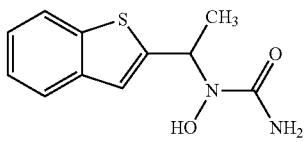 [SMILES: CC(c1cc2ccccc2s1)N(O)C(N)=O]

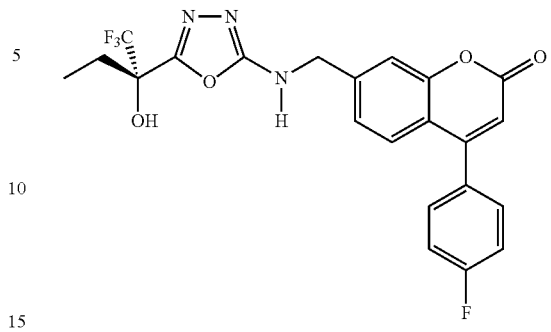

(S)-16

Zileuton is an orally active compound with the brand names ZYFLO® and ZYFLO CR®. Oral doses of zileuton generally in the range of 300 mg to 1200 mg two times per day (BID) are administered to a subject in need thereof in accordance with one embodiment of the invention to improve functioning and outcome in the treatment of PAH. In one embodiment, the daily dose is 300 mg BID. In another embodiment, the daily dose is 600 mg BID. In another embodiment, the daily dose is 1200 mg BID. Thus, depending on the patient, zileuton can be administrated, for example and without limitation, 300 mg, 600 mg, 900 mg and 1200 mg BID. Unit dose forms with each of these amounts of zileuton are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. In various embodiments of the invention, zileuton is administered to a patient not suffering from asthma or chronic myeloid leukemia. Preferably, the subject or patient is a human.

While a daily dose in the range provided above can be conveniently administered BID, the present invention provides methods and unit dose forms suitable for other dosing schedules. For example and without limitation, QD and TID administration can also be used to achieve a beneficial therapeutic effect.

Zileuton analogs useful in the methods and pharmaceutical compositions of the invention include the compounds with 5-LO inhibitory activity described in U.S. Pat. Nos. 7,371,874; 7,368,575; 6,077,850; 6,034,256; 6,028,072; 6,020,347; 6,090,834; 6,191,171; 6,303,612; 6,696,477; 6,753,344; 5,935,990; 5,886,015; 5,783,586; 5,776,932; 5,356,921; 5,714,488; 5,688,822; 5,665,749; 5,665,749; 5,635,514; 5,643,933; 5,532,382; 5,514,703; 5,512,581; 5,403,939; 5,433,997; 5,663,368; 5,696,141; 5,356,921; 5,292,900; 5,616,601; 5,266,705; 5,668,161; 5,229,516; 4,873,259; 4,822,809; PCT Patent Application No. 199534552; European Patent Nos. 0557787; 0888307; 0828718; 0772594; 0772606; and 0765318, each of which is incorporated herein by reference.

A 5-LO or FLAP inhibitor provided by the present invention to treat PAH, or a disorder disclosed herein, is MK0633, 4-(4-Fluorophenyl)-7-[[[5-[(1S)-1-hydroxy-1-(trifluoromethyl)propyl]-1,3,4-oxadiazol-2-yl]amino]methyl]-2H-1-benzopyran-2-one, the structure of which is shown below.

Oral doses of MK0633 (also named Setileuton) generally in the range of 10 mg to 100 mg per day are administered to a subject in need thereof in accordance with one embodiment of the invention to improve functioning and outcome in the treatment of PAH. In one embodiment, the daily dose is 10 mg. In another embodiment, the daily dose is 50 mg per day. In another embodiment, the daily dose is 100 mg per day. Thus, depending on the patient, MK0633 can be administrated, for example and without limitation, 10 mg, 20 mg, 30 mg, 40 mg, 50 mg, 60 mg, 70 mg, 80 mg, 90 mg, and 100 mg per day. Unit dose forms with each of these amounts of MK0633 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. In various embodiments of the invention, MK0633 is administered to a PAH patient not suffering from asthma or COPD. Preferably, the subject or patient is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

MK0633 analogs useful in the methods and pharmaceutical compositions of the invention include the compounds with 5-LO/FLAP inhibitory activity described in PCT Patent Application Publication No. WO1998003484; U.S. Pat. Nos. 5,861,419; 6,001,843; 6,040,450; 6,040,319; 6,071,936; 6,127,545; 6,204,387; 6,252,116 and 6,369,275; and Bioorg Med. Chem. 2012 Jun. 15; 20(12):3728-41, each of which is incorporated herein by reference.

A 5-LO inhibitor provided by the present invention to treat PAH, or a disorder disclosed herein, is ZD2138, 6-((3-Fluoro-5-(4-methoxy-3,4,5,6-tetrahydro-2H-pyran-4-yl)phenoxy) methyl)-1-methylquinol-2-one, the structure of which is shown below.

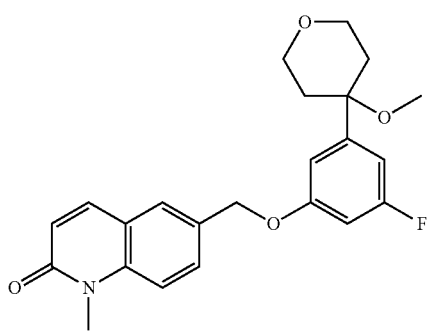 [SMILES: COC1(c2cc(F)cc(OCc3ccc4c(ccc(=O)n4C)c3)c2)CCOCC1]

Oral doses of ZD2138 generally in the range of 25 mg to 400 mg per day are administered to a subject in need thereof in accordance with one embodiment of the invention to improve functioning and outcome in the treatment of PAH. In one embodiment, the daily dose is 25 mg. In another embodiment, the daily dose is 200 mg per day. In another embodiment, the daily dose is 400 mg per day. Thus, depending on the patient, ZD2138 can be administrated, for example and without limitation, 25 mg, 50 mg, 100 mg, 150 mg, 200 mg, 250 mg, 300 mg, 350 mg, and 400 mg per day. Unit dose forms with each of these amounts of ZD2138 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject or patient is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

ZD2138 analogs useful in the methods and pharmaceutical compositions of the invention include compounds with 5-LO inhibitory described in U.S. Pat. Nos. 5,401,751; 5,236,919 and 5,134,148; 5,240,941; and European Patent No. 466452, each of which is incorporated herein by reference.

A 5-LO inhibitor provided by the present invention to treat PAH, or a disorder disclosed herein, is VIA2291, 1-[(2R)-4-[5-[(4-fluorophenyl)methyl]thiophen-2-yl]but-3-yn-2-yl]-1-hydroxyurea, the structure of which is shown below.

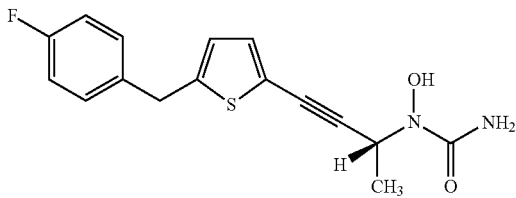 [SMILES: C[C@H](C#Cc1ccc(Cc2ccc(F)cc2)s1)N(O)C(N)=O]

VIA29911, also named Atreleuton or ABT761, can be administered orally QD.

Oral doses of VIA2291 generally in the range of 25 mg to 200 mg per day are administered to a subject in need thereof in accordance with one embodiment of the invention to improve functioning and outcome in the treatment of PAH. In one embodiment, the daily dose is 25 mg. In another embodiment, the daily dose is 100 mg per day. In another embodiment, the daily dose is 200 mg per day. Thus, depending on the patient, VIA2291 can be administrated, for example and without limitation, 25 mg, 50 mg, 75 mg, 100 mg, 125 mg, 150 mg, 175 mg and 200 mg per day. Unit dose forms with each of these amounts of VIA2291 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject or patient is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

VIA2291 analogs useful in the methods and pharmaceutical compositions of the invention include the compounds with 5-LO inhibitory activity described in U.S. Pat. Nos. 7,544,684; 7,470,687; 7,135,471; 5,616,596; 5,516,789; 5,288,751 and 5,288,743, each of which is incorporated herein by reference.

A FLAP inhibitor refers to any compound of the class of small molecules that inhibit the binding of FLAP to AA.

A FLAP inhibitor provided by the present invention to treat PAH, or a disorder disclosed herein, is DG031, (R)-2-[4-(quinolin-2-yl-methoxy)phenyl]-2-cyclopentyl acetic acid, the structure of which is shown below.

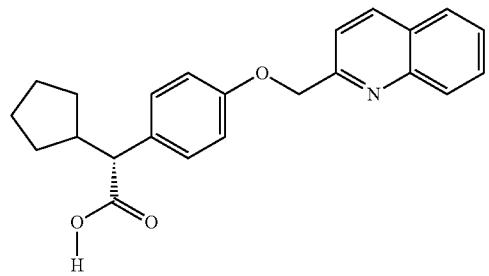 [SMILES: O=C(O)[C@@H](c1ccc(OCc2ccc3ccccc3n2)cc1)C1CCCC1]

Oral doses of DG031 (formerly named BAY X1005 or Veliflapon) generally in the range of 100 mg to 750 mg per day are administered to a subject in need thereof in accordance with one embodiment of the invention to improve functioning and outcome in the treatment of PAH. In one embodiment, the daily dose is 100 mg. In another embodiment, the daily dose is 500 mg. In another embodiment, the daily dose is 750 mg. Thus, depending on the patient, DG031 can be administrated, for example and without limitation, 100 mg, 150 mg, 200 mg, 250 mg, 300 mg, 350 mg, 400 mg, 450 mg, 500 mg, 550 mg, 600 mg, 650 mg, 700 mg and 750 mg per day. Unit dose forms with each of these amounts of DG031 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject or patient is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

DG031 analogs useful in the methods and pharmaceutical compositions of the invention include the compounds with FLAP inhibitor activity described in U.S. Pat. Nos. 5,473,076; 5,306,820 and 4,970,215; European Patent No. 344519; and German Patent No. 19880531, each of which is incorporated herein by reference.

A FLAP inhibitor provided by the present invention to treat PAH, or a disorder disclosed herein, is MK886, 3-[3-butyl-sulfanyl-1-[(4-chlorophenyl)methyl]-5-propan-2-yl-indol-2-yl]-2,2-dimethyl-propanoic acid, the structure of which is shown below.

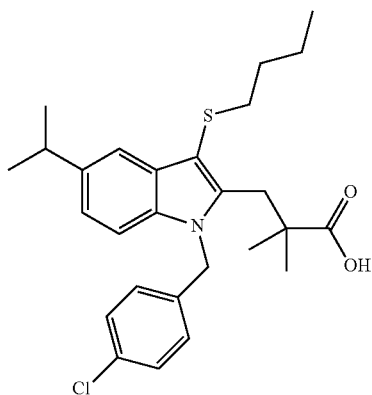 [SMILES: CCCCSc1c(CC(C)(C)C(=O)O)n(Cc2ccc(Cl)cc2)c2ccc(C(C)C)cc12]

MK886, also named as L663536, is well tolerated as an oral formulation in humans. Oral doses of MK886 generally in the range of 100 mg to 750 mg per day are administered to a subject in need thereof in accordance with one embodiment of the invention to improve functioning and outcome in the treatment of PAH. In one embodiment, the daily dose is 100 mg. In another embodiment, the daily dose is 250 mg. In another embodiment, the daily dose is 750 mg. Thus, depending on the patient, MK886 can be administrated, for example and without limitation, 100 mg, 150 mg, 200 mg, 250 mg, 300 mg, 350 mg, 400 mg, 450 mg, 500 mg, 550 mg, 600 mg, 700 mg and 750 mg per day. Unit dose forms with each of these amounts of MK886 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject or patient is a human.

While a daily dose in the range provided above can be conveniently administered QD, the present invention provides methods and unit dose forms suitable for other dosing schedules. For example and without limitation, BID and TID administration can also be used to achieve a beneficial therapeutic effect.

MK886 analogs useful in the methods and pharmaceutical compositions of the invention include the compounds with FLAP inhibitor activity described in U.S. Pat. Nos. 7,629,467 and 5,081,138; US Patent Application Publication Nos. 20110003815; 20100298343; 201000190761; 20100168076; 20100152185; 20090258885; 20090197883; and 20060211677; and European Patent No. 419049, each of which is incorporated herein by reference.

A FLAP inhibitor provided by the present invention to treat PAH, or a disorder disclosed herein, is MK591, 3-[3-tert-butylsulfanyl-1-[(4-chlorophenyl)methyl]-5-(quinolin-2-yl-methoxy)indol-2-yl]-2,2-dimethylpropanoate, the structure of which is shown below.

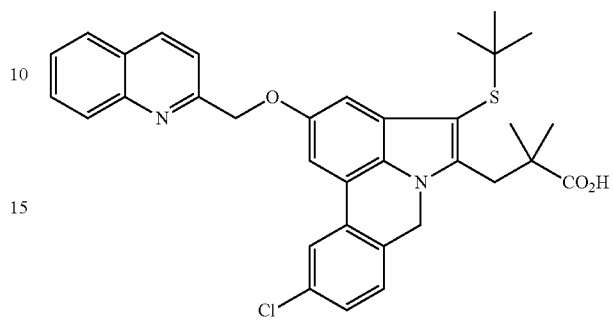

Oral doses of MK591 generally in the range of 12.5 mg to 100 mg two times per day are administered to a subject in need thereof in accordance with one embodiment of the invention to improve functioning and outcome in the treatment of PAH. In one embodiment, the daily dose is 12.5 mg BID. In another embodiment, the daily dose is 50 mg BID. In another embodiment, the daily dose is 100 mg BID. Thus, depending on the patient, MK591 can be administrated, for example and without limitation, 12.5 mg, 25 mg, 37.5 mg, 50 mg, 62.5 mg, 75 mg, 87.5 mg, and 100 mg BID. Unit dose forms with each of these amounts of MK591 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject or patient is a human.

While a daily dose in the range provided above can be conveniently administered BID, the present invention provides methods and unit dose forms suitable for other dosing schedules. For example and without limitation, QD and TID administration can also be used to achieve a beneficial therapeutic effect.

MK591 analogs useful in the methods and pharmaceutical compositions of the invention include the compounds described in European Patent Application No. 419049; U.S. Pat. Nos. 7,563,790; 7,470,687; 7,312,328; 7,141,572; 7,135,471; 7,129,241; 5,459,150; 5,380,850; 5,272,145; 5,254,521; 5,254,567; 5,204,344; and PCT Patent Application Publication Nos. 1994013293A2; 1993010115A1, each of which is incorporated herein by reference.

A method of treating PAH, or a disorder disclosed herein, can include a combination therapy in which a patient in need of treatment is administered a leukotriene inhibitor in combination with one or more drugs approved for the treatment of PAH, for the treatment of a PAH associated condition, or for the treatment of a disorder disclosed herein, or a combination thereof.

Approved drugs currently used in the treatment of PAH in the US or the European Union (EU) include the orally administered PDE-5 inhibitors: sildenafil (Revatio) and tadalafil (Adcirca); the dual endothelin-1A receptor antagonist (ERA): bosentan (Tracleer), ambrisentan (Letairis in US; Volibris internationally). Patients with more advanced disease are often treated with prostacyclins or prostacyclin analogs such as iloprost (Ventavis) or treprostinil (Tyvaso) given as multiple daily inhalations, epoprostenol (Flolan/Veletri) or treprostinil (Remodulin) given as continuous intravenous infusions, or treprostinil also used as a continuous subcutaneous infusion. Intravenous injection of sildenafil is approved for patients who are currently prescribed but are temporarily unable to take oral sildenafil. Inhaled nitric oxide (INOmax) is approved for the neonatal form of PAH—persistent pulmonary hypertension of the newborn (PPHN). Thus, in accordance with the invention, combination therapies of any of these drugs and a leukotriene inhibitor are useful in the treatment of PAH. The following subsections describe combination therapies of particular interest.

Flolan (prostacyclin analog) is considered the most effective of the approved therapies for PAH, but is extremely cumbersome and inconvenient to use (intravenous), and has unique safety concerns. As a result, Flolan is usually reserved for patients with severe functional status or rapidly progressive PAH. Patients must constitute the drug in sterile conditions several times daily. The drug is available as a freeze-dried preparation that needs to be dissolved in alkaline buffer. Because of its short half-life (3-5 min) and stability (8 h at room temperature), Flolan must be maintained in a refrigerated state while given by continuous infusion through a central venous catheter via a portable pump that is worn in a bag around the waist (CADD pump, Smith's Medical MD, St. Paul, Minn.). In 2008, the FDA also approved a new continuous intravenous formulation of epoprostenol that is stable at room temperature for up to 24 h after dilution and may be stored up to 5 days at refrigerator temperature before use (GeneraMedix Inc., Liberty Corner, N.J.). In 2009, GeneraMedix Inc. sold this formulation to Actelion, which began to market the drug (under the brand name Veletri) in April 2010. In late 2010, the Veletri label was expanded to allow preparation of medication up to 7 days at refrigerator temperature or up to 48 h at room temperature in advance of use. Thus, in one embodiment of the invention, a leukotriene inhibitor is administered in combination with epoprostenol, in any of its approved forms, to treat PAH.

Remodulin (continuous subcutaneous infusion form of prostacyclin analog) was not generally used as initial therapy because of its expense, route of delivery, and limited efficacy. In 2004, the FDA and Health Canada approved an intravenous formulation of Remodulin for patients with PAH class II-IV disease who cannot tolerate the subcutaneous form. In early 2006, the FDA expanded the Remodulin label to include patients requiring transition from Flolan. In 2009, United Therapeutics received FDA approval for an inhaled formulation of treprostinil (Tyvaso). Thus, in one embodiment of the invention, a leukotriene inhibitor is administered in combination with treprostinil to treat PAH.

Ventavis (iloprost), a prostacyclin analogue administered via inhalation is also marketed in several member countries of the EU as Ilomedine as an intravenous formulation. The label for inhaled iloprost in the EU is restricted to patients with idiopathic PAH and functional class III symptoms. In contrast, the label in the US is broader: patients with PAH (regardless of etiology) and class III or IV symptoms. It is required 6 to 9 times a day administration. Thus, in one embodiment of the invention, a leukotriene inhibitor is administered in combination with iloprost, in any of its approved forms, to treat PAH.

In 2001, the nonselective ERA Tracleer (bosentan) became the first oral PAH therapy and was available only through a special centralized access program in the US because of its significant risk of (reversible) liver injury, teratogenicity, testicular atrophy, and male sterility. Treatment with Tracleer consists of an initial dosage of 62.5 mg twice daily for 4 weeks, followed by a maintenance dose of 125 mg twice daily. Tracleer was initially indicated for patients with PAH and moderate or severe functional status (WHO class III, IV). In 2008 (EU) and 2009 (US), the label was expanded to patients with mild symptoms (functional class II). Thus, in one embodiment of the invention, a leukotriene inhibitor is administered in combination with bosentan, in any of its approved forms, to treat PAH.

Ambrisentan is the oral selective ERA-receptor antagonist marketed by Gilead Sciences in the US (Letairis) and by GlaxoSmithKline in other regions (Volibris) for the once-daily treatment of patients with WHO class II or III symptoms to improve exercise capacity and delay clinical worsening. As with bosentan, ambrisentan has class effects of teratogenicity, testicular injury, reduced male fertility, and anemia. Thus, in one embodiment of the invention, a leukotriene inhibitor is administered in combination with ambrisentan, in any of its approved forms, to treat PAH.

The oral PDE-5 inhibitor Revatio (sildenafil) was approved in the US for the treatment of PAH (WHO Group I) to improve exercise ability and delay of clinical worsening at a dose of 20 mg three times daily, regardless of functional class or etiology. The EU label is restricted to improvement of exercise capacity in patients with PAH, which is either idiopathic or associated with collagen vascular disease and with functional class III status. In 2009, the FDA approved an intravenous form of Revatio given as an injection (10 mg 3-times a day) for a patient unable to take the oral formulation. In May 2010, the EU approved Revatio as an oral suspension (compounded from 20 mg tablets) for the treatment of pediatric patient aged 1 to 17 years with PAH. Thus, in one embodiment of the invention, a leukotriene inhibitor is administered in combination with sildenafil, in any of its approved forms, to treat PAH.

The oral PDE-5 inhibitor Adcirca (tadalafil) 40 mg once daily is indicated in the US to improve exercise ability in patients with PAH (WHO Group I) regardless of etiology or functional class (Packet Insert). The EU label is restricted to patients with functional class II and III status. Tadalafil has a long half-life (35 h) in patients with PAH (US Packet Insert) has also shown benefit in patients with PAH on concomitant bosentan.

Thus, the method of treating the patient may involve administering at least one additional active agent, i.e., in addition to the leukotriene inhibitor. The additional active agent may be, for example, a vasodilator such as prostacyclin, epoprostenol, and sildenafil; an endothelin receptor antagonist such as bosentan; a calcium channel blocker such as amlodipine, diltiazem, and nifedipine; an anticoagulant such as warfarin; a diuretic, a prostanoid (e.g., prostacyclin or $PGI_2$), drugs for treating diseases associated with overactive B cells or dysfunctional B cells such as Rituximab, and/or a Type V phosphodiesterase (PDE5) inhibitor.

When the method of the invention involves combination therapy, i.e., wherein a secondary agent such as a vasodilator is co-administered with a leukotriene inhibitor, the agents may be administered separately, at the same, or at different times of the day, or they may be administered in a single composition. Thus, the present invention provides novel pharmaceutical formulations in which a leukotriene inhibitor is combined with one of the active agents discussed above and unit dose forms of those formulations.

In the combination therapies of the invention, each agent can be administered in an "immediate release" manner or in a "controlled release manner." When the additional active agent is a vasodilator, for instance, any dosage form containing both active agents, i.e., both the leukotriene inhibitor and the vasodilator, can provide for immediate release or controlled release of the vasodilator, and either immediate release or controlled release of the leukotriene inhibitor.

As a general example, a combination dosage form of the invention for once-daily administration might contain in the range of about 25 mg to about 400 mg of a leukotriene inhibitor, i.e. about 30 mg to about 250 mg of a leukotriene inhibitor, or i.e. about 50 mg to about 180 mg of a compound of leukotriene inhibitor, in a controlled release (e.g., sustained release) or immediate release form, and either sildenafil in immediate release form, or in controlled release form, with the additional active agent present in an amount that provides a weight ratio of the leukotriene inhibitor to sildenafil, or a weight ratio of the leukotriene inhibitor to sildenafil, specified as above. In other formulations of the invention, two or more additional active agents, which may or may not be in the same class of drug (e.g., vasodilators), can be present in combination, along with the leukotriene inhibitor. In such a case, the effective amount of either or each individual additional active agent present will generally be reduced relative to the amount that would be required if only a single added agent were used.

The additional active agent may also be, as discussed above, a Type V phosphodiesterase inhibitor, administered with a leukotriene inhibitor, or with both the leukotriene inhibitor and a vasodilator. Examples of Type V phosphodiesterase inhibitors include, without limitation, avanafil, sildenafil, tadalafil, zaprinast, dipyridamole, vardenafil and acid addition or other pharmaceutically acceptable salts thereof. Sildenafil is an excellent example. In an exemplary embodiment, the leukotriene inhibitor is co-administered with a Type V phosphodiesterase inhibitor selected from the group consisting of avanafil, tadalafil, and sildenafil, and the daily dose of a compound of the leukotriene inhibitor is as given above for the monotherapeutic regimen.

The additional active agent may also be, as discussed above, an endothelin receptor antagonist, e.g., bosentan, sitaxsentan, or ambrisentan, with bosentan being an exemplary active agent.

A pharmaceutical composition of the invention is a pharmaceutical formulation containing an active agent formulated in a manner compatible with its intended route of administration. A variety of routes are contemplated, including but not limited to, oral, pulmonary, inhalational, sublingual, intranasal, parenteral, intradermal, transdermal, topical, transmucosal, subcutaneous, intravenous, intramuscular, intraperitoneal, buccal, rectal, and the like. The term "parenteral" as used herein is intended to include subcutaneous, intravenous, and intramuscular injection.

Generally, pharmaceutical formulations of the invention are prepared for oral administration and in an immediate release form suitable for once per day (QD) administration. Certain formulations are suitable for intranasal administration to a patient.

Certain pharmaceutical formulations of the invention comprise a leukotriene inhibitor or a salt thereof and one or more pharmaceutically acceptable (approved by a state or federal regulatory agency for use in humans, or is listed in the U.S. Pharmacopia, the European Pharmacopia) excipients or carriers. The term excipient or carrier as used herein broadly refers to a biologically inactive substance used in combination with the active agents of the formulation. An excipient can be used, for example, as a solubilizing agent, a stabilizing agent, a diluent, an inert carrier, a preservative, a binder, a disintegrant, a coating agent, a flavoring agent, or a coloring agent. Preferably, at least one excipient is chosen to provide one or more beneficial physical properties to the formulation, such as increased stability and/or solubility of the active agent(s). Ubenimex or a salt thereof as described herein is an exemplary active agent suitable for use in the formulations of the present invention.

Examples of suitable excipients include certain inert proteins such as albumins; hydrophilic polymers such as polyvinylpyrrolidone; amino acids such as aspartic acid (which may alternatively be referred to as aspartate), glutamic acid (which may alternatively be referred to as glutamate), lysine, arginine, glycine, and histidine; fatty acids and phospholipids such as alkyl sulfonates and caprylate; surfactants such as sodium dodecyl sulphate and polysorbate; nonionic surfactants such as such as TWEEN®, PLURONIC®, or polyethylene glycol (PEG); carbohydrates such as glucose, sucrose, mannose, maltose, trehalose, and dextrins, including cyclodextrins; polyols such as mannitol and sorbitol; chelating agents such as EDTA; and salt-forming counter-ions such as sodium.

Solutions or suspensions used for the delivery can include the following components: a sterile diluent such as water for injection, saline solution, fixed oils, polyethylene glycols, glycerine, propylene glycol, polysorbate, tocopherol polyethylene glycol succinate (TPGS), or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. These preparations can be enclosed in ampoules, disposable syringes or multiple dose vials made of glass or plastic.

In some embodiments, the pharmaceutical formulations of the present invention contain a plurality of liposomes or microparticles comprising the leukotriene inhibitor active agent. In various embodiments, the pharmaceutical formulation of the leukotriene inhibitor is a powder comprising solid particles (e.g., liposomes or microparticles) suitable for administration via inhalation. The solid particles comprise the active agent, a carrier, optionally a surfactant, and optionally additional recipients. The powder may be prepared by the methods described in the Examples below, or by any convenient method. An example of a preparatory method is spray drying a solution containing the active agent (and other components) onto a powder comprising the carrier compound. Another example is freeze drying a solution comprising all of the components of the final powder.

Suitable liposomes for use in the present formulations of the invention are known in the art. For example, suitable liposomes include cholesterol, 1,2-distearoyl-sn-glycero-3-phosphocholine (DSPC) and PEG-DSPE, with the weight ratio being about 5:10:1. In some embodiments, the liposome formulation comprises about 0.1-25%, e.g., 0.1%, 1%, 5%, 10% or 20% (w/w) of a phospholipid, such as dipalmitoylphosphatidylcholine (DPPC) and 1,2-distearoyl-sn-glycero-3-phosphocholine (DSPC). In some embodiments, the liposome formulation comprises about 0.5-20%, e.g., 1%, 5%, or 10% (w/w) of a hydrophilic polymer, such as polyvinylpyrrolidone (PVP). In some embodiments, the liposome formulation comprises about 10-35% of an amino acid, such as L-leucine.

Suitable microparticles for use in the formulations of the invention are known in the art. For example, microparticles are formed of one or more hydrophilic polymers such as polyvinylpyrrolidone (e.g., PVP-10), polyvinyl alcohol (e.g., PVA-30), polyvinyl acetate, or Poloxamer (e.g., Poloxamer-188). In some embodiments, the microparticle formulation comprises about 70-85 wt % of polyvinyl alcohol (e.g., PVA- 30), about 5-15% PVP (e.g., PVP-10), 1-5% Poloxamer (e.g., Poloxamer-188), 0-10% L-leucine, and about 0.5-10% of a leukotriene inhibitor compound (e.g., 5%). In some embodiments, the formulation is suitable for administration via the respiratory tract.

The pharmaceutical formulations of a leukotriene inhibitor useful in the methods of the invention can be prepared as a liquid or in a solid form such as a powder, tablet, pill or capsule for oral administration. Liquid formulations of the invention may take such forms as suspensions, solutions or emulsions in oily or aqueous vehicles, and may contain formulatory agents such as suspending, stabilizing and/or dispersing agents. In one embodiment, the formulation is an aqueous solution. In another embodiment, the final formulation is lyophilized.

In various embodiments, the formulations of the invention comprise a leukotriene inhibitor at a concentration of from 0.25 wt % to 100 wt %, or from 0.25 wt % to 50 wt %, or from 0.8 wt % to 25 wt %, or from 1 wt % to 10%, or from 1.5 wt % to 5 wt %. In certain embodiments, a leukotriene inhibitor compound is formulated at a concentration of from about 0.5 wt % to about 5 wt %. In certain embodiments, a leukotriene inhibitor compound is formulated at a concentration of about 0.25 wt % to about 10 wt %.

The present invention also provides a pharmaceutical pack or kit comprising one or more containers filled with a solid or liquid formulation of a leukotriene inhibitor. In a particular embodiment, the formulation is a powder formulation of a leukotriene inhibitor. In various embodiments, a leukotriene inhibitor is formulated at a concentration of at least about 0.5 wt % and the formulation is suitable for delivery via inhalation to a human.

The present invention also provides for a use of a formulation of a leukotriene inhibitor in the manufacture of a medicament for treating PAH, or a disorder disclosed herein, in a subject in need thereof. Generally, the pharmaceutical formulation is sterile.

Generally, the dosage forms, e.g., an inhalable dosage form, provide for sustained release, i.e., gradual, release of a compound of the current invention, for e.g., a leukotriene inhibitor, from the dosage form to the patient's body over an extended time period, typically providing for a substantially constant blood level of the agent over a time period in the range of about 4 to about 12 hours, typically in the range of about 6 to about 10 hours. In a particularly preferred embodiment, there is a very gradual increase in blood level of the drug following nasal administration of the dosage form containing a compound of the current invention, for e.g., a leukotriene inhibitor, such that peak blood level is not reached until at least 4-6 hours have elapsed, with the rate of increase of blood level drug approximately linear. In addition, in the preferred embodiment, there is an equally gradual decrease in blood level at the end of the sustained release period.

Although the pharmaceutical compositions of the invention are preferably formulated for inhalation, e.g., as a solution in saline, as a dry powder, or as an aerosol, other modes of administration are suitable as well. For example, administration may be sublingual, oral, parenteral, transdermal, via an implanted depot, transmucosal, e.g., rectal or vaginal, preferably using a suppository that contains, in addition to the active agent, excipients such as a suppository wax. Transmucosal administration also encompasses transurethral administration, as described, for example, in U.S. Pat. Nos. 5,242,391; 5,474,535 and 5,773,020 to Place et al.

Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in *Remington: The Science and Practice of Pharmacy* (Easton, Pa.: Mack Publishing Co., 1995). For those compounds that are orally active, oral dosage forms are generally preferred, and include tablets, capsules, caplets, solutions, suspensions and syrups, and may also comprise a plurality of granules, beads, powders, or pellets that may or may not be encapsulated. Preferred oral dosage forms are tablets and capsules.

In embodiments, it may be especially advantageous to formulate compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, e.g., two tablets or capsules taken together may provide a therapeutically effective dosage of a leukotriene inhibitor, such that the unit dosage in each tablet or capsule is approximately 50% of the therapeutically effective amount.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like.

Capsules are another oral dosage forms for those compounds of the current invention, for e.g., leukotriene inhibitors, that are orally active, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, cited earlier herein, which describes materials and methods for preparing encapsulated pharmaceuticals.

Oral dosage forms, whether tablets, capsules, caplets, or particulates, if desired, may be formulated so as to provide for controlled release of the compounds of the current invention, for e.g., leukotriene inhibitors, and in a preferred embodiment, the present formulations are controlled release oral dosage forms.

Generally, as will be appreciated by those of ordinary skill in the art, sustained release dosage forms are formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example:

cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The active agent may also be administered through the skin using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition to the formulations described previously, the active agent may be formulated as a depot preparation for controlled release of the active agent, preferably sustained release over an extended time period. These sustained release dosage forms are generally administered by implantation (e.g., subcutaneously or intramuscularly or by intramuscular injection).

Certain compounds or active agents of the present invention are capable of further forming salts. All of these forms are also contemplated within the scope of the claimed invention.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

Certain compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

In yet another aspect, the present invention provides a pharmaceutical composition comprising 0.5%-50%, 0.5%-25%, or 0.5%-10% ubenimex and a pharmaceutically acceptable carrier. In one embodiment, the composition is suitable for inhalation. In one embodiment, the composition is an inhalable formulation used for treating PAH, or a disorder disclosed herein.

In still another aspect, the present disclosure provides a pharmaceutical composition comprising ubenimex and a plurality of particles, wherein the plurality of particles is a plurality of liposomes comprising 1,2-distearoyl-sn-glycero-3-phosphoethanolamine-N-[amino(polyethylene glycol)] (PEG-DSPE) or a plurality of microparticles comprising a hydrophilic polymer. In one embodiment, the composition is suitable for inhalation. In one embodiment, the composition is an inhalable formulation used for treating PAH, or a disorder disclosed herein.

The present disclosure also provides a pharmaceutical formulation comprising ubenimex and a vasodilator. In one embodiment, the formulation is an inhalable dosage form. In one embodiment, the vasodilator is selected from sildenafil, avanafil, tadalafil, zaprinast, dipyridamole, vardenafil, bosentan, and pharmaceutically acceptable salts thereof. In one embodiment, the formulation is an inhalable formulation used for treating PAH, or a disorder disclosed herein.

The discovery that $LTB_4$ directly induces pulmonary arterial endothelial cell apoptosis and pulmonary arterial smooth muscle cell proliferation and hypertrophy is highly novel and relevant to other diseases in which inflammation is associated with vascular destruction. Thus, in accordance with the invention, methods for treating such diseases by administering therapeutically effective doses of a leukotriene inhibitor as described herein are provided. Activation of the 5-LO system within the vascular bed requires the presence of several types of cells with distinct cross-talk capabilities. Vascular inflammation with leukocytes (notably macrophages, neutrophils, and mast cells) are an important source of secreted $LTB_4$, alternatively, these cells can secrete $LTA_4$ that can be utilized by endothelial cells and smooth muscle cells to produce $LTB_4$ (i.e., transcellular biosynthesis). Antagonizing $LTB_4$ activity with a specific view to limiting endothelial cell death and smooth muscle cell proliferation and hypertrophy is of particular relevance to treatment of vascular disease characterized by endothelial cell apoptosis and smooth muscle cell obliterative proliferation. Such diseases include the following.

Coronary artery disease (CAD) is a common life-threatening disease that is associated with increased endothelial cell apoptosis (e.g., Ferrari et al., *Cardiovasc Drugs Ther* (2010) 24:331-339), and $LTB_4$ biosynthesis has been recently implicated in the development of this condition (Hartiale et al, *Hum Genet* (2011) 129:617-627). Therapies which inhibit $LTB_4$ action can limit CAD development by preventing coronary artery endothelial apoptosis. Thus, in one embodiment, the present invention provides methods for preventing and treating CAD by administering a therapeutically effective dose of a leukotriene inhibitor. Generally, the therapeutically effective dose is substantially similar to those described herein for the treatment of PAH.

Non-CAD atherosclerotic conditions including peripheral vascular disease (PVD), aortic atherosclerosis, and cerebral arteriosclerosis.

Beyond CAD, all forms of atherosclerosis involve endothelial cell apoptosis. The vascular inflammation, associated with these arteriopathies demonstrates evidence of $LTB_4$ pathway activation (e.g., Stanke-Labesque et al. *J Lipid Res* (2012) 53:1944-51). $LTB_4$ antagonism can benefit these conditions. Thus, in one embodiment, the present invention provides methods for preventing and treating non-CAD atherosclerotic conditions by administering a therapeutically effective dose of a leukotriene inhibitor. Generally, the therapeutically effective dose is substantially similar to those described herein for the treatment of PAH.

Diabetic retinopathy: A recent study has demonstrated that leukocytes regulate retinal capillary degeneration in diabetic animals via the generation of leukotrienes (Talahalli et al. *J Leuk Biol* (2012) epub ahead of print Oct. 29, 2012). In light of the present invention, this study implicates $LTB_4$ in the development of this debilitating condition associated with diabetes, currently a disease without good therapeutic targets. Limiting vascular injury (specifically endothelial apoptosis) with $LTB_4$ antagonists can ameliorate this condition. Thus, in one embodiment, the present invention provides methods for preventing and treating diabetic retinopathy by administering a therapeutically effective dose of a leukotriene inhibitor. Generally, the therapeutically effective dose is substantially similar to those described herein for the treatment of PAH.

Ischemia-reperfusion injury: Ischemia-reperfusion can cause organ damage in circumstances when blood flow is interrupted then restored (such as in the case of solid organ transplantation). This condition is associated with endothelial cell apoptosis (e.g., Fischer et al. *Am J Respir Crit. Care Med* (2000) 162:1932-1939) and elevated $LTB_4$ (e.g., Cicco et al. *Adv Exp Med Biol* (2005) 363-73). Blocking $LTB_4$ production or signaling during known periods of ischemia-reperfusion, such as transplantation, can limit widespread endothelial injury and subsequent organ dysfunction. Thus, in one embodiment, the present invention provides methods for preventing and treating ischemia-reperfusion injury by administering a therapeutically effective dose of a leukotriene inhibitor. Generally, the therapeutically effective dose is substantially similar to those described herein for the treatment of PAH.

Emphysema: Emphysema is a disease that involves inappropriate endothelial cell apoptosis (e.g., Kashahara et al, *Am J Respir Crit. Care Med* (2001) 163: 737-744), and $LTB_4$ has been demonstrated to have importance in the pathogenesis of pulmonary emphysema associated with pulmonary inflammation (Shim et al., *Am J Physiol Lung Cell Mol Physiol* (2010) L749-59). Blocking $LTB_4$ synthesis or signaling in patients at risk for, or who have already have, emphysema can limit disease progression through the prevention of $LTB_4$-mediated endothelial apoptosis. Thus, in one embodiment, the present invention provides methods for preventing and treating emphysema by administering a therapeutically effective dose of a leukotriene inhibitor. Generally, the therapeutically effective dose is substantially similar to those described herein for the treatment of PAH.

Radiation-induced organ and tissue injury: Cancer therapy often includes multimodalities ranging from surgery to chemotherapy to radiation. Endothelial cells are particularly sensitive to radiation-mediated injury and apoptosis (e.g., Paris et al, *Science* (2003) 293:293-297). While radiation clearly induces inflammation, $LTB_4$ has yet to be well-quantified in this disease state. When elevated, $LTB_4$ will participate in organ injury by worsening endothelial cell apoptosis. Anti-$LTB_4$ therapies of the present invention, co-administered with radiation therapy, can limit radiation-induced organ injury in this case. Thus, in one embodiment, the present invention provides a method for preventing radiation-induced organ and tissue injury by administering a therapeutically effective dose of a leukotriene inhibitor. Generally, the therapeutically effective dose is substantially similar to those described herein for the treatment of PAH.

Corpus Luteum Regression: The ovarian follicle has the capacity for rapid microvascular development and regression; the latter process requires significant endothelial apoptosis. $LTB_4$ biosynthesis has been suggested to be involved in normal luteal function (Hattori et al, *Mol Hum Reprod* (1998) 4: 803-810). $LTB_4$ produced locally in the corpus luteum has also been suggested to be an important regulator in human luteal regression (Yoshimura et al, *Acta Endocrinol* (1992): 127:246-51). In accordance with the present invention, inhibition of $LTB_4$ can treat conditions involving abnormal corpus luteum function. Thus, in one embodiment, the present invention provides a method for treating corpus luteum regression (and methods for preventing it in patients susceptible to it) by administering a therapeutically effective dose of a leukotriene inhibitor. Generally, the therapeutically effective dose is substantially similar to those described herein for the treatment of PAH.

The present invention also provides methods for preventing and treating immune dysregulation, such as an autoimmune disease. In one embodiment, the autoimmune disease is scleroderma, including but not limited to scleroderma interstitial lung disease (SLD) and systemic sclerosis. Excessive fibrosis and inflammatory cell infiltration are the main histologic features of SLD. Leukotrienes and lipoxins are two functionally different classes of lipoxygenase-derived eicosanoids. Leukotrienes are potent proinflammatory mediators and directly and indirectly stimulate fibroblast chemotaxis, proliferation, and collagen synthesis. Lipoxins counter-regulate the proinflammatory actions of leukotrienes and activate resolution of the inflammatory response. In addition, lipoxins inhibit growth-factor-induced fibroblast proliferation and collagen synthesis. The compounds of the current invention are useful for pharmacologic correction of a leukotriene-lipoxin imbalance for treating of SLD. In another embodiment, the autoimmune disease is systemic lupus erythematosus (SLE). Thus, in various embodiments, the present invention provides methods for treating SLD, systemic sclerosis, and SLE (and methods for preventing such diseases in patients susceptible to them) by administering a therapeutically effective dose of a leukotriene inhibitor. Generally, the therapeutically effective dose is substantially similar to those described herein for the treatment of PAH.

In any of these methods of the invention, the patient may further be suffering from PAH. Further, and regardless of whether the patient is suffering from PAH, the leukotriene inhibitor can be administered alone or in combination with one or more additional active agents approved for treatment of the non-PAH condition.

The present invention further provides method for determining whether a patient is in need of treatment with a therapy of the invention, whether a patient is likely to respond to such a therapy, or whether a therapy of the invention is preventing or treating disease. In a variety of embodiments of these methods, the patient is a patient at risk of getting or already diagnosed as having PAH; however, these methods are equally applicable to the other diseases that can be treated in accordance with the methods and compositions of the invention.

A method of determining whether a patient is in need of treatment with or likely to respond to a therapy of the invention includes providing a biological sample obtained from the patient. Then, the level of LTB4 is determined in the biological sample. A control level of LTB4 is also determined from a biological sample of an individual not suffering from a disorder disclosed in the present invention (e.g., PAH) or from the patient prior to diagnosis of a disorder disclosed in the present invention (e.g., PAH). The level of LTB4 from the patient is then compared to the control LTB4 level. If the level of LTB4 in the patient is higher than (or elevated compared to) the control LTB4 level, the patient is in need of treatment with or likely to respond to a therapy of the invention. The method further comprises administering an effective amount of a $LTA_4H$ inhibitor of the invention to the patient, thereby treating or preventing PAH, or a disorder disclosed in the invention, in the patient.

The biological sample can be obtained from the breath, sputum, tissue, plasma, serum, or urine of the patient or the individual not suffering from pulmonary arterial hypertension, or a disorder disclosed in the present invention. In some patients, the evidence of increased $LTB_4$ may only be detected in one body compartment (e.g., sputum or breath) and not detected in other compartments (e.g., serum). For example, a higher or elevated level of LTB4 of at least 2-fold higher, at least 3-fold higher, at least 4-fold higher, or at least 5-fold higher than the control value indicates that the patient is in need of treatment using a therapy of the invention or that the patient is likely to respond to a therapy of the invention. For example, the control LTB4 level is 600 pg/mL or less, 500 pg/mL or less, 400 pg/mL or less, 300 pg/mL or less, 200 pg/mL, or 100 pg/mL or less. The control LTB4 level can also be 30 pg/mg or less, 20 pg/mg or less, 10 pg/mg or less, 7.5 pg/mg or less, or 5 pg/mg or less. For example, the elevated level of leukotriene B4 is 100 pg/mL or higher, 200 pg/mL or higher, 300 pg/mL or higher, 400 pg/mL or higher, 500 pg/mL or higher, 600 pg/mL or higher, or 1000 pg/mL or higher. The elevated level of LTB4 can also be 40 pg/mg of tissue or higher, 30 pg/mg of tissue or higher, 20 pg/mg of tissue of higher, 10 pg/mg of tissue or higher, 7.5 pg/mg of tissue or higher, or 5 pg/mg of tissue or higher.

Standard methods for assessing $LTB_4$ levels are utilized. Additionally, new methods for assessing $LTB_4$ are provided, wherein leukotriene levels are assessed in PAH patients to provide a rapid non-invasive evaluation of pulmonary inflammation.

The instant invention includes methods of administering a compound or combination therapy of the present invention to a patient that is in need of treatment or likely to respond to a therapy of the invention. In those embodiments where the patient is already undergoing treatment in accordance with the invention, $LTB_4$ levels in the patient sample lower than those measured in a sample previously obtained are indicative that the patient is responding positively to the therapy. In cases where the patient is responding positively to a therapy of the present invention, the therapy is continued until the LTB4 levels in the patient are reduced to a level comparable to a normal control level. Optionally, the therapy is continued to maintain alleviation of one or more symptom of PAH, or a disorder disclosed herein. Alternatively, the therapy is continued until one or more symptoms of a disorder of the present invention are alleviated in the patient. Alternatively, the therapy is continued until the treatment is determined to be efficacious using methods described herein, including assessment of endpoint parameters. In cases where the patient is determined to not be likely to respond to a therapy of the invention, the patient is not administered the therapy.

$LTB_4$ levels at least 2-fold higher than levels in a normal control are indicative that a patient is in need of treatment and likely to respond to a therapy of the invention. In other embodiments, levels at least 3-fold to 5-fold higher than levels in a normal control are indicative that a patient is in need of treatment and likely to respond to a therapy of the invention. In various embodiments, the levels are determined from a biological sample (i.e., a patient's serum or blood sample). In one embodiment, the level of $LTB_4$ in the blood serum of human PAH (immune-dysregulated PAH) patients is measured. The measurement of the circulating $LTB_4$ level in the serum of patients may be relied on to classify PAH patients for treatment efficacy.

Some embodiments of the current disclosure provide use of $LTB_4$ as a disease marker for different subtypes of Group I PAH (immune-dysregulated PAH, more inflamed populations). Measurement of $LTB_4$ level can provide strong clinical indication for treatment that may be relied on to stratify PAH patients undergoing therapy.

Thus, while any PAH patient can be treated in accordance with the methods of the invention, in some embodiments, a patient sample will be obtained, LTB4 levels or LTB4 activity in that sample will be measured (directly or indirectly), and the decision to treat will be made based on whether the measured LTB4 level or activity is higher than a normal control value, which will depend on a variety of factors, including the nature of the sample, the handling protocol for the sample, and the assay and assay methodology used to obtain the measurement.

While a variety of samples and assay methods can be used to obtain the LTB4 level or activity determination, in one illustrative embodiment, a blood sample is obtained from a prospective patient, and the plasma LTB4 level is measured. LTB4 levels were measured using an ELISA or an LC/MS/MS assay. The results showed that, with this sample type using this assay, LTB4 levels of non-PAH patients were in the range of 0 pg/ml to 400 pg/ml, or 0 pg/ml to 200 pg/ml, or 0 pg/ml to 100 pg/ml, and LTB4 levels in PAH patients expected to respond to the methods of this invention were in the range of >400 pg/ml to 6,000 pg/ml. Thus, in one embodiment using plasma samples and an LC/MS/MS or an ELISA assay conducted as described in the examples, LTB4 plasma levels of >400 pg/ml or higher are indicative that a PAH patient will respond to therapy in accordance with the methods of the invention. In various other embodiments, the LTB4 level that indicates a patient is likely to respond to therapy is >100 pg/ml, >200 pg/ml, 300 pg/ml, >600 pg/ml, and >1000 pg/ml.

Connective tissue disease PAH (CTD-PAH) patients (also referred to herein as immune dysregulated PAH), which include PAH patients with associated disorders such as scleroderma, systemic sclerosis, lupus, Sjogren's syndrome, rheumatoid arthritis, anti-phospholipid syndrome, and mixed connective tissue disease, will generally have higher LTB4 levels than other PAH patients and much higher levels than most healthy humans.

As an example of this embodiment of the invention, one can conduct a clinical trial using LTB4 levels as an entry criteria. Patients screened for eligibility to participate in the trial will be symptomatic on stable PAH-specific background therapy. In one embodiment, patients enrolled will be CTD-PAH patients with confirmed, elevated baseline serum LTB4 levels of >300 pg/ml. An open-label pilot study can use a single, well-tolerated dose of ubenimex (or other compound useful in the methods of the invention) for 24 weeks ("treatment period") but allow for monthly "interim looks" and evaluation of multiple outcomes and intermittent assessments during the trial. Outcome assessments could include change in hemodynamics by right heart catheterization at baseline, week 12, and week 24.

Various endpoint parameters can be assessed to determine efficacy of a treatment of the present invention, e.g., LTB4 level, pulmonary vascular resistance (PVR), mean pulmonary arterial pressure (PAP), cardiac index (CI), mean pulmonary capillary wedge pressure (PCWP), right atrial pressure (RAP), six-minute walk distance (6 MWD), brain natriuretic peptide (BNP) level, diffusion of lung capacity (DLCO), and death or survival. See, Chung et al. Chest (2010), 138(6): 1383-1394.

LTB4 level can be used as an endpoint parameter to determine efficacy of treatment for PAH, or a disorder disclosed herein.

PVR is commonly used as an endpoint parameter for determination of efficacy of treatment for PAH. A PVR of a subject of >240 dyn·sec/cm$^5$ is an indication of mild PAH. A PVR of a subject of 600-800 dyn·sec/cm$^5$ indicates moderate to severe PAH. After treatment using the methods and compositions of the invention, a decrease in PVR in a subject of 130 dyn·sec/cm$^5$ or more indicates efficacious treatment. For example, administration of a LTA$_4$H inhibitor to a subject with PAH that leads to a decrease in PVR of 180-350 dyn·sec/cm$^5$ indicates efficacious treatment.

Mean pulmonary arterial pressure (PAP) is also used as an endpoint parameter to determine efficacy of treatment for PAH. A subject without PAH has a mean PAP ranging from about 15-24 mmHg. A subject having mild PAH has a mean PAP of about 25-30 mmHg (e.g., >25 mmHg at rest or 30 mmHg with exercise). A subject having severe PAH has a PAP of greater than 30 mmHg, for e.g., 40-70 mmHg or 60-70 mmHg. After treatment, a decrease in PAP of greater than 1.5 mmHg indicates efficacious treatment. In one embodiment, treatment leads to a decrease in PAP of greater than 5, 10, 20, 40, or 50 mmHg, which is indicative of efficacious treatment.

Cardiac index (CI) is also used as an endpoint parameter for determining efficacy of treatment for PAH. A low or decreased CI is indicative of heart failure. For e.g., a CI of 2.5 L/min/m$^2$ or less is indicative of PAH or heart failure. After treatment, a CI increase of more than 0.3 L/min/m$^2$ is indicative of efficacious treatment.

Mean pulmonary capillary wedge pressure (PCWP) can be used as an endpoint parameter for determining efficacy of treatment for PAH. A mean PCWP of less than or equal to 18 mmHg (e.g., less than or equal to 10 mmHg) indicates a subject having PAH. After treatment, an increase in mean PCWP of greater than 0.5 mmHg is indicative of efficacious treatment.

Right atrial pressure (RAP) is also used as an endpoint parameter to determine efficacy of treatment for PAH. A subject not suffering from PAH has a normal RAP of 0-8 mmHg. A RAP of 8 mmHg or greater is indicative of PAH. A subject suffering from severe PAH has a RAP of about 20 mmHg. After treatment, a decrease of greater than 0.5 mmHg is indicative of efficacious treatment.

Six-minute walk distance (6 MWD) is used as an endpoint parameter to determine efficacy of treatment of PAH. The mean 6 MWD of patients with CTD-PAH is about 300 m. After treatment, an increase in 6 MWD of 25 m or more, or greater than 10% increase indicates efficacious treatment. For example, after treatment, a 6 MWD of 1000 m or more indicates efficacious treatment.

Brain Nauriuretic Peptide (BNP) is used as an endpoint parameter to determine efficacy of treatment of PAH. BNP is a sensitive marker for the worsening of heart failure and is a predictor of mortality in PAH patients. Normal levels of BNP are <100 pg/mL, e.g. 30-90 pg/mL. Higher levels of BNP indicate worsening of heart failure. A BNP level of about 100-200 pg/mL, e.g., 160 pg/mL or higher, indicates early heart failure. A BNP level of about 200-1000 pg/mL indicates real heart failure. The mean BNP level of CTD-PAH patients is about 430 pg/mL. After treatment, any reduction in BNP level indicates efficacious treatment.

Diffusion of lung capacity (DLCO), or diffusion capacity of CO, is also used as an endpoint parameter to determine efficacy of treatment of PAH. DLCO measures the ability of carbon monoxide (CO) to diffuse across membranes. A subject not suffering from PAH has a normal DLCO of greater than 80%. A subject suffering from PAH has an abnormal DLC of less than 80%, less than 65%, or less than 45%. After treatment, any increase in % DLCO indicates efficacious treatment.

Death is also used as an endpoint for efficacy of treatment of PAH. With the currently available PAH management methods, the average one-year survival rate of CTD-PAH patients is 86%, the average 1-year survival rate of idiopathic PAH patients is 93%, and the average 1-year survival rate of PAH patients with systemic sclerosis is 82%. The compositions and methods of the invention can increase the survival rate of PAH patients. In one embodiment, after treatment using the present invention, an increase in the average 1-year survival rate of PAH patients indicates efficacious treatment. For example, the compositions and methods of the invention increase the 1-year average survival rate of PAH patients to 82% or greater, 86% or greater, or 93% or greater. In another embodiment, an increase in the time to death after diagnosis of a PAH patient indicates efficacious treatment. For example, a LTA$_4$H inhibitor of the invention extends the time to death of a PAH patient by at least 1, 2, 3, 4, 5, or 6 years beyond the current average lifespan of PAH patients. Preferably, the PAH patient suffers from a connective tissue disorder, such as scleroderma or systemic sclerosis. For example, a $LTA_4H$ inhibitor of the invention extends the life of a PAH patient having systemic sclerosis.

The present invention provides methods of determining efficacy of a PAH treatment in a subject in need thereof by (a) measuring an endpoint level of a parameter in a subject in need thereof, where the endpoint level is measured after treatment has started, (b) comparing the endpoint level of the parameter to a baseline level of the parameter, where the baseline level is measured in the same subject before treatment is begun, and (c) determining the efficacy of the PAH treatment based on the comparison step.

Furthermore, the present invention provides methods of determining efficacy of a PAH treatment in a subject in need thereof by (a) measuring the endpoint level of a parameter in a subject in need thereof after treatment has begun, (b) comparing the endpoint level of the parameter to a reference value of the parameter, where the reference value is an average value of the parameter determined from a population of patients suffering from PAH, and (c) determining the efficacy of the PAH treatment based on the comparison step.

An exemplary parameter used in these methods is LTB4 level. A level of LTB4 is determined in the biological sample of a subject. A baseline or reference value of LTB4 can be 100 pg/mL or greater, 200 pg/mL or greater, 300 pg/mL or greater, 400 pg/mL or greater, 500 pg/mL or greater, 600 pg/mL or greater, or 100 pg/mL or greater. The treatment provided in the invention is efficacious if, after treatment has started, the endpoint LTB4 level of the subject decreases from the baseline or reference LTB4 level. For example, the endpoint LTB4 level of the subject decreases to 600 pg/mL or less, 500 pg/mL or less, 400 pg/mL or less, 300 pg/mL or less, 200 pg/mL or less, or 100 pg/mL or less. Also, the treatment provided in the invention is efficacious if, after treatment has started, the endpoint LTB4 level is 30 pg/mg of tissue or lower, 20 pg/mg of tissue of lower, 10 pg/mg of tissue or lower, 7.5 pg/mg of tissue or lower, or 5 pg/mg of tissue or lower. In other embodiments, the treatment provided in the invention is efficacious if, after treatment has started, the endpoint LTB4 level is lower than the baseline LTB4 level by 2-fold or more, 3-fold or more, 4-fold or more, or 5-fold or more.

An exemplary parameter used in the methods is pulmonary vascular resistance (PVR). The baseline or reference PVR level can be 200 dyn·sec/cm$^5$ or greater, 240 dyn·sec/cm$^5$ or greater, 300 dyn·sec/cm$^5$ or greater, 400 dyn·sec/cm$^5$ or greater, 500 dyn·sec/cm$^5$ or greater, 600 dyn·sec/cm$^5$ or greater, 700 dyn·sec/cm$^5$ or greater, or 800 dyn·sec/cm$^5$ or greater. The treatment provided in the invention is efficacious if, after treatment has started, the endpoint PVR level of the subject decreases from the baseline or reference PVR level by 70 dyn·sec/cm$^5$ or more, 100 dyn·sec/cm$^5$ or more, 130 dyn·sec/cm$^5$ or more, or 160 dyn·sec/cm$^5$ or more.

Another exemplary parameter used in the methods is pulmonary arterial pressure (PAP). The baseline or reference PAP level can be 20 mmHg or greater, 25 mmHg or greater, 30 mmHg or greater, 35 mmHg or greater, 40 mmHg or greater, 45 mmHg or greater, 50 mmHg or greater, 60 mmHg or greater, or 70 mmHg or greater. The treatment provided in the invention is efficacious if, after treatment has started, the endpoint PAP level of the subject decreases from the baseline or reference PAP level by 0.5 mmHg or more, 1 mmHg or more, 1.5 mmHg or more, 5 mmHg or more, 10 mmHg or more, 20 mmHg or more, 30 mmHg or more, 40 mmHg or more, or 50 mmHg.

An exemplary parameter used in the methods can also be cardiac index (CI). A baseline or reference CI level can be 5 L/min/m$^2$ or lower, 2.5 L/min/m$^2$ or lower, 2 L/min/m$^2$ or lower, 1.5 L/min/m$^2$ or lower, or 1 L/min/m$^2$ or lower. A treatment provided in the invention is efficacious if after treatment has started, the endpoint CI level increases from the baseline or reference CI level by 0.1 or more, 0.2 or more, 0.3 or more, 0.4 or more, 0.5 or more, 1 or more, or 2 or more.

An exemplary parameter used in the methods can be pulmonary capillary wedge pressure (PCWP). A baseline or reference PCWP level can be 36 mmHg or less, 24 mmHg or less, 18 mmHg or less, 10 mmHg, or 5 mmHg or less. A treatment provided in the invention is efficacious if, after treatment has started, the endpoint PCWP level increases from the baseline or reference PCWP level by 0.2 mmHg or more, 0.3 mmHg or more, 0.4 mmHg or more, 0.5 mmHg or more, 0.6 mmHg or more, 1 mmHg or more, or 5 mmHg or more.

Another exemplary parameter used in the methods can be right atrial pressure (RAP). A baseline or reference RAP level can be 4 mmHg or more, 6 mmHg or more, 8 mmHg or more, 10 mmHg or more, 12 mmHg or more, 16 mmHg or more, 20 mmHg or more, or 25 mmHg or more. A treatment provided in the invention is efficacious if, after treatment has started, the endpoint RAP level of the subject decreases from the baseline or reference RAP level by 5 mmHg or more, 2.5 mmHg or more, 1 mmHg or more, 0.5 mmHg or more, or 0.2 mmHg or more.

An exemplary parameter used in the methods can be six-minute walk distance (6 MWD). A baseline or reference 6 MWD can be 50 m or less, 100 m or less, 200 m or less, 300 m or less, 400 m or less, or 500 m or less. A treatment provided in the invention is efficacious if, after treatment has started, the endpoint 6 MWD of the subject increases from the baseline or reference 6 MWD by 10 m or more, 15 m or more, 20 m or more, 25 m or more, 30 m or more, or 50 m or more. Alternatively or in addition, treatment provided in the invention is efficacious if, after treatment has started, the endpoint 6 MWD of the subject increases by 3% or more, 4% or more, 5% or more, 10% or more, or 20% or more of the baseline level.

Another parameter used in the methods can be brain natriuretic peptide (BNP) level. A baseline or reference BNP level can be 60 pg/mL or higher, 80 pg/mL or higher, 100 pg/mL or higher, 120 pg/mL or higher, 140 pg/mL or higher, 200 pg/mL or higher, 500 pg/mL or higher, or 1000 pg/mL or higher. A treatment provided in the invention is efficacious if, after treatment has started, the endpoint BNP level of the subject decreases from the baseline or reference BNP level. For example, the endpoint BNP level of the subject can decrease by 1 pg/mL or more, 2 pg/mL or more, 5 pg/mL or more, 10 pg/mL or more, 20 pg/mL or more, 100 pg/mL or more, 500 pg/mL or more, or 1000 pg/mL or more.

Diffusion of lung capacity (DLCO), or diffusion capacity of CO, can also be used in the methods as a parameter to determine efficacy. A baseline or reference DLCO can be 90% or less, 80% or less, 70% or less, 50% or less, 45% or less, or 40% or less. A treatment provided in the invention is efficacious if, after treatment has started, the endpoint DLCO is increased from the baseline level. For example, the endpoint DLCO can be increased from the baseline or reference DLCO by 1% or more, 5% or more, 10% or more, 15% or more, 20% or more, or 50% or more.

In addition, average survival rate can be used in the methods a parameter to determine efficacy in a population of one or more subjects. A reference average survival rate is 95% or lower, 93% or lower, 90% or lower, 86% or lower, 82% or lower, or 78% or lower. The average survival rate can be an average 1-year survival rate. A treatment provided in the invention is efficacious in a population of one or more subjects if, after treatment has started, the average survival rate increases. For example, the average survival rate can increase from the reference average survival rate by 1% or more, 2% or more, 5% or more, 10% or more, or 20% or more.

Another exemplary parameter for use in the methods to determine efficacy of treatment in a subject is time to death after diagnosis with PAH. A reference time to death can be 1 year or less, 2 years or less, 5 years or less, or 7 years or less. A treatment provided in the invention is efficacious if, after treatment has started, the time to death of the subject is higher than the reference time to death. For example, the time to death of the subject can increase from the reference time to death by 0.5 years or more, 1 year or more, 2 years or more, 3 years or more, 4 years or more, 5 years or more, or 6 years or more.

The methods can further comprise continuing the therapy if the therapy is determined to be efficacious. The methods can comprise maintaining, tapering, reducing, or stopping the administered amount of a compound or compounds in the therapy if the therapy is determined to be efficacious. The methods can comprise increasing the administered amount of a compound or compounds in the therapy if it is determined not to be efficacious. Alternatively, the methods can comprise stopping therapy if it is determined not to be efficacious.

In an illustrative example, if PVR is the primary endpoint parameter, a trial of only 15 patients will have 70% power to detect a change of −200 dyn·sec/cm$^5$ from baseline to week 24 at an alpha of 0.10. In addition, on a monthly basis (week 4, 8, 12, 16, 20), hemodynamic assessments can be conducted by echocardiogram, 6-minute walk distance can be tested, the biomarker BNP (brain natriuritec peptide a marker of right heart failure) can be assayed, functional class change can be assessed, and time to clinical worsening can all be evaluated. PVR (pulmonary vascular resistance) is a primary efficacy endpoint. Changes in PVR in PAH trials of 12 to 16 weeks duration have ranged from −209 to −345 dyn·sec/cm$^5$, and for trials of patients receiving PAH-specific background therapy from −172 to −230 dyn·sec/cm$^5$. A trial of 60 patients, with 20 patients in each arm receiving ubenimex (a 60 mg TID cohort and a 60 mg BID cohort) versus a control arm of 20 patients not receiving ubenimex will provide >80% power at an α-level (2-sided) of 0.05 to detect a −150 dyn·sec/cm$^5$ treatment effect in PVR (mean change from baseline to Week 24). Subset analyses can be conducted using plasma LTB4 level to define differences in hemodynamic changes and exercise tolerance by group. A 6-month (as opposed to 12-16 week) duration of treatment can confirm the mechanism of action of ubenimex in PAH is antiproliferative and anti-inflammatory rather than vasodilatory.

While blood plasma or serum are convenient to use samples for assaying LTB4 levels, a variety of other biological samples (i.e. bronchoalveolar lavage fluid (BALF), exhaled breath condensate (EBC), sputum, urine, and lung, skin or other tissues) can be used. Generally, regardless of sample source, LTB4 levels higher than about 100 pg/ml are indicative of a patient likely to respond to therapy in accordance with the invention, but those of skill in the art recognize that different sample sources, different assay formats, and other variables can affect the results obtained and can readily perform tests to correlate the results of one set of sample/assay conditions with another. Generally, however, the highest LTB4 levels will be obtained from BALF, sputum, and EBC samples, which will generally be higher than plasma or serum sample levels (from the same patient), which in turn will generally be higher than the LTB4 levels measured in tissue and urine (again, compared to other sample sources from the same patient). Despite the differences in LTB4 levels from sample type to sample type, LTB4 concentrations will be generally higher in the subjects most likely to respond to therapy than the levels measured in healthy subjects and in PAH patients more likely not to respond favorably to therapy, regardless of the type of sample used to obtain the LTB4 measurement. LTB4 is intrinsically unstable, so any sample should be collected and handled in a manner that avoids (or accounts for) degradation of the LTB4 in the sample. Suitable sample handling protocols for various sample types are described below.

Blood serum is obtained from coagulated blood (red blood cell clot). Blood is obtained from venipuncture and allowed to clot, followed by centrifugation (i.e., 30 min. at 1,000-2,000× g) using a refrigerated centrifuge. After centrifugation, the serum supernatant is immediately transferred into a clean sample vessel and is ready for analysis (Seggev et al. Chest. 1991 February; 99(2): 289-91). Blood plasma is obtained from venipuncture with the blood collected into anticoagulant-treated tubes treated with EDTA, acid citrate dextrose, or heparin. Blood cells are separated from the blood plasma by centrifugation (e.g. as above). After centrifugation, the plasma supernatant is immediately transferred into a clean sample vessel and is ready for analysis (Auner et al. Mediators of Inflammation Volume 2012 (2012), Article ID 536156, doi:10.1155/2012/536156; and Shindo et al. Eur Respir J. 1995 April; 8(4):605-10.))

Exhaled breath condensate (EBC) samples can be collected with a device composed of a mouthpiece, hose, and one-way valve connected to a condensing chamber placed in ice or liquid nitrogen to cool the breath. The condensing chamber can be made of double-walled of glass, the inner wall of which is cooled by ice or liquid nitrogen. Generally, subjects wear a noseclip and are asked to breath tidally for 15 min. though a mouthpiece connected to the condenser. The respiratory rate ranges between 15-20 breaths/min. Subjects are typically asked to rinse their mouth with distilled water before and after ~7 min. of condensing to reduce evaporation of LTB4 from saliva and the nasal space. Exhaled air enters and leaves the chamber through one-way valves at the inlet and the outlet while the chamber is closed. EBC is collected between the two glass surfaces; usually, about 1.0-2.5 ml of EBC is collected. If one wants to correct for saliva contamination, one can measure amylase (e.g. using a kit available from Sigma). See Montuschi and Barnes. J. J Allergy Clin Immunol. 2002 April; 109(4):615-20.

Bronchoalveolar lavage fluid (BALF) samples are collected using a bronchoscope, which is passed through the mouth or nose into the lungs. Fluid is deposited into a small part of the lung and then collected. The fluid is then centrifuged (as above) and the supernatant is immediately transferred into a clean sample vessel and is ready for analysis (Wardlaw et al. J Allergy Clin Immunol. 1989 July; 84(1):19-26).

Sputum samples can be obtained using procedures known in the art. For patients unable to produce sputum readily, one can obtain Induced Sputum (IS) samples by treating with, e.g., 400 mg inhaled salbutamol to inhibit excessive airway constriction and then administering an aerosol of isotonic and hypertonic saline via inhalation from an ultrasonic nebuliser. The concentrations of saline can be, for example and without limitation, 0.9, 3, 4 and 5%; the duration of each inhalation concentration is 7 min., followed by forced expiratory volume in one second measurements. After each period of inhalation, the patient is instructed to blow their nose and rinse their mouth with water to minimize contamination of the sputum sample. The subject may be asked to cough deeply to attempt to expectorate sputum. The sample is considered adequate when it appears macroscopically to be free from saliva and when it weighs more than ~1 g. (see J. Corhay et al. Am J Respir Crit. Care Med 179; 2009:A2946.)

Urine samples are collected, centrifuged (e.g. as above) to remove cells, and the supernatant is immediately transferred into a clean sample vessel and is ready for analysis (Mita et al. Clin Exp Allergy. 2004 August; 34(8):1262-9.)

Tissue samples, such as samples from lung or skin, can be used to measure LTB4 levels (which may be expressed in units of pg/mg of tissue), and patients likely to respond to treatment will, in some embodiments, have LTB4 levels of 7.5 pg/mg of tissue or higher, e.g. 10 pg/mg, 15 pg/mg, 20 pg/mg, 25 pg/mg, 30 pg/mg, 35 pg/mg, 40 pg/mg, or higher. For example and without limitation, the LTB4 concentration can be detected from lung and skin tissues using matrix-assisted laser desorption/ionization (MALDI) mass spectrometry (Bowers et al. Am J Respir Crit. Care Med. 2004 Mar. 15; 169(6):764-9. Epub 2003 Dec. 30).

There are a variety of ways to measure LTB4 levels. One convenient method is ELISA, such as the ELISA commercially available as the LTB4 ELISA kit from Cayman Chemical (No. 520111) is used. Other suitable commercially available kits include the Luminex® competitive LTB4 ELISA kit from Cayman Chemical (No. 500260); Alkaline Phosphatase (AP) Competitive LTB4 ELISA from Thermo Scientific (# EHLTB4); Human LTB4 ELISA Kit from Invitrogen (#KHL1741); Parameter™ LTB4 ELISA Kit from R&D (KGE006B, SKGE006B, PKGE006B); and the Acetylcholinesterase (ACE™) competitive Enzyme Immunoactivity (EIA) for LTB4 from Bio-Medical Assay. Gas chromatography mass spectrometry (GC/MS) can also be used to measure LTB4 levels (see MacDermot et al. Prostaglandins. 1984 February; 27(2):163-79). High pressure liquid chromatography (HPLC-UV) can also be used to measure LTB4 levels (see Westcott et al. Prostaglandins. 1986 February; 31(2): 227-37.) Liquid chromatography mass spectrometry (LC/MS and LC/MS/MS) can also be used to measure LTB4 levels (see Montuschi et al. Rapid Commun Mass Spectrom. 2004; 18(22):2723-9; Montuschi et al. Respir Res. 2005 Oct. 19; 6:119; Araujo et al. J Chromatogr A. 2012 Oct. 19; 1260:102-10). Other spectrometry related methods can be used, such as negative ion chemical ionization mass spectrometry (NICI/MS) and negative ion chemical ionization/gas chromatography/tandem mass spectrometry (NICI/GS/MS/MS) (see Strife and Murphy, Prostaglandins Leukot Med. 1984 January; 13(1):1-8, and Takamoto et al. J Pharm Biomed Anal. 1995 November; 13(12):1465-72). Radioimmunoassay (RIA) methods can also be used to measure LTB4 levels (see Lewis et al. Proc Natl Acad Sci USA. 1982 December; 79(24):7904-8; Salmon et al. Prostaglandins. 1982 August; 24(2):225-35; and Levine et al. Proc Natl Acad Sci USA. 1981 December; 78(12):7692-6).

ELISA generally has high sensitivity and is suitable for large-scale studies, but ELISAs may not have the high specificity of other assays, particularly when complex biological fluids such as blood are analyzed. GC/MS and LC/MS/MS techniques allow LTB4 detection in the picogram range and are considered to be the gold standard assays, as they are highly specific. In contrast to GC/MS, LC/MS/MS analysis does not require a two-step derivatization procedure, leading to better recovery, reducing the time for sample pretreatment, and avoiding incomplete derivatization and formation of derivatization reagent side products that could interfere with the assay. In many embodiments, however, an ELISA will be used to determine LTB4 levels, although GC/MS, LC/MS, and LC/NIS/MS methods may be employed in various embodiments as well.

While one can assess LTB4 levels directly and easily using any of the assays described above, one can also measure LTB4 levels indirectly, using assays that detect LTB4 production or activity. For example, higher levels of $LTA_4H$ and higher levels of p5LO staining in lung tissue are examples of assays that can be used to measure LTB4 levels indirectly.

In other embodiments, $LTC_4$ levels are measured, alone or in combination with measuring $LTB_4$ levels, and high $LTC_4$ levels, in the absence of elevated $LTB_4$ levels are indicative that a patient is unlikely to respond or is not responding to a therapy of the invention.

Other features and advantages of the present invention are apparent from the different examples that follow. The examples below illustrate different aspects and embodiments of the present invention and how to make and practice them. The examples do not limit the claimed invention. Although methods and materials similar or equivalent to those described herein can be used in the practice of the present invention, suitable methods and materials are described below. Based on the present disclosure the skilled artisan can identify and employ other components and methodology useful for practicing the present invention.

EXAMPLES

Example 1

PH is Characterized by Activation of the $LTB_4$ Axis in Macrophages

This example shows that macrophage $LTB_4$ is prominent in PH. The animal model used in this example (and unless otherwise noted) was the athymic nude rat model. To reiterate, athymic rat effectively models Group I PAH, but by convention, in animal models, this disease is still referred to generically as 'PH'.

The athymic nude rat model is an accepted model of severe PAH associated with immune dysregulation. Athymic nude rats (rnu/rnu) (Charles River Laboratories) were used for these studies. Six to eight week old animals were injected subcutaneously (s.c.) with a single dose of either SU5416 (SU) (10 mg/kg) dissolved in DMSO or DMSO (vehicle) alone. All animals were maintained in normoxic conditions. PH progression was monitored by weekly echocardiography (ECHO). Survival of rats was monitored out to wk 5 when they underwent a terminal right heart catheterization. PH was confirmed by ECHO. Hemodynamic measurements included right ventricular systolic pressure (RVSP) determined by right heart catheterization and right ventricular hypertrophy (RVH) determined by the weight ratio of RV/(LV+S) (right ventricle/(left ventricle+septum)).

5-LO and pSer271 5-LO co-localized to CD68$^+$ macrophages in the lung and increased in numbers as PH was evolving. Progressive nuclear membrane localization of pSer271 5-LO and increased expression of $LTA_4H$ indicated rising $LTB_4$ biosynthesis in pulmonary macrophages in PH. Significantly increased $LTB_4$ levels were noted in the bronchoalveolar lavage fluid (BALF) and serum from animals with PH as compared to that from control animals. In addition, whole lung transcript levels for the high affinity $LTB_4$ receptor (BLT1) rose progressively as PH developed in contrast to the Cysteinyl leukotriene receptor (CysLT1). An examination of solid organs indicated that lung was the principal site of $LTB_4$ biosynthesis and macrophages, rather than other leukocytes, were the leading source of this particular leukotriene.

The results reported in this example demonstrate that the highest level of $LTB_4$ biosynthesis in PH was found in macrophages concentrated around diseased arterioles, which is consistent with $LTB_4$ being elevated at the site of greatest disease activity.

Example 2

Macrophage Secretion of $LTB_4$ Induces Pulmonary Arterial Endothelial Cell (PAEC) Apoptosis This example shows that $LTB_4$ directly induces endothelial cell death.

The results reported in this example were obtained using the following PAEC apoptosis assay. Rat pulmonary arterial endothelial cells (PAECs) were co-cultured with macrophages (+/− transfection) for 24 hr. They were then washed once with PBS and once with binding buffer from the Annexin V Apoptosis Detection Kit (88-8007; eBioscience). Cells were then suspended in binding buffer at $1-5 \times 10^6$/ml. 5 µl of APC conjugated Annexin V was added to 100 µl of cells, which were then incubated at room temperature for 15 min. Five µl of propidium iodide staining solution were added 5 min prior to flow cytometry analysis on an LSRFortessa cell analyzer (BD Biosciences).

Figure 2:
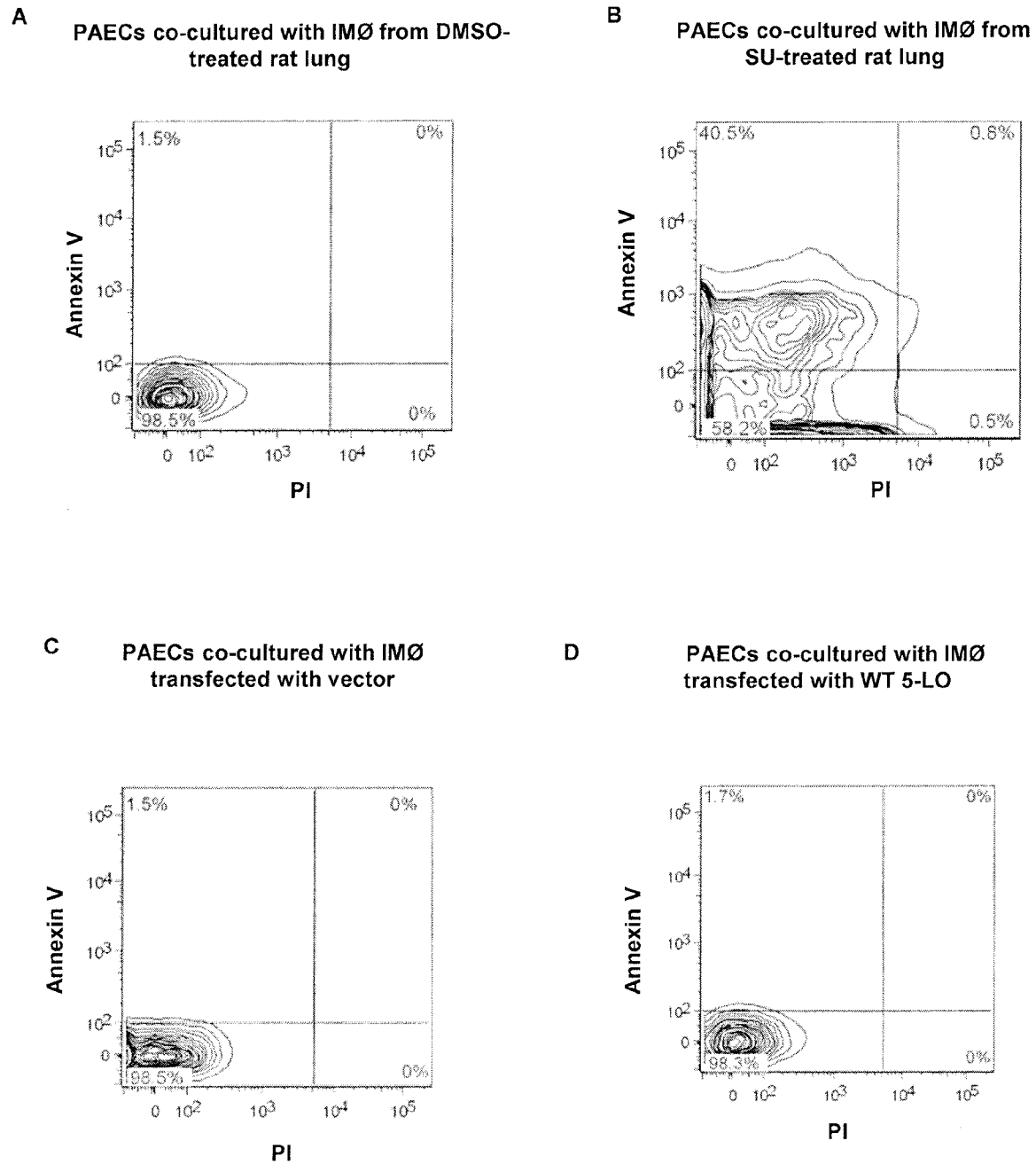
FIG. 2 is a series of graphs demonstrating that interstitial lung macrophage (IMØ)-secreted $LTB_4$ induces pulmonary arterial endothelial cell (PAEC) apoptosis. The transwell assay involved co-culturing IMØs from several sources with PAECs. IMØs, from (A) DMSO and (B) SU rat lungs, were isolated and co-cultured with PAECs. After 24 hr, PAEC apoptosis was analyzed by flow cytometry for Annexin V expression. To isolate the specific impact of $LTB_4$ generated by 5-LO activation further, IMØs were extracted from healthy rats and transfected with S271E to produce a phosphorylation mimic mutant or with S271A to produce a dephosphorylation mimic mutant. Vector and WT 5-LO DNA-transfected IMØs were used as controls. Flow cytometry was performed on PAECs co-cultured with IMØs extracted from healthy rats and transfected with (C) vector as control, (D) WT 5-LO, (E) S271A, (F) S271E (G) S271E mutant treated with n-acetyl cysteine (NAC) (200 nM) or (H) S271A mutant treated with $LTB_4$ (100 nM). PAECs were treated with (I) exogenous $LTB_4$ (200 nM) or (J) $LTB_4$ (200 nM) with a BLT1 inhibitor U75302 (1 mM) (n=3 experiments per group). Representative flow cytometry plots are shown. n=3 experiments per group.
Figure 2:
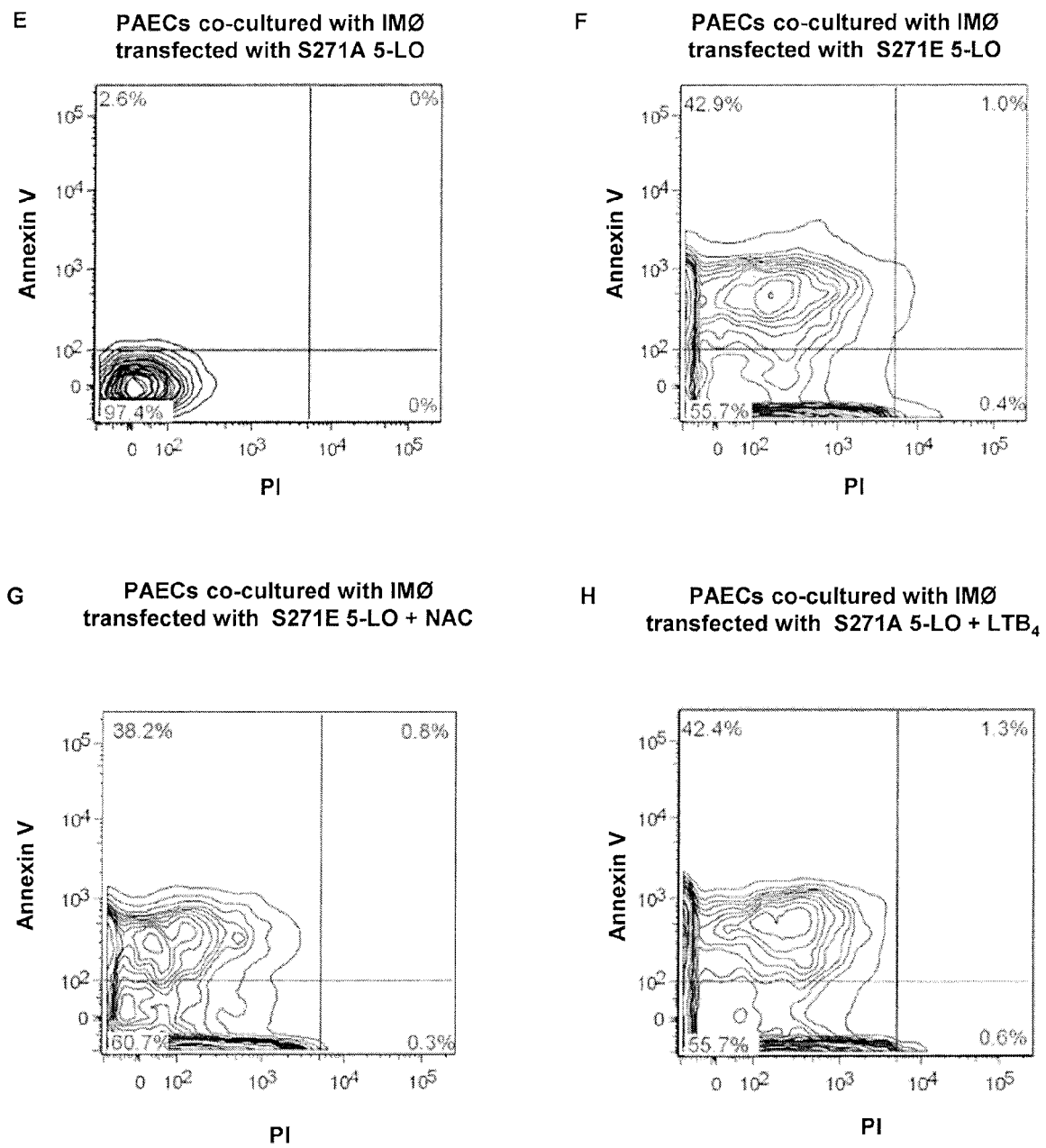
Figure 2:
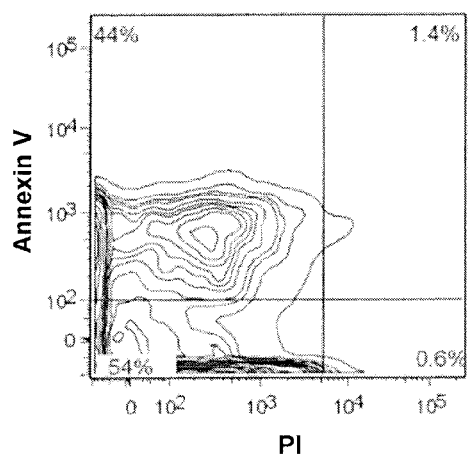
Figure 2:
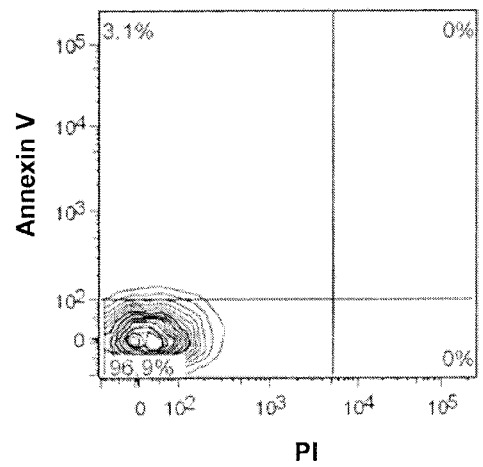

PAEC injury is regarded as an important early event in PAH pathogenesis. To demonstrate that lung macrophages can injure endothelial cells in PH lungs, a macrophage-PAEC co-culture system that utilized pulmonary macrophages purified separately from both the interstitial and alveolar compartments was established. In contrast to macrophages obtained from control lungs, macrophages isolated from the lungs of SU-treated athymic rats with PH induced significant endothelial cell apoptosis, as assessed by flow cytometric analysis of Annexin V staining (see FIGS. 2, A and B).

To demonstrate that macrophage-derived $LTB_4$ generation was sufficient to induce endothelial damage, macrophages from healthy rats were transfected with S271E 5-LO to produce a 5-LO phosphorylation mimic mutant with constitutive $LTB_4$ production, and with S271A to produce a dephosphorylation mimic mutant with deficient $LTB_4$ production. While macrophages transfected only with vector, WT 5-LO, or S271A DNA did not induce endothelial cell apoptosis (see FIGS. 2, C-E), S271E mutant macrophages caused notable PAEC death, similar to macrophages isolated from lungs of SU-treated rats (see FIG. 2F).

To demonstrate whether reactive oxygen species generated through the 5-LO-catalyzed enzymatic reaction played a role in PAEC apoptosis, cells were co-cultured with the antioxidant n-acetyl cysteine (NAC), and no diminution of apoptosis was observed (see FIG. 2G). Addition of exogenous $LTB_4$ (100 nM) to the co-cultures with macrophages transfected with S271A caused apoptosis (see FIG. 2H).

To confirm that $LTB_4$ was sufficient (in the absence of macrophages) to induce PAEC apoptosis, PAECs were cultured in various physiologically relevant concentrations of $LTB_4$, and significant apoptosis was observed at 24 hrs in a dose-dependent manner (see FIG. 2I); these results contrasted with those obtained by the addition of exogenous $LTC_4$, $LTD_4$, and $LTE_4$, which did not induce PAEC apoptosis. Blocking BLT1, the major receptor for $LTB_4$ in endothelial cells, using U75302 prevented $LTB_4$-mediated apoptosis (see FIG. 2J). Thus, this example demonstrates definitively that $LTB_4$ induces endothelial cell apoptotic death via signaling of endothelial cell BLT1.

Example 3

$LTB_4$ Induces PAEC Apoptosis Through Inhibition of the Endothelial Sphk1-eNOS Pathway This example shows how $LTB_4$ mediates endothelial cell apoptosis. $LTB_4$-induced endothelial cell apoptosis has not been previously described, and the results reported in this example provide a mechanism by which $LTB_4$ can be injurious to this cell population.

Because eNOS has been shown to be activated by S1P and is a fundamental endothelial cell survival factor, the culture medium of PAECs was analyzed for S1P concentrations. The results paralleled those of the apoptosis assays shown in FIG. 2, in that the experimental groups associated with endothelial cell apoptosis (i.e., macrophage co-culture groups: S271E, S271A+ exogenous $LTB_4$, and PAECs alone with exogenous $LTB_4$) all exhibited low S1P levels. Moreover, exogenously added SIP was able to rescue PAECs co-cultured with S271E cells.

These results show that $LTB_4$, secreted by activated macrophages, induces PAEC apoptosis in a BLT1-dependent manner through inhibition of endothelial Sphk1 phosphorylation, S1P synthesis, eNOS phosphorylation, and NO production.

Example 4

LTB4 Induces Human Pulmonary Arterial Smooth Muscle Cell (hPASMC) Proliferation and Hypertrophy This example shows that exogenous LTB4 induces human primary pulmonary arterial smooth muscle cell (hPASMC) proliferation and hypertrophy.

An in vitro toxicology assay kit (#M-5655, #8910, Sigma) was used to measure the number of viable hPASMC after LTB4 treatment. Briefly, hPASMCs were plated in a 96 well plate one day before treatment. Cells were treated with 200 nM or 400 nM LTB4 for 24 hr. On the day of assay, growing medium was first removed from the cells, then 20 µL of 12 mM MTT ((3-(4,5-Dimethylthiazol-2-yl)-2,5-diphenyltetrazolium bromide, a yellow tetrazole)) stock solution were then added to each well. After incubation at 37 degrees C. for 4 hr, 200 µL MTT dissolution solution (10% Triton X-100 plus 0.1 N HCl in anhydrous isopropanol) were added to each well. Relative optical density, which was used as a parameter for proliferation, was calculated by subtracting the absorbance at 690 nm from that at 570 nm. Cellular hypertrophy was determined by protein/DNA ratio. hPASMCs were seeded on 6 well plates. Cells were treated with 200 nM or 400 nM LTB4 for 24 hr. hPASMCs were then collected and divided into to two. For one part of each sample, a BCA protein assay kit (#23227, Thermo Scientific) was used to determined the total protein amount. DNA was purified from the other part of the sample using a Miniprep kit (QIAGEN). DNA concentration was then measured by nanodrop.

PASMC proliferation and hypertrophy are considered, along with PAEC injury, are key pathogenic events leading to plexiform lesion formation, the sin qua non histologic feature of PAH. 24 hr after LTB4 treatment, the number of hPASMC were directly proportional to the LTB4 concentration to which they were exposed. There were 1.8 fold more PASMC in the 200 nM LTB4 culture than in the negative control group, and two fold more in the 400 nM LTB4 culture. Cellular hypertrophy increased in a similar pattern.

Example 5

Blocking $LTB_4$ Biosynthesis or Downstream Signaling Specifically Reverses Established PH This example shows that $LTB_4$-targeted therapies of the invention are highly effective for reversing advanced (life-threatening) PH, as demonstrated in animal models (the athymic nude rat model described in Example 1, and another model, described in this example). These therapies are effective because they prevent or reduce changes in PAECs and PASMCs associated with PAH pathogenesis.

Drug treatments were as follows: ubenimex (0.25 mg/kg, 0.50 mg/kg, 0.75 mg/kg and 1 mg/kg), MK886 (5 mg/kg), LY293111 (0.5 mg/kg)), arachidonyl trifluoromethyl ketone (5 mg/kg), aspirin (100 mg/kg), and dicyclohexyl urea (30 mg/kg) were given once a day p.o.; JNJ26993135 (30 mg/kg) was given twice a day p.o.; zileuton (30 mg/kg) was given four times a day p.o.; dry particle ubenimex (5 mg/kg) was administered by inhalation three times a week, started 21 days after SU5416 administration (when severe PH was confirmed by ECHO).

Ubenimex [(2S,3R)-3-amino-2-hydroxy-4-phenylbutanoyl-L-leucine] (not a statin-derivative), is a well-tolerated $LTA_4H$ inhibitor that blocks $LTB_4$ formation. Systemic ubenimex therapy, initiated when SU was first administered to athymic rats, very effectively prevented PH development and prolonged survival in SU-treated rats. Given the potency of ubenimex in preventing PH development, four ubenimex-dosing regimens were tested (0.25 mg/kg, 0.50 mg/kg, 0.75 mg/kg and 1 mg/kg) using a sustained oral formulation provided by this invention. Ubenimex efficacy in reversing PAH was dose-dependent. The sustained release oral formulation was absorbed rapidly within 2-3 hours and was eliminated from the body with a $T_{1/2}$ of 12 hours. An inhalable dry powder formulation of ubenimex was also highly effective for reversing established PH (administered three times per week, starting late in disease development).

Figure 3:
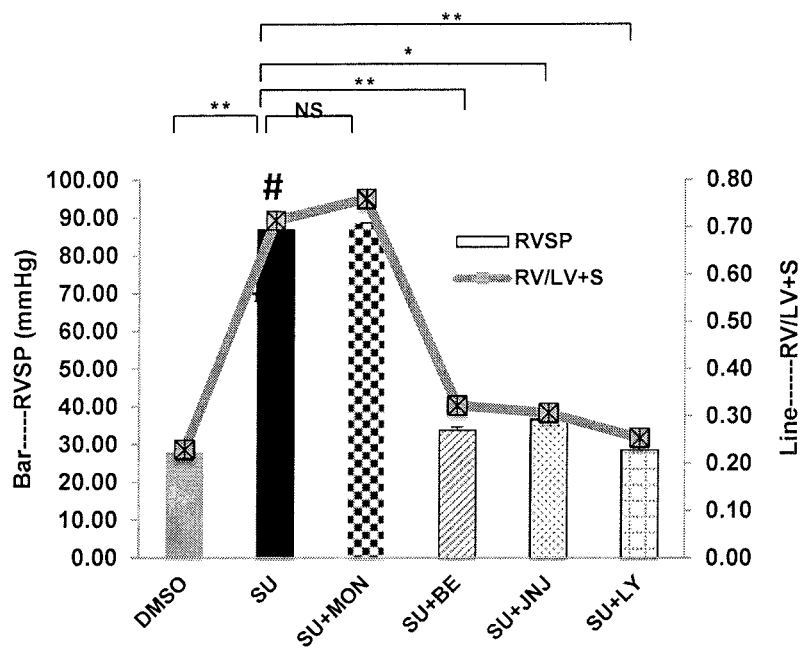
FIG. 3 demonstrates that blocking $LTB_4$ synthesis by ubenimex and JNJ26993135 or $LTB_4$ downstream signaling by LY293111 reverses established PH. Rats were treated with the CysLT1 receptor antagonist montelukast (MON); the $LTA_4H$ inhibitor ubenimex (BE); the $LTA_4H$ inhibitor JNJ26993135 (JNJ) or the BLT1 antagonist LY293111 (LY) starting 3 wk after SU5416 (SU) administration Animals were monitored by echocardiography (ECHO) weekly, and sacrificed for hemodynamics measurement at wk 5. (A) Right ventricle (RV) systolic pressure (RVSP) measurements in DMSO, SU, and 4 different treatment protocols were assessed at wk 5 post-SU administration. RV hypertrophy (RVH) measurements as assessed by the right ventricle to left ventricle plus septum (RV/LV+S) weight ratios. (B) Survival of rats after treatment was compared with DMSO and SU rats. (C) Representative immunohistochemistry images of pulmonary arterioles stained with α-smooth muscle actin (SMA) in lung tissues from controls and treatment groups at wk 5. (D) Percentage of medial wall thickness of α-SMA positive small vessels (<100 μm in external diameter). The percentage of wall thickness was determined as follows: % wall thickness= (WT1+WT2)/(external diameter of vessel)×100%, where WT1 and WT2 refer to wall thicknesses measured at two points diametrically opposite to each other. The endothelial component of the vessel wall was excluded from the measurements of wall thickness. (E) $LTB_4$ concentrations in BALF of controls and various treatment groups were measured by LC-MS/MS (n=6 per group). # SU data from historic controls were provided as comparator, because none of the SU (PH) rats survived to 5 weeks in this demonstration as reflected in survival curve. Two-way ANOVA with Bonferroni multiple comparisons test for post hoc analyses were used. Data are expressed as means±s.e.m. * is P<0.01; ** is P<0.001; NS is not significant.
Figure 3:
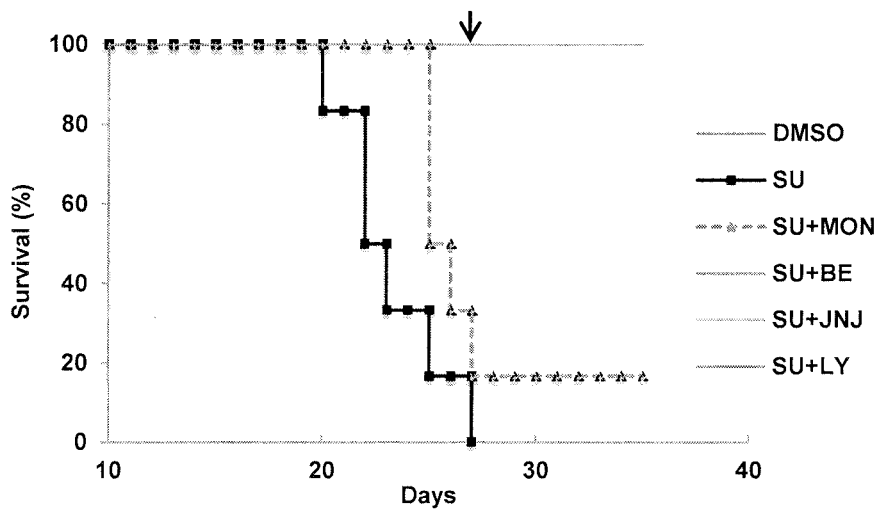
Figure 3:
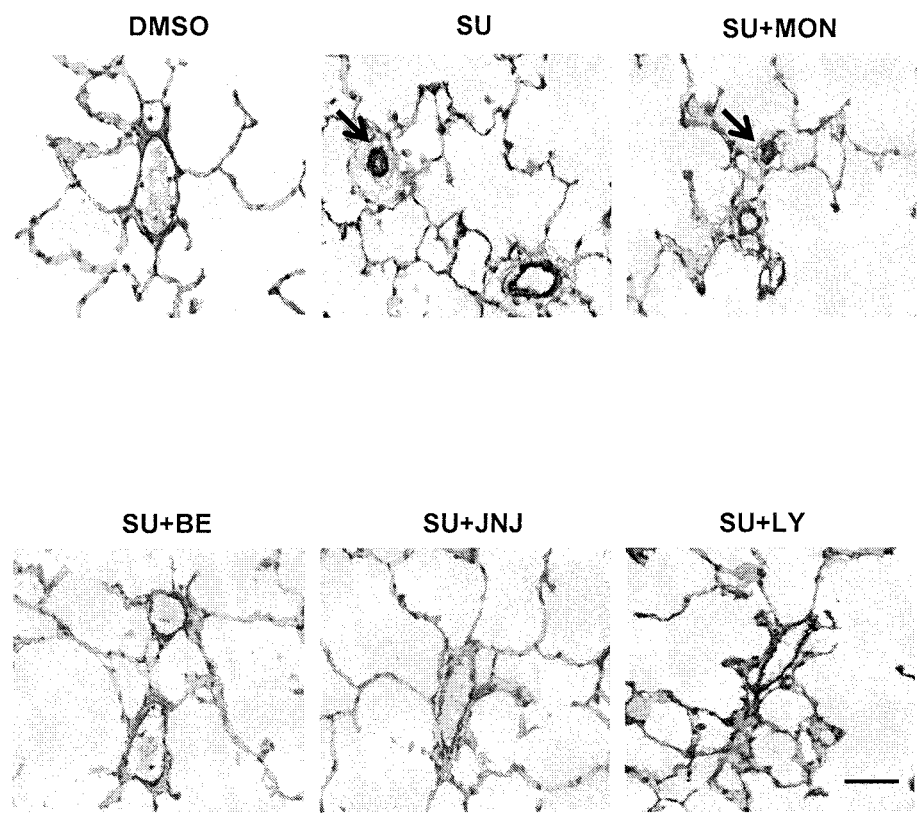
Figure 3:
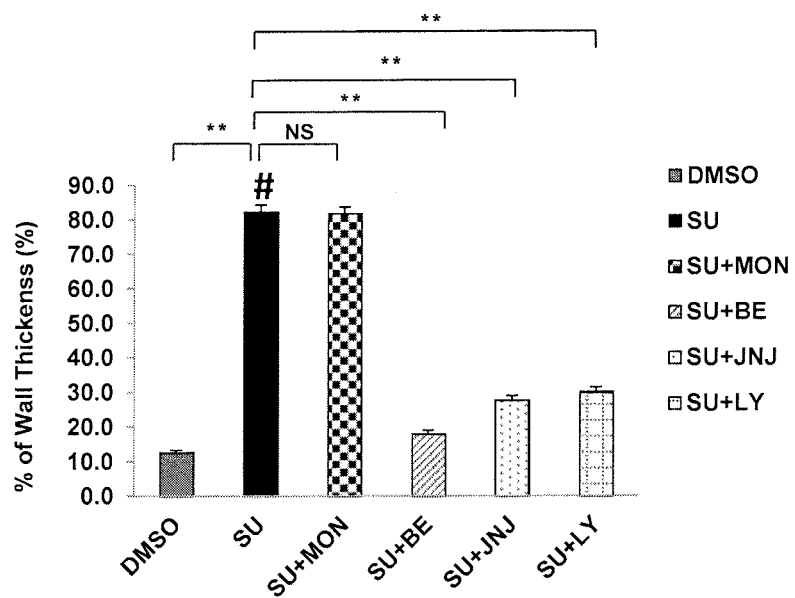
Figure 3:
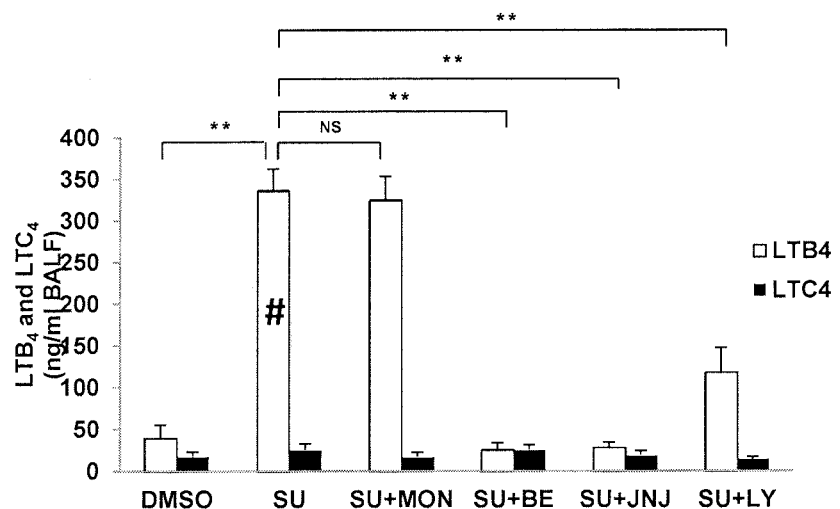

A structurally different $LTA_4H$ inhibitor (JNJ26993135) as well as a BLT1 antagonist (LY293111) were both efficacious in reversing severe PH and preventing PH-related death, whereas the CysLT antagonist, Montelukast, had little impact (see FIGS. 3A and B). Further, testing demonstrated that resveratrol (another compound with some $LTA_4H$ inhibitory activity) had a relatively high IC50 (indicating weak $LTA_4H$ blocking effects), and resveratrol did not attenuate PH or improve survival. Blocking $LTB_4$, either through inhibition of its biosynthesis or through receptor antagonism, resulted in increased numbers of open arterioles and decreased arteriolar wall thickness in parallel with reduced BALF $LTB_4$ levels; by contrast, antagonizing CysLT1 was not effective in this regard (FIG. 3, C-E).

Furthermore, inhibition of other eicosanoid pathways had little or no capacity to reverse PH, although inhibition of upstream 5-LO (with zileuton) and FLAP (with MK886) mildly attenuated pressures and prevented death. Inhibition of $PLA_2$ (with arachidonyl trifluoromethyl ketone), COX (with aspirin), and epoxyeicosatrienoic acids (EETs) (with dicyclohexyl urea (DCU)) were relatively less therapeutic. Ubenimex and JNJ26993135 treatment significantly reduced the otherwise abundant accumulation of 5-LO expressing periarteriolar macrophages and B cells observed in the lungs of SU-treated athymic rats, and reduced in vivo PAEC apoptosis by suppressing $LTB_4$-mediated inhibition of the Sphk1-eNOS pathway.

In parallel, a different model of rodent PH utilizing SU and exposure to chronic hypoxia in animals not prone to immune dysregulation showed that there was less macrophage inflammation, less evidence of pulmonary $LTB_4$ biosynthesis, and normal levels of serum $LTB_4$; in contrast to the athymic rat model, these PH animals did not respond to ubenimex therapy initiated late in disease development.

In summary, the $LTB_4$-centered therapies provided by the invention include those that block $LTB_4$ biosynthesis via $LTA_4H$ or 5-LO or FLAP inhibition or prevent $LTB_4$ signaling via BLT1/BLT2 antagonism Various embodiments of these therapies employ ubenimex (administered p.o. in immediate release or sustained released formulations) or ubenimex analogs, including novel analogs provided by the invention, or other $LTA_4H$ inhibitors, including but not limited to JNJ26993135, to treat PAH and other vascular disease in humans. In other embodiments, the methods of the invention employ drugs that antagonize $LTB_4$ signal transduction through its receptor BLT1/BLT2, including but not limited to LY293111.

Example 6

Evidence of Increased $LTB_4$ Biosynthesis is Seen in Human PAH

This example shows that $LTB_4$ levels are elevated in the lung and blood of patients with PAH.

Serum from healthy controls, iPAH patients, and CTD-PAH patients was procured from the IRB-approved Stanford Pulmonary Hypertension Biobank. Serum $LTB_4$ was isolated using solid phase extraction and quantified using liquid chromatography and tandem mass spectrometry. Serum $LTB_4$ levels were tested for normality using the Kolmogorov-Smirnov test and mean values compared across cohorts using non-parametric one-way analysis of variance with the Kruskal-Wallis test. A p value of <0.05 was considered significant.

Generally, for all the data reported in these examples, statistical analyses were performed as follows. GraphPad Prism® version 5.0c was used for statistical analysis. Differences between various groups at multiple time points were compared using two-way ANOVA with Bonferroni multiple comparisons test for post hoc analyses. For comparisons between multiple experimental groups at a single time point, Kruskall-Wallis test followed by Dunn's multiple comparisons test for post hoc analyses were used. All data were represented as means±SEM, and p-value of <0.05 was considered significant. In 5 of 6 PAH patients lung samples, $LTA_4H$ expression was notably increased in macrophages clustered around occluded vascular lumens of plexiform lesions. Increased $LTA_4H$ was also expressed in endothelial cells lining the nearly-occluded vascular lumens of the plexiform lesions; in the $6^{th}$ patient, who did not have increased $LTA_4H^+$ pulmonary macrophages, focally-increased $LTA_4H$ expression in the occluded vascular lumen was still observed.

Figure 4:
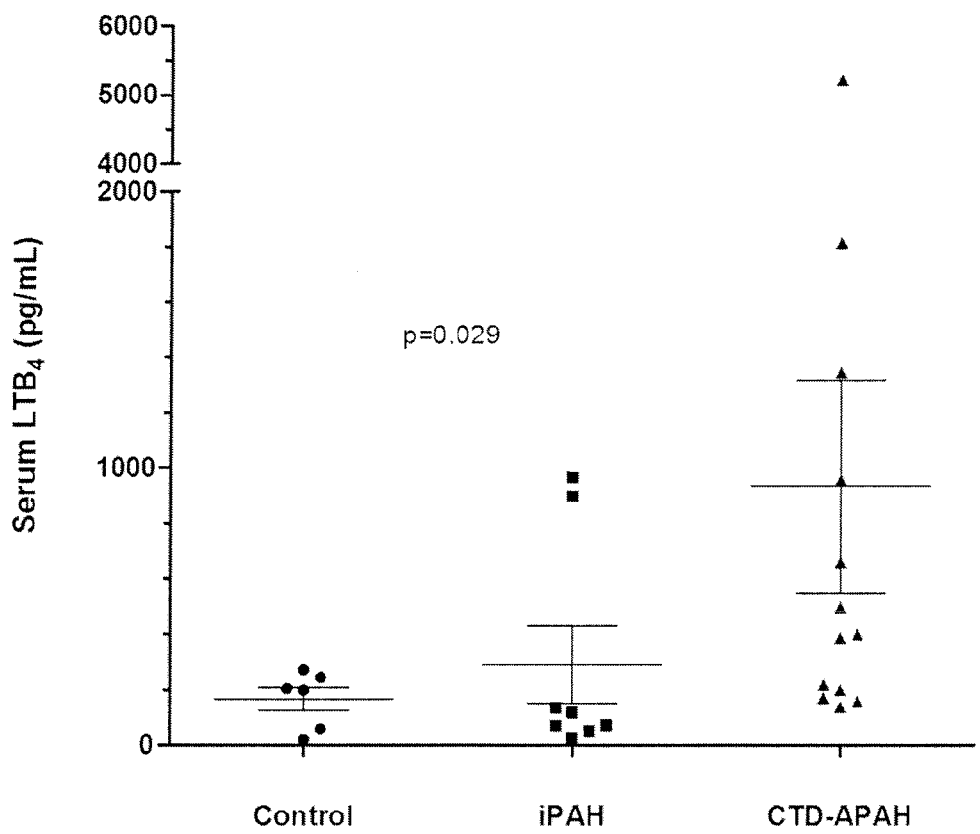
FIG. 4 demonstrates increased plasma $LTB_4$ concentrations in clinical PAH. (A) Plasma $LTB_4$ concentrations in healthy controls and PAH patients (n=27). Data are presented as means±S.D and means±s.e.m. in the figure. P value reflects non-parametric one-way analysis of variance using the Kruskal-Wallis test.

$LTB_4$ plasma levels in 21 PAH patients were compared to 6 healthy individuals (see FIG. 4A). $LTB_4$ levels were elevated significantly in PAH patients, especially in those with connective tissue disorders; these individuals exhibited mean $LTB_4$ levels approximately five-fold higher than those in healthy controls. In contrast, 6 of 8 iPAH patients appeared to have normal $LTB_4$ levels. In conclusion, some, but not all, PAH patients exhibited evidence of increased $LTB_4$ levels in lung macrophages, occluded arteriolar intimal cells, and the systemic circulation.

Therefore, with respect to human disease, the athymic nude rat model is a good model of human PAH characterized by high lung and blood $LTB_4$ levels. Cumulatively, these data demonstrate that $LTB_4$ levels, which can conveniently be determined from blood, breath or sputum samples, are useful as a biomarker for predicting need of treatment and responsiveness to the $LTB_4$-targeted therapies of the invention, with higher levels correlating to need of treatment and likelihood of better responsiveness; further, once treatment is started, declining levels correlate with therapeutic effectiveness.

Example 7

Sustained-Release Oral Formulation of Ubenimex

This example describes the process for preparing a sustained-release formulation of ubenimex (as used for generating certain of the results described in Example 4). The formulation was prepared by adding 100 µl, of PEG-400 to 100 mg of ubenimex, which was then gently mixed into a suspension. A 20% (w/v) aqueous solution of hydroxypropyl-β-cyclodextrin (HPCD) was added to the mixture to bring the volume to 50 ml. The suspension was then vortexed and sonicated at room temperature to provide a clear/homogeneous solution at a 2 mg/ml ubenimex concentration.

Example 8

Ubenimex-Polyvinyl Alcohol (PVA) Dry Powder Formulation

Dry powder ubenimex-PVA microparticles (as used to obtain certain of the results described in Example 4) were obtained by precipitating micro droplets of a precursor solution into a container of continuously stirred acetone using a spray type aerosol nozzle. To obtain the precursor solution, 1.5 g of polyvinyl alcohol (PVA, 75 wt % Mr average~30000), 200 mg of polyvinyl pyrrolidone (PVP, 10 wt %, Mr average~10000), 100 mg of poloxamer 188 (5 wt %, Mr average~8400), 100 mg of L-leucine (5 wt %), and 100 mg ubenimex (5 wt %) were dissolved in a mixture of 12.5 ml DMSO and 8.3 ml Millipore water at room temperature and stirred for 2 hrs. This was followed by 4 hrs of cold sonication (Branson 2510, 100 W). PH of the precursor solution was adjusted to 7, using 1N NaOH or 1N HCl. The solution was sprayed using compressed air (at 25° C., 15 psig, 25 L/min.) into a 1.2 L acetone bath in a glass container stirring at 230 rpm. The microparticles were filtered and dried under a vacuum at room temperature. The dry powder was further ground with a mortar and pestle and filtered through a 63 micron copper sieve.

The ubenimex microparticles were characterized using Hitachi S-3400N VP scanning electron microscope operated at 10-15 kV at a working distance of 8-10 mm. Microparticles were placed on a silicon wafer and imaged after sputter-coating them with 100 A° gold-palladium using a Denton Desk II TSC Sputter Coater (Denton Vacuum).

Breathable drug delivery was achieved using a custom made device based on fluidized bed principles. The device consists of a fluidized bed and an adapter cone for rat nose. A predetermined dose of breathable microparticles was fluidized with $O_2$ and isoflurane at 4 L/min. For results reported in Example 4, rats were under anesthesia for 5 minutes.

Example 9

Ubenimex-Liposome Formulation

This example provides a process for preparing a liposome formulation of ubenimex. In preparing the liposome formulation, 0.5% cholesterol, 1% 1,2-distearoyl-sn-glycero-3-phosphocholine (DSPC) and 0.1% PEG-DSPE were mixed in chloroform/halothane. Next, the solvents were evaporated using a rotary evaporator under vacuum and lyophilization overnight. The thin film of lipids was hydrated with water and sonicated for 30 mins at room temperature. The formed liposomes were purified by using Sephadex G25 column and lyophilized overnight again. Ubenimex (0.64%) was dissolved in water and mixed with 8% PVP. The resulting mixture was then added to the liposome preparation and encapsulation was realized using a step wise hydration and evaporation process. Liposome-containing ubenimex was confirmed by atomic force microscopy, which demonstrated that the liposome-encapsulated ubenimex was ~10 nm in size.

Example 10

Ubenimex-Microparticle Formulation

This example provides a process for preparing a microparticle formulation of ubenimex. In preparing the microparticle formulation, the following components were mixed in 5 ml DMSO with sonication for 5 hours: (1) PVA-30, 83.3% (2) PVP-10, 11.1% (3) Poloxamer-188, 5.56%. The mixture was sprayed using compressed air (at 25° C., 15 psig, 25 L/min.) into a 1.2 L acetone bath in a glass container and was stirred at 230 rpm. The precipitated particles were filtered and dried under a vacuum at room temperature. The resulting mixture was then added to the ethanol dissolved ubenimex and encapsulation was realized using a step wise hydration and evaporation process. Scanning electron microscope measurements demonstrated that the microparticle-encapsulated ubenimex was ~5-20 µm in size.

Example 11

Other Ubenimex Formulations

This example describes processes for preparing other ubenimex formulations of the invention.

In general, liposome-formulized ubenimex was mixed with DSPC and dipalmitoylphosphatidylcholine (DPPC) that were dissolved in EtOH. L-leucine solution was prepared by dissolving L-leucine in water and NaOH. The pH of the L-leucine solution was then adjusted to 8.5-9.0. The ubenimex containing mixture was then mixed with L-leucine solution slowly with stirring. The mixture from the previous step was atomized and dried to achieve the final formulation.

Compositions of the invention include: ubenimex (43%), DPPC (11%), DSPC (11%), L-leucine (35%) and ubenimex (43%), DPPC (22%), L-leucine (35%).

Example 12

Formulation of Ubenimex Analogs

This example shows that ubenimex analogs therapies of the invention are highly effective for reversing advanced (life-threatening) PH, as demonstrated in animal models (the athymic nude rat model described in Example 1).

To demonstrate the in vivo efficacy of various compounds of the invention, the SU-athymic rat model of experimental PAH was used. The compound of Formula III, as well as ubenimex methy ester, mono-acryl ubenimex, mono-acyl ubenimex bromide, di-acyl ubenimex, di-acyl ubenimex bromide, mono-acyl ubenimex-OH, and di-acyl ubenimex-OH, were dosed at 1 mg/kg p.o. daily, and ubenimex was dosed at 1 mg/kg p.o. daily as a control. All animals were sacrificed 5 wk after SU administration for hemodynamic measurements. Serial ECHO revealed that all the compounds were effective. Serial improvement was observed from the time of treatment initiation. Interval improvement was manifested by decreasing RV wall thickness and increasing pulmonary artery acceleration times (PAAT) after initiation of treatment. Hemodynamic data demonstrated a normalized RVSP, with an average pressure of 35 mm Hg. The compound of Formula III was especially efficacious: treatment with that compound reduced the RVSP to a mean pressure of 28 mm Hg, which is nearly equivalent to the healthy control group (RVSP typically around 25 mmHg). Decreased RVH ratios were observed in all treatment groups, with an average ratio of 0.36. Here again, the compound of Formula III was notable: treatment with that compound yielded an RVH ratio of 0.29. RVH for healthy rats is generally about 0.25. All compounds demonstrated improved survival in this model.

Example 13

Synthesis of Ubenimex Analogs

1) Synthesis of Ubenimex Methyl Ester

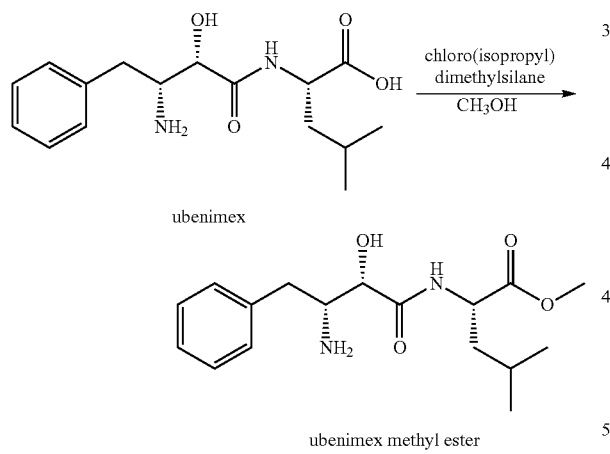

Ubenimex methyl ester, (S)-methyl 2-((2S,3R)-3-amino-2-hydroxy-4-phenylbutanamido)-4-methylpentanoate, was synthesized as follows. 1.0 g of ubenimex and 3.55 g of chloro(isopropyl)dimethylsilane were mixed slowly in a round bottom flask with stirring for 1 hr. After 1 hr, 10 ml methanol were added and the reaction mixture was stirred overnight at room temperature. At the end of the reaction, the reaction solution was dried. The residue was washed with diethyl ether and vaporized in vacuum. The product was characterized by NMR and mass spectrometry. $^1$H NMR and mass spectrometry: δ 7.84 (s, 1H), 7.30 (m, 2H), 7.24 (m, 3H), 4.62 (t, 1H), 3.98 (s, 2H), 3.74 (s, 3H), 3.60 (d, 1H), 3.00 (m, 1H). 2.60 (m, 1H), 2.42 (s, 1H), 1.65 (m, 1H), 1.25 (m, 1H), 0.92 (d, 6H). LC/MS: Calcd. [M+H]/z: 323.2. found: [M+H]/z: 323.0.

2) Synthesis of Mono-Acyl Ubenimex

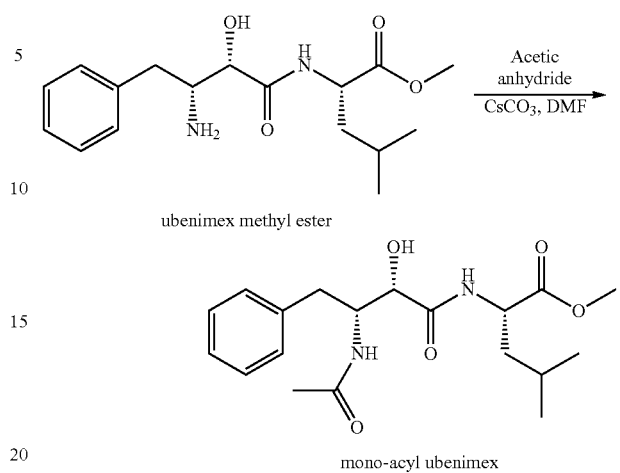

Mono-acyl ubenimex, (S)-methyl 2-((2S,3R)-3-acetamido-2-hydroxy-4-phenylbutanamido)-4-methylpentanoate, was synthesized as follows. 1.0 g of ubenimex methyl ester and 2.0 g of cesium carbonate were dissolved in N—N,dimethyl formamide (DMF) at room temperature. 312 mg of acetic anhydrate were then added to the mixture dropwise and were stirred for 16 hrs at 50° C. Progress of the reaction was checked by thin layer chromatography (TLC). After completion of the reaction, the solution was cooled to room temperature and was diluted with 0.2 N HCl, followed by extraction with ethyl acetate (3 times), washing with saturated aqueous sodium bicarbonate (1 time) and sodium chloride (2 times), and drying over anhydrous sodium sulfate. The solvent was evaporated and purified using silica column with methanol/methylene chloride as eluent. The product was characterized by NMR and mass spectrometry. 1H NMR: δ 7.31 (s, 1H), 7.28 (m, 2H), 7.18 (m, 3H), 6.26 (s, 1H), 4.55 (m, 1H), 4.16 (d, 1H), 4.12 (m, 1H), 3.70 (s, 3H), 3.18 (d, 2H), 1.88 (s, 3H), 1.60 (m, 3H), 0.90 (d, 6H). LC/MS: Calcd. [M+H]/z: 365.2. found: [M+H]/z: 365.3.

3) Synthesis of Di-Acyl Ubenimex

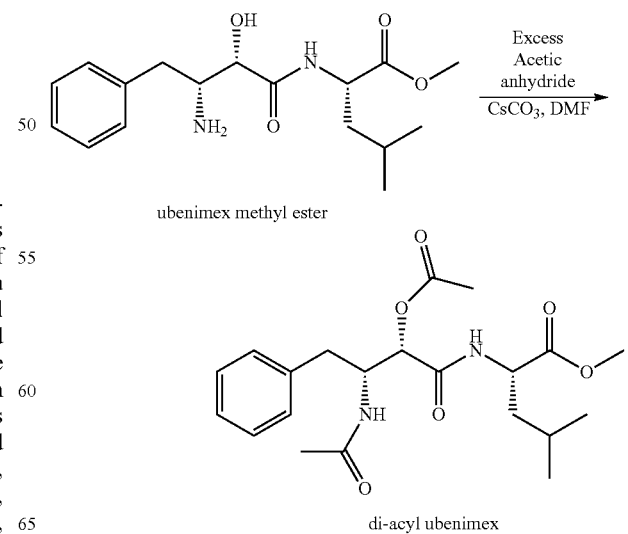

Di-acyl ubenimex, (S)-methyl 2-((2S,3R)-3-acetamido-2-acetoxy-4-phenylbutanamido)-4-methylpentanoate was synthesized as follows: 1.0 g of ubenimex methyl ester and 2.0 g of cesium carbonate were dissolved in 10 ml DMF and stirred at room temperature. 624 mg of acetic anhydrate were then added to the previous reaction mixture dropwise with stirring for 16 hrs more at 60° C. Progress of the reaction was checked by TLC. After completion of the reaction, the mixture was cooled to room temperature and was then diluted with 0.2 N HCl, followed by extraction with ethyl acetate (3 times). The combined organic layers were washed with saturated aqueous sodium bicarbonate (1 time) and sodium chloride (2 times), and then dried over anhydrous sodium sulfate. The solvent was evaporated and purified using silica column with methanol/methylene chloride as eluent. The product was characterized by NMR and mass spectrometry. $^1$H NMR: δ 8.54 (s, 1H), 7.26 (m, 2H), 7.18 (m, 3H), 6.43 (d, 1H), 6.35 (m, 1H), 5.21 (d, 1H), 4.62 (m, 2H), 3.74 (s, 3H), 2.92 (m, 1H), 2.75 (m, 1H), 2.10 (s, 3H), 1.90 (s, 3H), 1.66 (m, 3H), 0.92 (d, 6H). LC/MS: Calcd. [M+H]/z: 407.2. found: [M+H]/z: 407.2.

4) Synthesis of Mono-Acyl Ubenimex Bromide

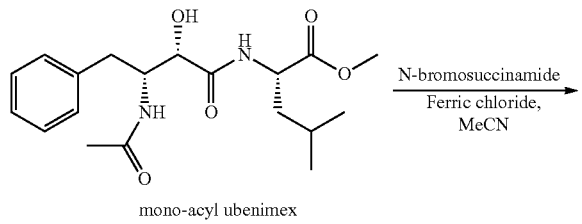
mono-acyl ubenimex

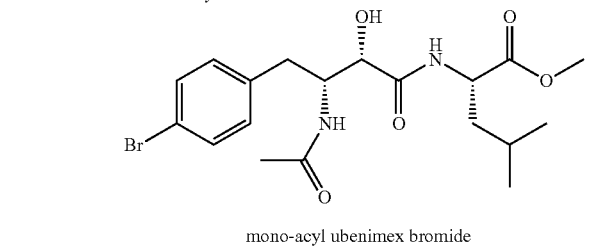
mono-acyl ubenimex bromide

Mono-acyl ubenimex bromide, (S)-methyl 2-((2S,3R)-3-acetamido-4-(4-bromophenyl)-2-hydroxybutanamido)-4-methylpentanoate, was synthesized as follows. 200 mg of mono-acyl ubenimex were first dissolved in 5 ml acetonitrile. 100 mg of ferric chloride and 116 mg of N-bromosuccinamide were then added to the solution mixture and were kept on stirring at room temperature for 16 hrs. After completion of reaction, the reaction solution was diluted with water and was then extracted with ethyl acetate. The organic layer was evaporated under vacuum and purified by column chromatography. The product was characterized by mass spectrometry. LC/MS: Calcd. [M+H]/z: 443.1/445.1. found: [M+H]/z: 443.3/445.1.

5) Synthesis of Di-Acyl Ubenimex Bromide

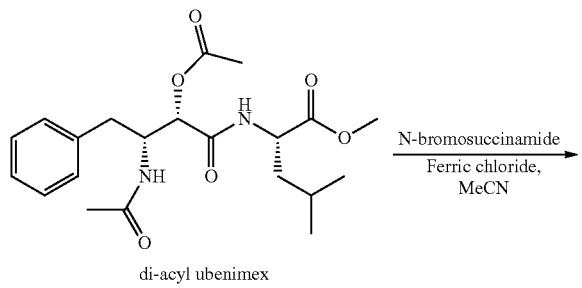
di-acyl ubenimex

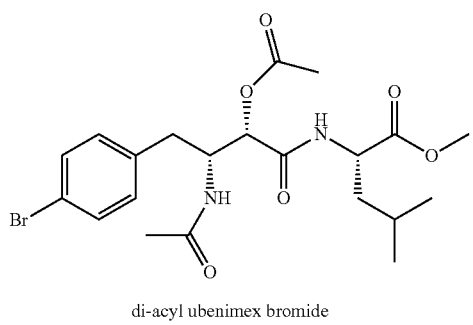
di-acyl ubenimex bromide

Di-acyl ubenimex bromide, (S)-methyl 2-((2S,3R)-3-acetamido-2-acetoxy-4-(4-bromophenyl)butanamido)-4-methylpentanoate was synthesized as follows. Di-acyl ubenimex 200 mg were first dissolved in acetonitrile 5 ml. 100 mg of ferric chloride and 116 mg of N-bromosuccinamide were then added to the mixture and were kept on stirring at room temperature for 16 hrs. After completion of reaction, the reaction mixture was diluted with water and was then extracted with ethyl acetate. The organic layer was evaporated under vacuum and purified by column chromatography. The product was characterized by NMR and mass spectrometry. $^1$H NMR: δ 7.26 (m, 2H), 7.18 (m, 3H), 6.57 (d, 1H), 6.38 (m, 1H), 5.09 (d, 1H), 4.62 (m, 2H), 3.74 (s, 3H), 2.92 (m, 1H), 2.75 (m, 1H), 2.10 (s, 3H), 1.90 (s, 3H), 1.66 (m, 2H), 0.92 (d, 6H). LC/MS: Calcd. [M+H]/z: 485.1/487.1. found: [M+H]/z: 485.1/487.2.

6) Synthesis of Mono-Acyl Ubenimex-OH

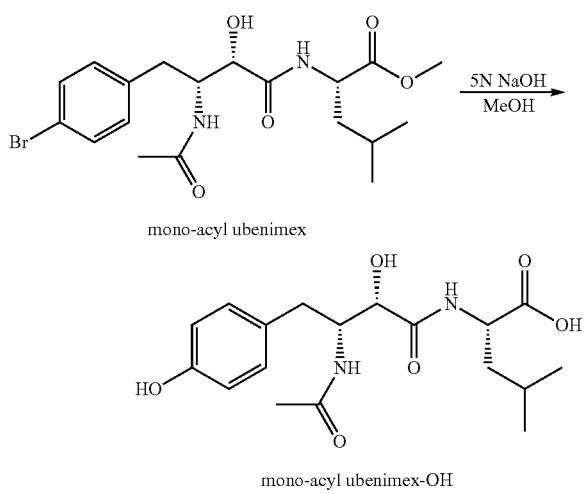

Mono-acyl ubenimex-OH, (S)-methyl 2-((2S,3R)-3-acetamido-2-hydroxy-4-(4-hydroxyphenyl)butanamido)-4-methylpentanoate, was synthesized as follows. 260 mg of mono-acyl ubenimex was first dissolved in 5 ml of methanol. The solution was then treated with 5 N NaOH at reflux for 48 hrs. The mixture was cooled to room temperature and was carefully neutralized with 5N HCl, followed by extraction with ethyl acetate. The organic layer was evaporated under vacuum and purified by column chromatography. The product was characterized by mass spectrometry. LC/MS: Calcd. [M+H]/z: 367.2. found: [M+H]/z: 367.3.

7) Synthesis of Di-Acyl Ubenimex-OH

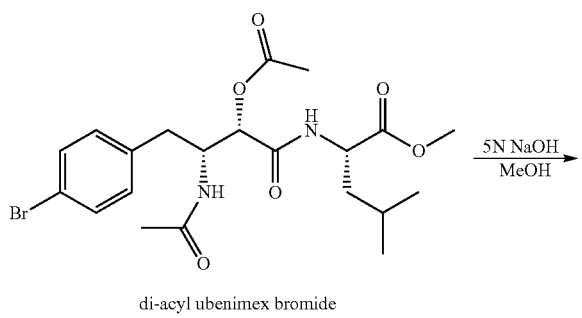

di-acyl ubenimex bromide di-acyl ubenimex-OH

Di-acyl ubenimex-OH, (S)-methyl 2-((2S,3R)-3-acetamido-2-acetoxy-4-(4-hydroxyphenyl)butanamido)-4-methylpentanoate, was synthesized as follows. 130 mg of di-acyl ubenimex was first dissolved in 5 ml of methanol and was then treated with 5 N NaOH at reflux for 48 hrs. The mixture was cooled to room temperature and was carefully neutralized with 5N HCl, followed by extraction with ethyl acetate. The organic layer was evaporated under vacuum and purified by column chromatography. The product was characterized by mass spec. LC/MS: Calcd. (di-acyl) [M+H]/z: 409.2, not found, Calcd. (mono-acyl) [M+H]/z: 367.2. found: [M+H]/z: 367.3.

8) Synthesis of the Compound of Formula III

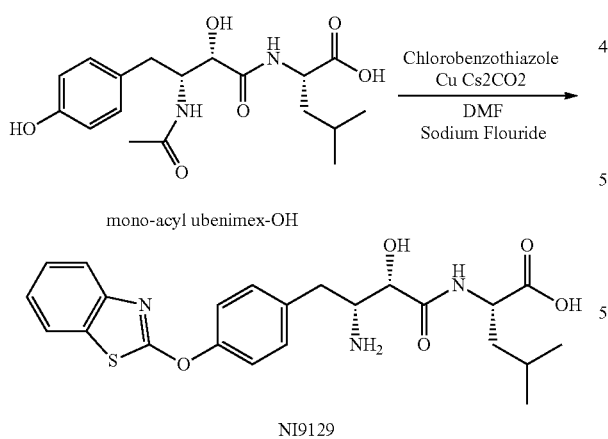

mono-acyl ubenimex-OH

NI9129

The compound of Formula III, 1, (S)-2-((2S,3R)-3-amino-4-(4-(benzo[d]thiazol-2-yloxy)phenyl)-2-hydroxybutanamido)-4-methylpentanoic acid (structure shown as "NI9121" in the reaction scheme above), was synthesized as follows. 65 mg of mono-acyl ubenimex-OH and 50.7 mg of 2-chlorobenzo[d]thiazole were suspended in 5 ml of DMF in a round bottomed flask over an oil bath with condenser. 19 mg of copper powder and 290 mg of cesium carbonate were then added to this mixture and were heated with stirring under nitrogen atmosphere for 18 hrs. After completion of the reaction, DMF was evaporated using a rotary evaporator, and the residue was dissolved in ethyl acetate, followed by washing and separation with 1N NaOH and water. The organic layer was dehydrated using anhydrous sodium sulfate and then evaporated under vacuum. Product from the previous step was further deacylated using sodium fluoride and then purified by HPLC to obtain the compound of Formula III. The product was characterized by mass spectrometry. LC/MS: Calcd. [M+H]/z: 458.2. found: [M+H]/z: 458.4.

Example 14

Alternative Method of Synthesis of the Compound of Formula III by Solid Phase Synthesis This example provides an alternative method of synthesis for the compound of Formula III. Structurally related compounds can be made employing this method.

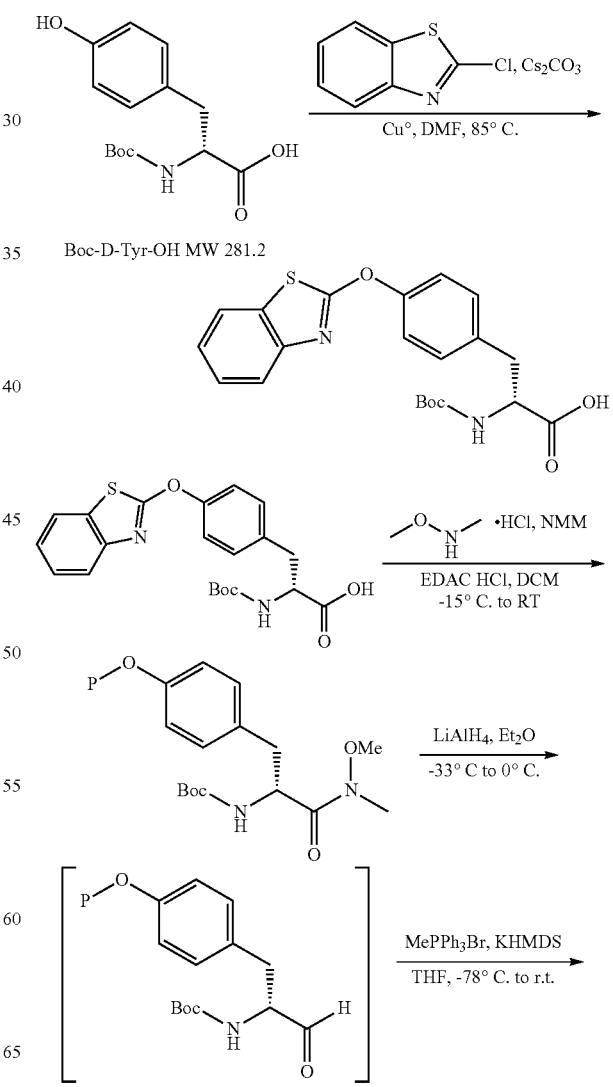

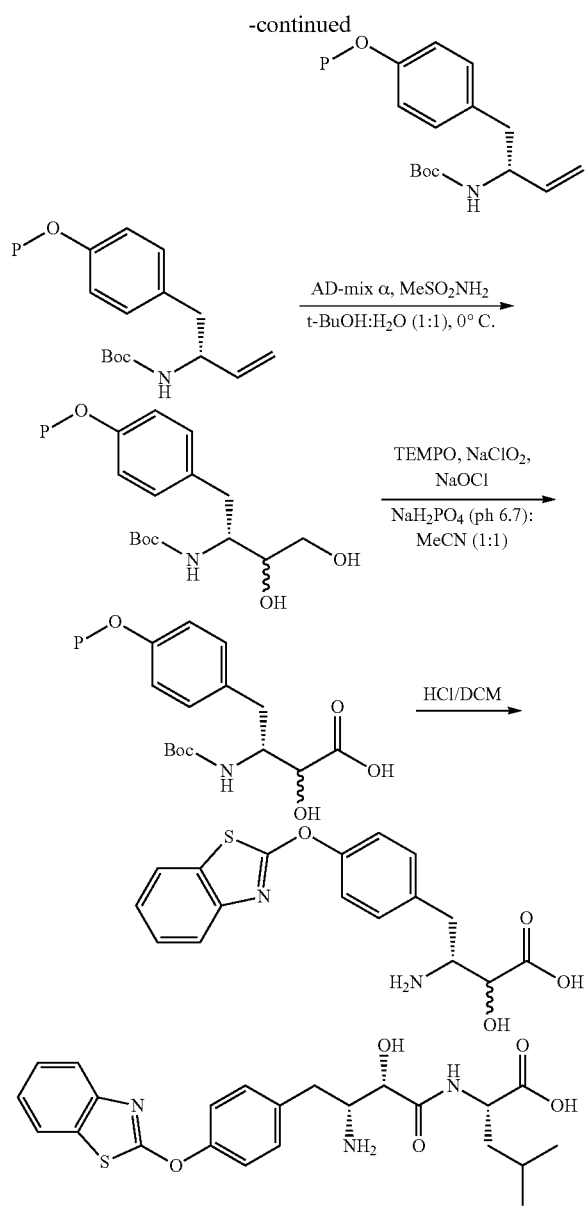

P = protection group

What is claimed is:

1. A method of treating pulmonary arterial hypertension in a subject in need thereof, said method comprising administering to said subject (2S)-2-[[(2S,3R)-3-amino-2-hydroxy-4-phenylbutanoyl]amino]-4-methylpentanoic acid or a pharmaceutically acceptable salt thereof at a daily dose of 100-200 mg/day, wherein the daily dose is administered on consecutive days for at least a month.

2. The method of claim 1, wherein the (2S)-2-[[(2S,3R)-3-amino-2-hydroxy-4-phenylbutanoyl]amino]-4-methylpentanoic acid or a pharmaceutically acceptable salt thereof is administered to the subject at a dose of 60 mg twice a day or 60 mg three times a day.

3. The method of claim 1, wherein the (2S)-2-[[(2S,3R)-3-amino-2-hydroxy-4-phenylbutanoyl]amino]-4-methylpentanoic acid or pharmaceutically acceptable salt thereof is present in a pharmaceutical formulation that comprises at least one pharmaceutically acceptable carrier.

4. The method of claim 1, wherein said pulmonary arterial hypertension is immune dysregulated pulmonary arterial hypertension.

5. The method of claim 1, wherein the subject has an elevated leukotriene B4 level at least two-fold higher relative to a subject not in need of said inhibitor.

6. The method of claim 1, further comprising determining at least one of leukotriene B4 level, pulmonary vascular resistance, pulmonary arterial pressure, cardiac index, pulmonary capillary wedge pressure, right atrial pressure, six-minute walk distance, brain natriuretic peptide level, diffusion of lung capacity, survival rate, or time to death after diagnosis of pulmonary arterial hypertension following administration of said inhibitor.

7. The method of claim 1, wherein the (2S)-2-[[(2S,3R)-3-amino-2-hydroxy-4-phenylbutanoyl]amino]-4-methylpentanoic acid or a pharmaceutically acceptable salt thereof is administered orally or via inhalation.

8. A method of treating pulmonary arterial hypertension in a subject in need thereof comprising:
    a. determining the level of leukotriene B4 in a sample obtained from the subject;
    b. comparing the level of leukotriene B4 in the sample to a control value determined from an individual not suffering from pulmonary arterial hypertension or from the subject in need thereof prior to diagnosis of pulmonary arterial hypertension;
    c. selecting a subject having an elevated level of leukotriene B4 relative to the control value; and
    d. administering to the subject selected in step c a therapeutically effective amount of (2S)-2-[[(2S,3R)-3-amino-2-hydroxy-4-phenylbutanoyl]amino]-4-methylpentanoic acid or a pharmaceutically acceptable salt thereof, thereby treating pulmonary arterial hypertension in the subject.

9. The method of claim 8, wherein the sample is obtained from the breath, sputum, tissue, plasma, serum, or urine of the subject or the individual not suffering from pulmonary arterial hypertension.

10. The method of claim 8, wherein the elevated level of leukotriene B4 is at least two-fold higher than the control value.

11. The method of claim 8, wherein the control value is 400 pg/mL or less.

12. The method of claim 11, wherein the control value is 100 pg/mL or less.

13. The method of claim 8, wherein the control value is 10 pg/mg of tissue or less.

14. The method of claim 8, wherein the elevated level of leukotriene B4 is 100 pg/mL or higher.

15. The method of claim 8, wherein the elevated level of leukotriene B4 is 10 pg/mg of tissue or more.

16. The method of claim 1, wherein the subject is a human.

17. The method of claim 8, wherein the subject is a human.

18. A method of reversing established pulmonary arterial hypertension in a subject in need thereof, said method comprising:
    administering to said subject (2S)-2-[[(2S,3R)-3-amino-2-hydroxy-4-phenylbutanoyl]amino]-4-methylpentanoic acid or a pharmaceutically acceptable salt thereof at a daily dose of 100-200 mg/day, wherein the daily dose is administered on consecutive days for at least a month; wherein said treatment is effective in reversing established pulmonary arterial hypertension.

* * * * *